US012065651B2

(12) United States Patent
Tuller et al.

(10) Patent No.: US 12,065,651 B2
(45) Date of Patent: Aug. 20, 2024

(54) VIRAL SYNTHETIC NUCLEIC ACID SEQUENCES AND USE THEREOF

(71) Applicant: SYNVACCINE LTD., Tel-Aviv (IL)

(72) Inventors: Tamir Tuller, Herzelia Pituach (IL); Eli Goz, Herzliya (IL); Oriah Mioduser, Tel Aviv (IL); Alon Diament, Tel Aviv (IL)

(73) Assignee: SYNVACCINE LTD., Tel Aviv (IL)

( * ) Notice: Subject to any disclaimer, the term of this patent is extended or adjusted under 35 U.S.C. 154(b) by 1050 days.

(21) Appl. No.: 16/480,671

(22) PCT Filed: Jan. 25, 2018

(86) PCT No.: PCT/IL2018/050093
§ 371 (c)(1),
(2) Date: Jul. 24, 2019

(87) PCT Pub. No.: WO2018/138727
PCT Pub. Date: Aug. 2, 2018

(65) Prior Publication Data
US 2019/0359990 A1 Nov. 28, 2019

Related U.S. Application Data

(60) Provisional application No. 62/450,115, filed on Jan. 25, 2017.

(51) Int. Cl.
*C12N 15/67* (2006.01)
*C12N 7/00* (2006.01)
*G16B 25/10* (2019.01)

(52) U.S. Cl.
CPC ............. *C12N 15/67* (2013.01); *C12N 7/00* (2013.01); *G16B 25/10* (2019.02); *C12N 2710/16621* (2013.01); *C12N 2710/16634* (2013.01); *C12N 2710/16662* (2013.01); *C12N 2770/24121* (2013.01); *C12N 2770/24134* (2013.01); *C12N 2770/24162* (2013.01); *C12N 2795/10321* (2013.01); *C12N 2795/10362* (2013.01); *C12N 2800/22* (2013.01); *C12N 2840/10* (2013.01)

(58) Field of Classification Search
None
See application file for complete search history.

(56) References Cited

U.S. PATENT DOCUMENTS 7,561,973 B1 * 7/2009 Welch ............... G16B 30/00
536/23.1
8,846,051 B2 9/2014 Kew et al.

FOREIGN PATENT DOCUMENTS

WO 2006042156 A9 4/2006
WO 2016077123 A1 5/2016

OTHER PUBLICATIONS

Maertens et al: "Gene optimization mechanisms: A multi-gene study reveals a high success rate of full-length human proteins expressed in *Escherichia coli*." Protein Science vol. 19, Issue7, pp. 1312-1326, 2010, XP55441307.
Mitarai et al: "Control of ribosome traffic by position-dependent choice of synonymous codons." Physical Biology, vol. 10, No. 5, 20013. XP20251701.
Nagata et al: "Codon Optimization Effect on Translational Efficiency of DNA Vaccine in Mammalian Cells: Analysis of Plasmid DNA Encoding a CTL Epitope Derived from Microorganisms." Biochemical and Biophysical Research Communications, vol. 261, Issue 2, pp. 445-451, 1999. XP000857845.
Virus Attenuation by Genome-Scale Changes in Codon Pair Bias; Coleman, J. R., Papamichail, D., Skiena, S., Futcher, B., Wimmer, E., & Mueller, S. (2008). Virus Attenuation by Genome-Scale Changes in Codon Pair Bias. Science, 320(5884), 1784-1787. doi:10.1126/science.1155761.
Significant differences in terms of codon usage bias between bacteriophage early and late genes: a comparative genomics analysis; Mioduser, O., Goz, E., & Tuller, T. (2017). Significant differences in terms of codon usage bias between bacteriophage early and late genes: a comparative genomics analysis. BMC Genomics, 18(1). doi: 10.1186/s12864-017-4248-7.
Evidence of translation efficiency adaptation of the coding regions of the bacteriophage lambda; Eli Goz, Oriah Mioduser, Alon Diament, Tamir Tuller, DNA Research, vol. 24, Issue 4, Aug. 2017, pp. 333-342.

\* cited by examiner

*Primary Examiner* — Stacy B Chen
(74) *Attorney, Agent, or Firm* — The Roy Gross Law Firm, LLC; Roy Gross

(57) ABSTRACT

Nucleic acid molecules comprising a coding sequence with at least one codon substituted to a synonymous codon, a modified form of a virus comprising the nucleic acid molecules of the invention, and methods for producing these nucleic acid molecules, and viruses, are provided.

18 Claims, 34 Drawing Sheets

Specification includes a Sequence Listing.

| | Clustering p-value ( x 10² ) | | | | | | | | | | | | | |
|---|---|---|---|---|---|---|---|---|---|---|---|---|---|---|
| CUB clustering | < 0.1 | 33 | 12 | 1 | < 0.1 | 4.9 | 24 | 29 | 10 | < 0.1 | 1 | 19 | 63 | 1 |
| AA clustering | 80 | 19 | 13 | 4 | 40 | 11 | 0.1 | 2 | 15 | < 0.1 | < 0.1 | 49 | 6 | < 0.1 |
| | P 2345 | Phi C31 | XP 10 | Mu | Pak-P3 | T7 | Phi eco32 | S.2972 | S.DT1 | Phi R137 | Phi Ys40 | Phi 29 | Fah | T4 |

VIRAL SYNTHETIC NUCLEIC ACID SEQUENCES AND USE THEREOF

RELATED APPLICATIONS

This application is a National Phase of PCT Patent Application No. PCT/IL2018/050093 having International filing date of Jan. 25, 2018, which claims the benefit of priority of U.S. Provisional Patent Application No. 62/450,115, filed on Jan. 25, 2017. The contents of the above applications are all incorporated by reference as if fully set forth herein in their entirety.

FIELD OF INVENTION

The present invention is directed to the field of viral genome optimization.

BACKGROUND OF THE INVENTION

Deciphering the regulatory information encoded in the genomes of phages and other viruses, and the relation between the nucleotides composition of the coding regions and the viral fitness is of great interest in recent years. It has been suggested that ribosome profiling, which enables in vivo genome wide monitoring of ribosome states at a resolution of a single nucleotide, is a useful tool for deciphering the coding complexity of viral (and other organisms) genomes. Specifically, it was shown that ribosome profiling enables detecting novel (possibly very short) coding regions and estimating the translation status of various open reading frames.

Gene expression within different DNA viruses, such as herpeses, lenti-retro, polyoma, papilloma, adeno, parvo and various families of bacteriophages is regulated in a temporal fashion and can be divided into early and late stages with respect to the viral replication cycle. The early genes are expressed following the entry into the host cell and code typically for non-structural proteins that are responsible for different regulatory functions in processes such as: viral DNA replication, activation of late genes expression, transnuclear transport, interaction with the host cell, induction of the cell's DNA replication machinery necessary for viral replication, etc. Late genes largely code for structural proteins required for virion assembly; they are generally highly expressed and their expression is usually induced or regulated by early genes.

It has been suggested that viral coding sequences are shaped by evolution to improve their expression and fitness. Several works have implicated codon usage in the temporal regulation of viral gene expression, specifically showing that the composition of codons in coding sequences of viruses is regulated.

Vaccines, and their discovery, are topics of singular importance in present-day biomedical science; however, the discovery of vaccines has hitherto been primarily empirical in nature requiring considerable investments of time, efforts and resourced. To overcome the numerous pitfalls attributed to the classical vaccine design strategies, more efficient and robust rational approaches based on computer-based methods are highly desirable. One direction in designing in-silico vaccine candidates may be based on exploiting the synonymous information encoded in the genomes for attenuating the viral replication cycle while retaining the wild type proteins.

Several studies used codon deoptimization of viral coding sequences, in order to design candidates for life attenuated vaccines (see e.g., Baker et al., 2015; Cheng et al., 2015; Mueller et al., 2006a; Nogales et al., 2014). However, viruses infect many different cell types and tissues which will have different codon compositions in their highly-expressed genes. Further, a particular cell or tissue may significantly deviate from the codon usage bias of an entire organism. In addition, the highly-expressed genes for a particular cell or tissue may not be known which would limit the precision of the reference codon composition. Lastly, the same virus may infect different hosts causing multiple selectional pressures on codons resulting in a combined codon usage that may deviate from the codon usage of a certain host organism

SUMMARY OF THE INVENTION

The present invention provides a nucleic acid molecule comprising a codon substituted to a synonymous codon. The invention also provides modified viruses and vaccine compositions comprising the nucleic acid molecules of the invention, as well as methods for producing and using these viruses and vaccine compositions.

According to the first aspect, there is provided a nucleic acid molecule comprising a coding sequence, the coding sequence comprises at least one codon substituted to a synonymous codon, the synonymous codon has a parameter that effects translation rate which differs from the parameter of the at least one codon in a set of coordinately expressed viral genes.

According to one embodiment, the parameter than effects translation rate is selected from the group consisting of: relative synonymous codons frequencies (RSCF), relative codon-tRNA adaptation, codon typical decoding rate (TDR), GC content, average repetitive substring index, codon pair bias, dinucleotide bias, nucleotide bias and amino acid bias. According to one embodiment, the parameter than effects translation rate is selected from the group consisting of: relative synonymous codons frequencies (RSCF), relative codon-tRNA adaptation and codon typical decoding rate (TDR).

According to one embodiment, the set of coordinately expressed viral genes are a subset of a virus's total genome.

According to one embodiment, the set of viral genes is selected from the group consisting of: genes with a common structure, genes with common temporal expression during a virus's life cycle, genes encoding for proteins having common function, genes translated at a common cellular location and genes encoding for proteins having common cellular localization.

According to one embodiment, at least ten codons of the coding sequence have been substituted. According to one embodiment, at least 10% of the codons of the coding sequence have been substituted.

According to one embodiment, the synonymous codon has a parameter that results in faster translation in a particular cellular context relative to the at least one codon that has been substituted. According to one embodiment, a plurality of codons having synonymous codons with faster translation rates in a particular cellular context have been substituted. According to one embodiment, the at least one codon is substituted to the fastest translating synonymous codon in a particular cellular context. According to one embodiment, the coding sequence is optimized for expression that is the same as the set of viral genes.

According to one embodiment, the synonymous codon has a parameter that results in slower translation in a particular cellular context relative to the at least one codon that has been substituted. According to one embodiment, a plurality of codons having synonymous codons with slower translation rates in a particular cellular context have been substituted. According to one embodiment, the at least one codon is substituted to the slowest translating synonymous codon in a particular cellular context. According to one embodiment, the coding sequence is de-optimized for expression that is the same as said set of viral genes.

According to one embodiment, the coding sequence is selected from the group consisting of: a viral gene, a mammalian gene, a heterologous transgene or a fragment thereof.

According to one embodiment, the mammalian gene is a human gene.

According to one embodiment, the temporal expression during a virus's life cycle is selected from the group consisting of: early expression in the virus life cycle, intermediate expressing in the virus life cycle, and late expression in the virus life cycle.

According to one embodiment, the optimization is selected from optimizing translation efficiency and optimizing protein yield.

According to another aspect, there is provided a modified virus comprising the nucleic acid molecule of the present invention.

According to another aspect, there is provided an attenuated form of a virus, comprising the nucleic acid molecule of the present invention, wherein:
a. the coding sequence is an essential viral sequence endogenously expressed during a defined period of the virus's life cycle, and
b. the set of genes is a plurality of viral genes expressed during the defined period of the virus's life cycle, and
wherein the virus is devoid of the endogenous viral sequence.

According to another aspect, there is provided a vaccine composition for inducing a protective immune response in a subject, the vaccine composition comprising:
a. the attenuated virus of the present invention, and
b. pharmaceutically acceptable carrier or adjuvant.

According to another aspect, there is provided a method for vaccinating a subject at risk of viral infection, the method comprising, administering to the subject the vaccine composition of the present invention.

According to another aspect, there is provided a method for producing a nucleic acid molecule optimized for expression in a particular cellular context, the method comprising:
a. selecting a coding sequence,
b. selecting a reference set of genes expressed in a particular cellular context,
c. for each codon of the coding sequence, computing a parameter that effects translation rate for the codon and its synonymous codons over all sequences in the reference set, and
d. substituting at least one codon of the coding sequence with a synonymous codon with a faster rate of translation,
thereby producing a nucleic acid molecule optimized for expression in a particular cellular context.

According to another aspect, there is provided a method for producing a nucleic acid molecule deoptimized for expression in a particular cellular context, the method comprising:
a. selecting a coding sequence,
b. selecting a reference set of genes expressed particular context,
c. for each codon of the coding sequence, computing a parameter that effects translation rate for the codon and its synonymous codons over all sequences in the reference set, and
d. substituting at least one codon of the coding sequence with a synonymous codon with a slower rate of translation,
thereby producing a nucleic acid molecule optimized for expression in a particular cellular context.

According to one embodiment, the parameter than effects translation is selected from the group consisting of: relative synonymous codons frequencies (RSCF), relative codon-tRNA adaptation, codon typical decoding rate (TDR), GC content, average repetitive substring index, codon pair bias, dinucleotide bias, nucleotide bias and amino acid bias.

According to one embodiment, the parameter than effects translation is selected from the group consisting of: relative synonymous codons frequencies (RSCF), relative codon-tRNA adaptation and codon typical decoding rate (TDR).

According to one embodiment, the particular cellular context is selected from the group consisting of: a specific period of a cell's life cycle, during cellular division, during cellular stress, during apoptosis, during viral infection, or during viral lysogeny of the cell.

According to another aspect, there is provided a method for producing a modified virus, the method comprising:
a. selecting an endogenous viral sequence,
b. selecting a reference set of viral genes,
c. for each codon of said viral sequence, computing a parameter that effects translation rate for the codon and its synonymous codons over all sequences in the reference set,
d. substituting at least one codon of the viral sequence with a synonymous codon with a different translation rate, thereby producing a reengineered viral sequence, and
e. replacing the endogenous viral sequence with the reengineered viral sequence, thereby producing a modified virus.

According to another aspect, there is provided a method for producing an attenuated virus, the method comprising the method of the present invention, wherein,
a. the viral sequence is an essential viral sequence, and
b. the synonymous codon with a different translation rate has a slower translation rate,
thereby producing an attenuated virus.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1A:
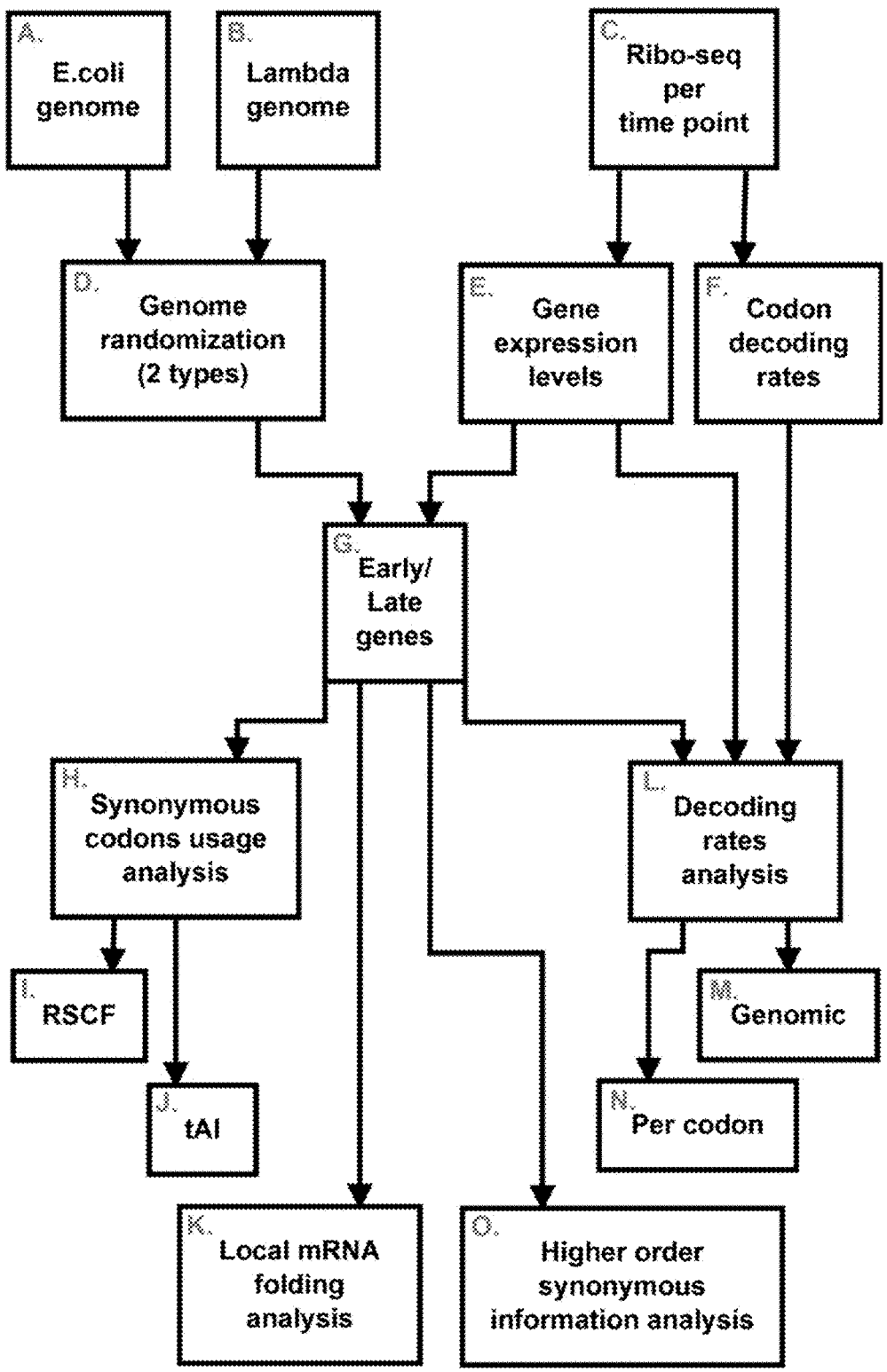
FIGS. 1A-B. (1A) A flow diagram and illustration of some embodiments of the study disclosed herein. (1B). A bar chart depicting relative expression levels of each of the gene groups (early/late) in read count per nucleotide.

The present invention provides, in some embodiments, nucleic acid molecules comprising a coding sequence with at least one codon substituted to a synonymous codon, a modified form of a virus comprising the nucleic acid molecules of the invention, and methods for producing these nucleic acid molecules, and viruses.

By one aspect, the present invention concerns a nucleic acid molecule comprising a coding sequence, the coding sequence comprises at least one codon substituted to a synonymous codon, and the synonymous codon has a parameter that effects translation rate which differs from the parameter of the at least one codon in a set of viral genes.

The term "nucleic acid" is well known in the art. A "nucleic acid" as used herein will generally refer to a molecule (i.e., a strand) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C).

The terms "nucleic acid molecule" include but not limited to single-stranded RNA (ssRNA), double-stranded RNA (dsRNA), single-stranded DNA (ssDNA), double-stranded DNA (dsDNA), small RNA such as miRNA, siRNA and other short interfering nucleic acids, snoRNAs, snRNAs, tRNA, piRNA, tnRNA, small rRNA, hnRNA, circulating nucleic acids, fragments of genomic DNA or RNA, degraded nucleic acids, ribozymes, viral RNA or DNA, nucleic acids of infectios origin, amplification products, modified nucleic acids, plasmidical or organellar nucleic acids and artificial nucleic acids such as oligonucleotides.

"Coding sequence" refers to a nucleic acid sequence that when translated results in an expressed protein. In some embodiments, the coding sequence is to be used as a basis for making codon alterations. In some embodiments, the coding sequence is a viral gene. In some embodiments, the coding sequence is a mammalian gene. In some embodiments, the coding sequence is a human gene. In some embodiments, the coding sequence is a portion of one of the above listed genes. In some embodiments, the coding sequence is a heterologous transgene. In some embodiments, the above listed genes are wild type, endogenously expressed genes. In some embodiments, the above listed genes have been genetically modified or in some way altered from their endogenous formulation. These alterations may be changes to the coding region such that the protein the gene codes for is altered.

The term "heterologous transgene" as used herein refers to a gene that originated in one species and is being expressed in another. In some embodiments, the transgene is a part of a gene originating in another organism.

In some embodiments, the coding sequence is selected from the group consisting of: a viral gene, a mammalian gene, a heterologous transgene or a fragment thereof.

The term "codon" refers to a sequence of three DNA or RNA nucleotides that correspond to a specific amino acid or stop signal during protein synthesis. The codon code is degenerate, in that more than one codon can code for the same amino acid. Such codons that code for the same amino acid are known as "synonymous" codons. Thus, for example, CUU, CUC, CUA, CUG, UUA, and UUG are synonymous codons that code for Leucine. Synonymous codons are not used with equal frequency. In general, the most frequently used codons in a particular cell are those for which the cognate tRNA is abundant, and the use of these codons enhances the rate and/or accuracy of protein translation. Conversely, tRNAs for rarely used codons are found at relatively low levels, and the use of rare codons is thought to reduce translation rate and/or accuracy. "Codon bias" as used herein refers generally to the non-equal usage of the various synonymous codons, and specifically to the relative frequency at which a given synonymous codon is used in a defined sequence or set of sequences.

Thus, to replace a given codon in a nucleic acid by a synonymous but less frequently used codon is to substitute a "deoptimized" codon into the nucleic acid, and to replace a given codon in a nucleic acid by a synonymous but more frequently used codon is to substitute a "optimized" codon.

Calculating the relative frequency of a codon in a gene or a set of genes is understood to refer to counting the number of times a codon is used in that gene or set of genes and counting how many times codons synonymous to that codon are used. Dividing the number of times a codon is used over the total number of codons that code for the same amino acid as that codon gives the relative frequency of that codon. For a non-limiting example, if the codon UUU (coding for Phe) appears 5 times in the set of gene, and UUC (the only synonymous codon to UUU) appears 15 times, then the frequency of codon UUU is 25%.

Synonymous codons are provided in Table 1. The first nucleotide in each codon encoding a particular amino acid is shown in the left-most column; the second nucleotide is shown in the top row; and the third nucleotide is shown in the right-most column.

TABLE 1

| | Genetic code | | | | |
|---|---|---|---|---|---|
| | U | C | A | G | |
| U | Phe | Ser | Tyr | Cys | U |
| | Phe | Ser | Tyr | Cys | C |
| | Leu | Ser | STOP | STOP | A |
| | Leu | Ser | STOP | Trp | G |
| C | Leu | Pro | His | Arg | U |
| | Leu | Pro | His | Arg | C |
| | Leu | Pro | Gln | Arg | A |
| | Leu | Pro | Gln | Arg | G |
| A | Ile | Thr | Asn | Ser | U |
| | Ile | Thr | Asn | Ser | C |
| | Ile | Thr | Lys | Arg | A |
| | Met | Thr | Lys | Arg | G |
| G | Val | Ala | Asp | Gly | U |
| | Val | Ala | Asp | Gly | C |
| | Val | Ala | Glu | Gly | A |
| | Val | Ala | Glu | Gly | G |

In some embodiments, at least 5, at least 10, at least 15, at least 20, at least 25, at least 30, at least 35, at least 40, at least 45, or at least 50 codons of the coding sequence have been substituted. Each possibility represents a separate embodiment of the present invention. One skilled in the art will be able to determine based on the virus and the host cells the minimum number of codons to be substituted. In some embodiments, protein expression after substitution can be measured and compared to protein expression without substitutions to determine if a sufficient number of codons have been substituted.

In some embodiments, greater than 5%, greater than 10%, greater than 15%, greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, greater than 95%, or 100% of all codons in the target sequence have been substituted. Each possibility represents a separate embodiment of the present invention.

In some embodiments, greater than 5%, greater than 10%, greater than 15%, greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, greater than 95%, or 100% of codons that have synonymous codons with higher frequencies have been substituted. Each possibility represents a separate embodiment of the present invention.

In some embodiments, greater than 5%, greater than 10%, greater than 15%, greater than 20%, greater than 25%, greater than 30%, greater than 35%, greater than 40%, greater than 45%, greater than 50%, greater than 55%, greater than 60%, greater than 65%, greater than 70%, greater than 75%, greater than 80%, greater than 85%, greater than 90%, greater than 95%, or 100% of codons that have synonymous codons with lower frequencies have been substituted. Each possibility represents a separate embodiment of the present invention. In some embodiments, a plurality of codons having synonymous codons with different frequencies have been substituted. In some embodiments, a plurality of codons having synonymous codons with higher frequencies have been substituted. In some embodiments, a plurality of codons having synonymous codons with lower frequencies have been substituted.

The term "parameter that effects translation rate" as used herein refers to any characteristic of a codon that impacts the rate at which a codon is translated in a particular and/or pre-determined cellular milieu. Not all codons translate at the same rate, and the rate of codon translation of an entire coding region is proportional to the amount of protein that can be produced by that coding region. Further a single codon may translate at a different rate depending upon the cellular context. As one non-limiting example, the tRNA pool found in a cell can change depending on the condition of the cell. Greater concentration of a particular tRNA may result in faster translation of the codon to which that tRNA corresponds.

In some embodiments, the parameter than effects translation rate is selected from the group consisting of: relative synonymous codons frequencies (RSCF), relative codon-tRNA adaptation, codon typical decoding rate (TDR), GC content, average repetitive substring index, codon pair bias, dinucleotide bias, nucleotide bias and amino acid bias. In some embodiments, the parameter than effects translation rate is selected from the group consisting of: relative synonymous codons frequencies (RSCF), relative codon-tRNA adaptation, codon typical decoding rate (TDR), GC content, average repetitive substring index, codon pair bias, dinucleotide bias, nucleotide bias, amino acid bias and any measure that correlates with any of these parameters. In some embodiments, the parameter than effects translation rate is selected from the group consisting of: relative synonymous codons frequencies (RSCF), relative codon-tRNA adaptation and codon typical decoding rate (TDR). Measuring these parameters are well known in the art and examples of such are described herein. Parameters which are equivalent or correlate with these parameters may also be used.

The term "relative synonymous codons frequencies" as used herein refers to the frequency at which a codon is used relative to other synonymous codons within a specific reference set. Relative synonymous codons frequencies can be represented as a vector which entries correspond to each one of 61 coding codons (stop codons are excluded):

$$RSCF = (RSCF[1], \ldots, RSCF[61])$$
$$RSCF[i] = \frac{q_i}{\sum_{j \in syn[i]} q_j}, \sum_{j \in syn[i]} RSCF[j] = 1$$

where $q_i$ is the number of appearances of codon i in a sequence, syn[i] is a subset of indexes in RSCF pointing at codons synonymous to codon i.

The term "relative codon-tRNA adaptation" as used herein refers to how well a codon is adapted to the tRNA pool relative to other synonymous codons within a specific reference set. The tRNA pool in a cell can change over time depending on the cellular context. In some embodiments, the tRNA pool changes due to viral infection of the cell. In such a case, the tRNA pool will differ during the early phase of a virus's life cycle and the later stage of the virus's life cycle. In this way, a codon can be well adapted to the tRNA pool in one cellular context, but poorly adapted in another.

Relative codon-tRNA adaptation and the tRNA adaptation index (tAI) quantify the adaptation of one codon, or a coding region, respectively, to the tRNA pool. Let tCGNi j be the copy number of the j-th anti-codon that recognizes the i-th codon and let Si j be the selective constraint of the codon-anti-codon coupling efficiency. The S vector [sI:U, sG:C, sU:A, sC:G, sG:U, sI:C, sI:A, sU:G, sL:A] was defined for E. coli as [0, 0, 0, 0, 1, 0.25, 0.81, 1, 0.71] according to optimization performed previously (Sabi R, et al., DNA Research, 2014, 21:511-525). Thus, the absolute adaptiveness value of a codon of type i (1≤i≤61; stop codons are excluded) to the tRNA pool is defined by:

$$W_i = \sum_{j=1}^{n_i} (1 - S_{ij}) tCGN_{ij}$$

For each amino acid, the weight of each of its codons, is computed as the ratio between the absolute adaptiveness value of the codon and the maximal absolute adaptiveness value of the synonymous codons for that amino acid:

$$w_i = \frac{W_i}{\max_{j \in syn[i]} W_j}$$

where $W_i$ is the absolute adaptiveness of codon i in a sequence, syn[i] is a subset of indexes in pointing at codons synonymous to codon i. $w_i$ takes values from 0 (not adapted) to 1 (maximally adapted). If the weight value is zero a value of 0.5 is used tAI is the geometric mean of $w_i$ (relative codon-tRNA adaptation) over codons of a coding sequence.

The term "typical decoding rate" as used herein refers to the estimated time it takes to decode a specific codon and place the appropriate amino acid in the chain of the protein. The methodology of calculating the typical decoding rate, can be found in the Examples section of the present application as well as in the following reference (Dana and Tuller, 2015, G3[Genes, Genomes, Genetics], 5(1): 73-80), which is hereby incorporated into the current application by reference.

The term "GC content" as used herein refers to the percentage of nitrogenous bases on a nucleic acid molecule that are either guanine or cytosine. The binding of guanine and cytosine is a stronger bond that thymine and adenosine or uracil and adenosine. Calculation of GC content is well known in the art and is the sum of all G and C bases divided by the total number of bases.

The term "average repetitive substring index" as used herein refers to the observed overexpression of a substring (a string of nucleotides of at least a length of 3 bases) with in a set of genes that is different than would be expected by chance. As binding sites are coded into gene sequences optimized binding sites are hypothesized to be more frequently used. If that binding site is for the transcription/translation machinery the use of optimized or deoptimized sites for a particular cellular context will effect translation in that cellular context.

The term "codon pair bias" as used herein refers to use of a particular codon pair at a rate that is different than would be expected by chance. Codon pair bias is independent from amino acid and codon bias. It will be understood that the codon pair bias is thus an average of codon pair scores over all codon pairs of all viral coding sequences from a set of viral genes.

Th term "dinucleotide bias" as used herein refers to use of a particular pair of nucleotides at a rate that is different than would be expected by chance. Dinucleotide bias can be determined for any set of genes, be that a whole virus genome or a subset of viral genes.

The term "nucleotide bias" and "amino acid bias" as used herein refer to the use of a nucleotide/AA in a set of sequences that is not what would be expected by chance. These biases can be determined for any set of genes, be that a whole virus genome or a subset of viral genes.

The terms "virus" and "viral" refer to a small infectious agent that replicates only inside the living cells of other organisms. In some embodiments, the viruses described herein are capable of infecting all types of life, including animals, plants and microorganisms. In some embodiments, the virus is capable of infecting an animal. In some embodiments, the virus is capable of infecting a human. In some embodiments, the virus is capable of infecting a plant.

Non-limiting examples of the virus used under the method of the invention include dengue virus, poliovirus, rhinovirus, influenza virus, severe acute respiratory syndrome (SARS) coronavirus, Human Immunodeficiency Virus (HIV), Hepatitis C Virus (HCV), infectious bronchitis virus, Ebolavirus, Marburg virus, West Nile disease virus, Zika, Epstein-Barr virus (EBV) and yellow fever virus.

In some embodiments, the virus is human Simplex virus. In some embodiments, the virus is HIV-1. In some embodiments, the virus is Zika virus.

In some embodiments, the virus is a bacteriophage. In some embodiments, the virus infects mammalian cells. In some embodiments, the virus infects human cells. In some embodiments, the virus is bacteriophage Lambda. In some embodiments, the virus is bacteriophage T4. In some embodiments, the virus is bacteriophage is Pak P3. In some embodiments, the virus is bacteriophage phi29. In some embodiments, the virus is bacteriophage phiYs40. In some embodiments, the virus is bacteriophage Streptococcus DT1. In some embodiments, the virus is bacteriophage Mu. In some embodiments, the virus is bacteriophage phiEco32.

In some embodiments, the virus is bacteriophage p23-45. In some embodiments, the virus is bacteriophage phiR1-37.

In some embodiments, the set of viral genes is more than 1 gene, at least 2 genes, at least 3 genes, at least 5 genes, at least 10 genes, at least 20 genes, at least 30 genes, at least 40 genes, or at least 50 genes. Each possibility represents a separate embodiment of the present invention.

In some embodiments, the set of viral genes is coordinately expressed. In some embodiments, the set of viral genes is the entire viral genome. In some embodiments, the set of viral genes is the entire viral genome or transcriptome wherein the entire viral genome or transcriptome is coordinately expressed. In some embodiments, the set of viral genes is not the entire viral genome or viral transcriptome. In some embodiments, the set of viral genes is a subset of the viral genome. In some embodiments, the set of viral genes is a subset of the viral transcriptome. In some embodiments, the set of viral genes are selected randomly. In some embodiments, the set of viral genes are specifically selected. In some embodiments, the set of viral genes share a specific parameter. In some embodiments, the set of viral genes share a common trait. In some embodiments, the common trait shared by the set of viral genes is selected from the group consisting of: common gene structure, common temporal expression during a virus's life cycle, common function of the encoded proteins, common cellular localization of translation and common cellular localization of the encoded proteins. In some embodiments, coordinated expression comprises at least one of coordinated temporal expression, coordinated location of translation, coordinated location of expressed proteins, and coordinated rate of expression. In some embodiments, coordinated expression is coordinated temporal expression. In some embodiments, the temporal expression is during a virus's life cycle.

In some embodiments, gene structure refers to the number, size, and spacing of exons in the gene body. In some embodiments, gene structure refers to base pair motifs and structures within the gene body, such as GC repeats, CpG islands, AT rich region, or DNA/RNA/protein binding sites. In some embodiments, gene structure refers to elements within the gene that code for specific protein motifs, or functional regions. In some embodiments, genes with common gene structure are member of a particular gene or protein family.

As used herein, the term "temporal expression during a virus's life cycle", refers to a gene's expression occurring during a defined period in the life of a virus.

The terms "express" or "expression" as used herein refers to the biosynthesis of a product, including the transcription and/or translation of said gene product or a non-coding RNA. Thus, expression of a nucleic acid molecule may refer to transcription of the nucleic acid fragment (e.g., transcription resulting in mRNA or other functional RNA) and/or translation of RNA into a precursor or mature protein (polypeptide).

In some embodiments, the defined period is selected from the list consisting of: early in the virus life cycle, the intermediate period of the virus life cycle, and late in the virus life cycle. In some embodiments, early in the virus's life cycle is during the first 20 minutes after infection. In some embodiments, early in the virus's life cycle is during the first 15 minutes after infection. In some embodiments, early in the virus's life cycle is during the lysogenic portion of an infection. In some embodiments, early in the virus's life cycle is following entry into the host cell, but prior to replication. In some embodiments, early in the virus's life cycle is before nuclear export of viral mRNAs. In some embodiments, late in the virus's life cycle is during the last 15 minutes before lysis of the host cell. In some embodiments, late in the virus's life cycle is during the last 10 minutes before lysis of the host cell. In some embodiments, late in the virus's life cycle is during the lysis portion of an infection. In some embodiments, late in the virus's life cycle is after replication. In some embodiments, late in the virus's life cycle is after nuclear export of viral mRNAs. One skilled in the art, will be able to determine the different stages of a virus's life cycle. More than one way of dividing a specific virus's life cycle may be useful for determining the set of genes to be used for determining codon frequency.

The terms "viral life cycle" and "virus's life cycle" are synonymous and interchangeable, and as used herein refer to the period spanning entry of a virus into a host cell, stably residence within the host (lysogeny), and a lytic phase during which the virus produces progeny viral particles, and lyses and kills the host cell. In some embodiments, the virus is bacteriophage Lambda, the viral life cycle is approximately 25 minutes long, the early period of the viral life cycle is the first 15 minutes and the late period of the viral life cycle is the last 10 minutes.

As used herein, the term "host cell" refers to any cell into which a virus has been introduced. In some embodiments, the host cell is a bacterial cell. In some embodiments, the host cell is an *E. coli* cell. In some embodiments, the host cell is a mammalian cell. In some embodiments, the host cell is a human cell.

As used herein, the term "common cellular localization of translation" refers to the mRNA from a group of genes all being translated at the same location. Translation, generally occurs in the cytoplasm, but can also occur in the nucleus or at specific locations within the cytoplasm. Non-limiting examples of common cellular localization of translation are translation at the ER, perinuclear translation, and translation near the plasma membrane.

As used herein, the term "common function of the encoded proteins" refers to the proteins for which a group of genes code having a common cellular function. Methods of discerning protein function are well known to one skilled in the art and protein function can be found using several commercially available websites and softwares. Examples of such are not limited to but include: the gene ontology consortium (www.geneontology.org), the Ingenuity Pathway Analysis (www.ingenuity.com), Uniprot (www.uniprot.org), and PredictProtein (www.predictprotein.org).

In some embodiments, the common function is viral structure. In some embodiments, the common function is transcriptional regulation. In some embodiments, the common function is lysongeny.

As used herein, the term "common cellular localization of the encoded proteins" refers to the proteins for which a group of genes code having a common localization in the cell. In some embodiments, the common localization is in the plasma membrane, in the nucleus, in the cytosol, in the mitochondria, in the endoplasmic reticulum, in the Golgi apparatus, or in the nuclear membrane. Each possibility represents a separate embodiment of the present invention.

In some embodiments, the synonymous codon has a parameter that results in faster translation in a particular cellular context relative to the at least one codon that has been substituted. In some embodiments, a plurality of codons having synonymous codons with faster translation rates in a particular cellular context have been substituted. In some embodiments, the at least one codon is substituted to the fastest translating synonymous codon in a particular cellular context.

In some embodiments, faster translation in a particular cellular context is at least %, 5%, 10%, 15%, 20%, 25%, 30%, 35%, 40%, 45%, 50%, 55%, 60%, 65%, 70%, 75%, 80%, 85%, 90%, 95%, 100%, 150%, 200%, 250%, 300%, 350%, 400%, 450%, 500%, 1000%, or 10000% faster as compared to the at least one codon that has been replaced.

In some embodiments, optimizing a codon increases translational efficiency of the nucleic acid sequence in a particular cellular context. In some embodiments, optimizing a codon increases expression of a polypeptide encoded by the nucleic acid sequence in a particular cellular context. In some embodiments, deoptimizing a codon decreases translational efficiency of the nucleic acid sequence in a particular cellular context. In some embodiments, deoptimizing a codon decreases expression of a polypeptide encoded by the nucleic acid sequence in a particular cellular context.

In some embodiments, optimizing the codons increases expression by at least 1%, 5%, 10%, 15%, 20%, 25%, 30%, 35%, 40%, 45%, 50%, 55%, 60%, 65%, 70%, 75%, 80%, 85%, 90%, 95%, 100%, 150%, 200%, 250%, 300%, 350%, 400%, 450%, 500%, 1000%, or 10000% relative to expression of the target sequence. Each possibility represents a separate embodiment of the present invention.

In some embodiments, the synonymous codon has a parameter that results in slower translation in a particular cellular context relative to the at least one codon that has been substituted. In some embodiments, a plurality of codons having synonymous codons with slower translation rates in a particular cellular context have been substituted. In some embodiments, the at least one codon is substituted to the slowest translating synonymous codon in a particular cellular context.

In some embodiments, slower translation in a particular cellular context is at least %, 5%, 10%, 15%, 20%, 25%, 30%, 35%, 40%, 45%, 50%, 55%, 60%, 65%, 70%, 75%, 80%, 85%, 90%, 95%, 100%, 150%, 200%, 250%, 300%, 350%, 400%, 450%, 500%, 1000%, or 10000% slower as compared to the at least one codon that has been replaced.

In some embodiments, deoptimizing the codons decreases expression by at least 1%, 5%, 10%, 15%, 20%, 25%, 30%, 35%, 40%, 45%, 50%, 55%, 60%, 65%, 70%, 75%, 80%, 85%, 90%, 95%, 100%, 150%, 200%, 250%, 300%, 350%, 400%, 450%, 500%, 1000% or 10000% relative to expression of the target sequence. Each possibility represents a separate embodiment of the present invention. In some embodiments, deoptimizing the codons decreases expression to zero. In some embodiments, deoptimizing the codons abolishes, or completely removes expression of the protein.

Viral Compositions

By another aspect, there is provided a modified virus, comprising anyone of the above described nucleic acid molecules. In some embodiments, the virus is a virulent virus. In some embodiments, the virus infects mammals. In some embodiments, the virus infects humans.

In some embodiments, the modified virus is for use in creating a vaccine. In some embodiments, the modified virus is for use as an oncolytic virus. In some embodiments, the modified virus is for use as a carrier for a therapeutic agent.

In some embodiments, the modified virus has a coding sequence that is an essential viral sequence expressed during a defined period of a virus's life cycle and the set of genes used for assessing the frequency of codons is a plurality of viral genes expressed during the defined period of a virus's life cycle. In some embodiments, the modified virus has a coding sequence that is part of an essential viral sequence.

In some embodiments, the essential viral gene is required for viral replication. In some embodiments, the essential viral gene is a structural protein. In some embodiments, the essential viral gene is required for lysis of a host cell. In some embodiments, the essential viral gene is a capsid. In some embodiments, the essential viral gene is an enzyme. In some embodiments, the essential viral gene is reverse transcriptase. In some embodiments, the essential viral gene is RNA dependent RNA polymerase (RDRP).

By another aspect, there is provided an attenuated form of a virus, comprising a nucleic acid molecule with at least one codon substituted for a less frequent codon, and wherein the coding sequence is an essential viral sequence endogenously expressed during a defined period of a virus's life cycle, said set of genes used for calculating codon frequency is a plurality of viral genes expressed during the same defined period of the virus's life cycle and wherein the virus is devoid of the endogenous viral sequence.

In some embodiments, the viral genome is altered such that the endogenous viral sequence is completely absent. In some embodiments, the viral genome is altered such that the endogenous viral sequence is not expressed. General methods for disruption of the genome as well as general methods in molecular and cellular biochemistry can be found in such standard textbooks as Molecular Cloning: A Laboratory Manual, 3rd Ed. (Sambrook et al., HaRBor Laboratory Press 2001); Short Protocols in MolecularBiology, 4th Ed. (Ausubel et al. eds., John Wiley & Sons 1999); Protein Methods (Bollag et al., John Wiley & Sons 1996); Nonviral Vectors for Gene Therapy (Wagner et al, eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle &. Griffiths, John Wiley & Sons 1998).

Generally, modifications are performed to a point at which the virus can still be grown in some cell lines (including lines specifically engineered to be permissive for a particular virus), but where the virus is avirulent in a normal animal or human. Such avirulent viruses are excellent candidates for either a killed or live vaccine since they encode exactly the same proteins as the fully virulent virus and accordingly provoke exactly the same immune response as the fully virulent virus. In addition, the process described herein offers the prospect for fine tuning the level of attenuation; that is, it provides the capacity to design synthetic viral genomes whose codon selection is deoptimized to a roughly predictable extent. Design, synthesis, and production of viral particles is achievable in a timeframe of weeks once the genome sequence is known, which has important advantages for the production of vaccines in potential emergencies. Furthermore, the attenuated viruses are expected to have virtually no potential to revert to virulence because of the extremely large numbers of deleterious nucleotide changes involved. This method may be generally applicable to a wide range of viruses, requiring only knowledge of the viral genome sequence and a reverse genetics system for any particular virus.

Methods of modifying viral genomes are known in the art and employ molecular biology techniques such as in vitro transcription, reverse transcription, polymerase chain reaction, restriction digestion, cloning etc.

Detailed descriptions of conventional methods, such as those employed in the construction of recombinant plasmids, transfection of host cells with viral constructs, polymerase chain reaction (PCR), and immunological techniques can be obtained from numerous publications, including Sambrook et al. (1989) and Coligan et al. (1994).

When the viral genome is an RNA genome, they may be isolated from virions or from infected cells, converted to DNA ("cDNA") by the enzyme reverse transcriptase, possibly modified as desired, and reverted, usually via the RNA intermediate, back into infectious viral particles. Most commonly, the entire cDNA copy of the genome is cloned immediately downstream of a phage T7 RNA polymerase promoter that allows the in vitro synthesis of genome RNA, which is then transfected into cells for generation of virus (van der Wert, et al., 1986). Alternatively, the same DNA plasmid may be transfected into cells expressing the T7 RNA polymerase in the cytoplasm.

In certain embodiments, the modifying is achieved by de novo synthesis of DNA containing the synonymous codons and substitution of the corresponding region of the genome with the synthesized DNA. In further embodiments, the entire genome is substituted with the synthesized DNA. In still further embodiments, a portion of the genome is substituted with the synthesized DNA.

Vaccine Compositions

By another aspect, there is provided a vaccine composition for inducing a protective immune response in a subject, the vaccine composition comprising one of the above described attenuated viruses and a pharmaceutically acceptable carrier or adjuvant. In some embodiments, the composition is an immunogenic composition.

The terms "vaccine composition" and "vaccine" as used herein are interchangeable and refers to a product, the administration of which is intended to elicit an immune response that is capable of preventing and/or lessening the severity of one or more viral infections.

It should be understood that an attenuated virus of the invention, where used to elicit a protective immune response (i.e. immunize) in a subject or to prevent a subject from becoming afflicted with a virus-associated disease, is administered to the subject in the form of a composition additionally comprising a pharmaceutically acceptable carrier. As used herein, the terms "carrier" and "adjuvant" refer to any component of a pharmaceutical composition that is not the active agent. As used herein, the term "pharmaceutically acceptable carrier" refers to non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations. Some non-limiting examples of substances which can serve as a carrier herein include sugar, starch, cellulose and its derivatives, powered tragacanth, malt, gelatin, talc, stearic acid, magnesium stearate, calcium sulfate, vegetable oils, polyols, alginic acid, pyrogen-free water, isotonic saline, phosphate buffer solutions, cocoa butter (suppository base), emulsifier as well as other non-toxic pharmaceutically compatible substances used in other pharmaceutical formulations. Wetting agents and lubricants such as sodium lauryl sulfate, as well as coloring agents, flavoring agents, excipients, stabilizers, antioxidants, and preservatives may also be present. Any non-toxic, inert, and effective carrier may be used to formulate the compositions contemplated herein. Suitable pharmaceutically acceptable carriers, excipients, and diluents in this regard are well known to those of skill in the art, such as those described in The Merck Index, Thirteenth Edition, Budavari et al., Eds., Merck & Co., Inc., Rahway, N.J. (2001); the CTFA (Cosmetic, Toiletry, and Fragrance Association) International Cosmetic Ingredient Dictionary and Handbook, Tenth Edition (2004); and the "Inactive Ingredient Guide," U.S. Food and Drug Administration (FDA) Center for Drug Evaluation and Research (CDER) Office of Management, the contents of all of which are hereby incorporated by reference in their entirety. Examples of pharmaceutically acceptable excipients, carriers and diluents useful in the present compositions include distilled water, physiological saline, Ringer's solution, dextrose solution, Hank's solution, and DMSO. These additional inactive components, as well as effective formulations and administration procedures, are well known in the art and are described in standard textbooks, such as Goodman and Gillman's: The Pharmacological Bases of Therapeutics, 8th Ed., Gilman et al. Eds. Pergamon Press (1990); Remington's Pharmaceutical Sciences, 18th Ed., Mack Publishing Co., Easton, Pa. (1990); and Remington: The Science and Practice of Pharmacy, 21st Ed., Lippincott Williams & Wilkins, Philadelphia, Pa., (2005), each of which is incorporated by reference herein in its entirety. The presently described composition may also be contained in artificially created structures such as liposomes, ISCOMS, slow-releasing particles, and other vehicles which increase the half-life of the peptides or polypeptides in serum. Liposomes include emulsions, foams, micelies, insoluble monolayers, liquid crystals, phospholipid dispersions, lamellar layers and the like. Liposomes for use with the presently described peptides are formed from standard vesicle-forming lipids which generally include neutral and negatively charged phospholipids and a sterol, such as cholesterol. The selection of lipids is generally determined by considerations such as liposome size and stability in the blood. A variety of methods are available for preparing liposomes as reviewed, for example, by Coligan, J. E. et al, Current Protocols in Protein Science, 1999, John Wiley & Sons, Inc., New York, and see also U.S. Pat. Nos. 4,235,871, 4,501,728, 4,837,028, and 5,019,369.

The carrier may comprise, in total, from about 0.1% to about 99.99999% by weight of the pharmaceutical compositions presented herein.

By another aspect, there is provided a method for vaccinating a subject at risk of viral infection, the method comprising, administering to said subject the vaccine composition described above.

The term "subject at risk of viral infection" includes but is not limited to a subject that due a likelihood of future exposure to a virus, future exposure to an individual or animal infected with the virus, or future exposure to biological mater infected with the virus, is at a higher risk than the general population of contracting the virus.

Methods of Production

By another aspect, there is provided a method for producing a nucleic acid molecule optimized for expression in a particular cellular context, the method comprising:

a) selecting a coding sequence,
b) selecting a reference set of genes expressed in a particular cellular context,
c) for each codon of said coding sequence, computing a parameter that effects translation rate for said codon and its synonymous codons over all sequences in the reference set, and
d) substituting at least one codon of said coding sequence with a synonymous codon th a faster rate of translation, thereby producing a nucleic acid molecule optimized for expression in a particular cellular context.

In some embodiments, the computing of average relative frequency comprises, a. selecting a reference set (R) of viral genes expressed during a defined period,
b. for each amino acid coded for by said coding sequence (A), computing a relative frequency of synonymous codons in each reference sequence k:

$$F^k(C_{A,j}) = \frac{q_{A,j}}{\sum_{j=1}^{m} q_{A,j}}, \sum_{j=1}^{m} F(C_{A,j}) = 1$$

(where $\{C_{A,j}\}_{j=1}^{m}$ are m synonymous codons of said amino acid A; $q_{A,j}$ is the number of appearances of codon $C_{A,j}$ in the processed sequence; the superscript k stands for "the k-th reference sequence)

c. for each amino acid (A), computing an average relative frequency of its synonymous codons over all sequences in R:

$$F(C_{A,j}) = \frac{1}{|R|} \sum_{k=1}^{|R|} F^k(C_{A,j})$$

(where |R| is the number of reference sequences)

In some embodiments, substituting a codon with a faster rate of translation comprises, a. for each codon of said coding sequence ($C_{A,i}$) replacing $C_{A,i}$ with a synonymous codon $C_{A,j}$ according to $$C_{A,j} = \underset{C_{A,k}}{\operatorname{argmax}} F(C_{A,k}).$$

In some embodiments, optimizing the codons comprises the steps of:

a. selecting a reference set (R) of viral genes expressed during a defined period,
b. for each amino acid coded for by said coding sequence (A), computing a relative frequency of synonymous codons in each reference sequence k:

$$F^k(C_{A,j}) = \frac{q_{A,j}}{\sum_{j=1}^{m} q_{A,j}}, \sum_{j=1}^{m} F(C_{A,j}) = 1$$

c. for each amino acid (A), computing an average relative frequency of its synonymous codons over all sequences in R:

$$F(C_{A,j}) = \frac{1}{|R|} \sum_{k=1}^{|R|} F^k(C_{A,j})$$

and
d. for each codon of said target sequence ($C_{A,i}$) replacing $C_{A,i}$ with a synonymous codon $C_{A,j}$ according to $$C_{A,j} = \underset{C_{A,k}}{\operatorname{argmax}} F(C_{A,k}).$$

The statistical modeling, algorithm calculation and other processing found in the instant application can be carried out using software/programming languages such as is known to one of ordinary skill in the art. Among many widely available software packages/programming languages, are Matlab, C, and Python, along with many others that have been used for the calculations found in the present application.

In some embodiments, optimizing said codons comprises optimizing the expression levels of the wildtype sequence s with respect to the codons Typical Decoding Rate (TDR) basing on available ribosomal profiling data. To estimate TDR, a statistical mode, which takes into consideration the skewed nature of the ribose read count distribution can be used. This model describes the readcount histogram of each codon as an output of a random variable which is a sum of two random variables: a normal and an exponential variable. Thus, the distribution of this new random variable includes three parameters and is called EMG distribution. In this model, the typical codon decoding time was described by the normal distribution with two parameters: mean ($\mu$) and standard deviation $\sigma$; the $\mu$ parameter represents the location of the mean of the theoretical Gaussian component that should be obtained if there are no phenomena such as pauses/biases/ribosomal traffic jams; $\sigma$ represents the width of the Gaussian component. The exponential distribution has one parameter $\lambda$ which represents the skewness of the readcount distribution due to reasons such as ribosomal jamming caused by codons with different decoding times, extreme pauses, incomplete halting of the ribosomes, biases in the experiment, etc. The EMG is defined as follows:

$$f(x; \mu, \sigma, \lambda) = \frac{\lambda}{2} e^{\frac{\lambda}{2}(2\mu + \lambda\sigma^2 - 2x)} \operatorname{erfc}\left(\frac{\mu + \lambda\sigma^2 - x}{\sqrt{2}\sigma}\right),$$

$$\operatorname{erfc}(x) = 1 - \operatorname{erf}(x) = \int_x^\infty e^{-t^2} dt$$

These three parameters may be estimated for each codon at different replication stages based on time dependent ribosome profiling data by fitting the suggested model to the given read count distribution (e.g. using the maximal likelihood estimation or any other algorithm).

$$\frac{1}{\mu}$$

is defined to be the Typical Decoding Rate (TDR) of each codon.

By another aspect, there is provided a method for producing a nucleic acid molecule deoptimized for expression in a particular cellular context, the method comprising:

a. selecting a coding sequence,
b. selecting a reference set of genes expressed in a particular cellular context,
c. for each codon of said coding sequence, computing a parameter that effects translation rate for said codon and its synonymous codons over all sequences in the reference set, and
d. substituting at least one codon of said coding sequence with a synonymous codon with a slower rate of translation, thereby producing a nucleic acid molecule optimized for expression in a particular cellular context.

In some embodiments, substituting a codon with a slower rate of translation comprises,
b. for each codon of said target sequence ($C_{A,i}$) replacing $C_{A,i}$ with a synonymous codon $C_{A,j}$ according to $$C_{A,j} = \underset{C_{A,k}}{\operatorname{argmin}} F(C_{A,k}).$$

In some embodiments, deoptimizing said codons comprises the steps of:
a. selecting a reference set (R) of viral genes expressed during said defined period,
b. for each amino acid coded for by said coding sequence (A), computing a relative frequency of synonymous codons in each reference sequence k:

$$F^k(C_{A,j}) = \frac{q_{A,j}}{\sum_{j=1}^m q_{A,j}}, \quad \sum_{j=1}^m F(C_{A,j}) = 1$$

(where $\{C_{A,j}\}_{j=1}^m$ are m synonymous codons of said amino acid A; $q_{A,j}$ is the number of appearances of codon $C_{A,j}$ in the processed sequence; the superscript k stands for "the k-th reference sequence)
c. for each amino acid (A), computing an average relative frequency of its synonymous codons over all sequences in R:

$$F(C_{A,j}) = \frac{1}{|R|} \sum_{k=1}^{|R|} F^k(C_{A,j})$$

and
d. for each codon of said target sequence ($C_{A,i}$) rreplacing $C_{A,i}$ with a synonymous codon $C_{A,j}$ according to $$C_{A,j} = \underset{C_{A,k}}{\operatorname{argmin}} F(C_{A,k}).$$

In some embodiments, the deoptitnization comprises creating a gradient library of deoptimized variants of the coding sequence with different levels of deoptimization where codon of said target sequence ($C_{A,i}$) is replaced with a synonymous codon $C_{A,j}^{r(k)}$ $$C_{A,j}^{r(k)} : F(C_{A,i}) < F\left(C_{A,j}^{r(k)}\right) < \max_{C_{A,k}} F(C_{A,k})$$

(where $C_{A,j}^{r(k)}$ is a synonymous codon of said amino acid A of frequency rank k in the reference set [most frequent/second most frequent/ . . . /k-th most frequent . . . etc])

In these embodiments' codons of different ranks: the second, third, etc. less frequent synonymous codon in the reference set would he selected to replace the codon of the target sequence In some embodiments, the gradient library also include Cartesian products of codons with different ranks of relative frequencies:

$$A_1 \times \ldots \times A_n = \{(C_1^{r(1)}, \ldots, C_n^{r(n)}): C_i^{r(i)} \in A_i\}$$

$C_i^{r(k)}$ is a codon coding for $A_i$ of some frequency rank r(k) (most frequent/second most frequent/third most frequent etc.) with respect to the reference set.

In some embodiments, deoptimizing said codons comprises replacing the codons of the coding sequence with synonymous codons chosen according to the "inverse rank" rule: if the wildtype codon $C_{A,i}$ is the most frequent codon in the reference set it is replaced by the less frequent synonymous codon $C_{A,j}$; if it is the second most frequent it is replaced with the second less frequent; if it is the third most frequent it is replaced with the third less frequent, . . . , the second less frequent is replaced by the second most frequent; the less frequent is replaced by the most frequent.

I.e.: if $C_{A,1}, \ldots, C_{A,m}$ are synonymous codons coding for amino acid A arranged in a descending order according to their relative frequencies in the reference set: $F(C_{A,1}) \geq F(C_{A,2}) \geq \ldots \geq F(C_{a,m})$, then the codon replacement rule (Q) is defined as follows:

$$Q(C_{A,1}) = C_{A,m}; Q(C_{A,2}) = C_{A,m-1}; \ldots; Q(C_{A,m}) = C_{A,1}$$

In some embodiments, the particular cellular context is selected from the group consisting of: a specific period of a cell's life cycle, during cellular division, during cellular stress, during apoptosis, during viral infection, or during viral lysogeny of the cell. It should be understood, that any change in cellular context may result in a change in the tRNA pool. In some embodiments, the particular cellular context is a pre-determined cellular context.

In some embodiments, the above recited methods further comprise confirming that the nucleic acid or virus has been optimized, deoptimized or modified. In some embodiments, confirming optimization, deoptimization or modification comprises expressing the selected sequence and the substituted sequence in the virus, measuring protein expression during the defined time period of the virus's life cycle and comparing the protein levels produced by the selected sequence and substituted sequence. Expression within the virus and measuring protein expression are routine laboratory practices and would be well known to one skilled in the art. Detailed descriptions of these methods can be found in the publications previously enumerated in this application.

By another aspect, there is provided a method of producing a modified virus, the method comprising:
a. selecting an endogenous viral sequence,
b. selecting a reference set of viral genes that share a common trait,
c. for each codon of said viral sequence, computing a parameter that effects translation rate for said codon and its synonymous codons over all sequences in the reference set,
d. substituting at least one codon of said viral sequence with a synonymous codon with a different translation rate, thereby producing a reengineered viral sequence, and e. replacing the endogenous viral sequence with the reengineered viral sequence, thereby producing a modified virus.

By another aspect, there is provided a method for producing an attenuated virus the method comprising the above method for producing a modified virus wherein:
a) said viral sequence is an essential viral sequence, and
b) said synonymous codon with a different translation rate has a slower translation rate, thereby producing an attenuated virus.

Computer Program Product

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device having instructions recorded thereon, and any suitable combination of the foregoing. A computer readable storage medium, as used herein, is not to be construed as being transitory signals per se, such as radio waves or other freely, propagating electromagnetic waves, electromagnetic waves propagating through a waveguide or other transmission media (e.g., light pulses passing through a fiber-optic cable), or electrical signals transmitted through a wire. Rather, the computer readable storage medium is a non-transient (i.e., not-volatile) medium.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry, including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention may be described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about". The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs.

It is noted that as used herein and in the appended claims, the singular forms "a," "an," and "the" include plural referents unless the context clearly dictates otherwise. Thus, for example, reference to "a polynucleotide" includes a plurality of such polynucleotides and reference to "the polypeptide" includes reference to one or more polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Material and Methods

Data. Ribosome profiling was applied to the process of lytic growth of Bacteriophage lambda as has been shown previously (Liu X Q, et al., Proceedings of the National Academy of Sciences of the United States of America, 2013, 110:11928-11933). Temperature induction of the classic cI857 repressor mutant of Bacteriophage lambda was used in the lysogen of Escherichia coli (E. coli) MG1655 to synchronize the lytic process, sampling the lysogen and control non-lysogen both before and 2, 5, 10, and 20 min after shifting the temperature from 32° C. to 42° C.

Transcript sequences were obtained from EnsEMBL for E. coli (K-12 MG1655 release 121, accessed 28/07/15) and from NCBI for the lambda phage (J02459, accessed 07/12/15).

There were 4319 genes of E. coli and 66 genes of lambda phage in the obtained sequences.

Ribo-seq reads mapping. Ribosome footprint sequences were obtained from previously published results (Liu X Q, et al., Proceedings of the National Academy of Sciences of the United States of America, 2013, 110:11928-11933) (GSE47509, induction 0-20min). The poly-A adaptors were trimmed from the reads using the Cutadapt program (version 1.8.3), and the Bowtie program (version 1.1.1) was used to map them to the E. coli-lambda transcriptome. In the first phase, reads that mapped to rRNA and tRNA sequences with Bowtie parameters '-n 2 -seedlen 23 -k 1 --norc' were discarded. In the second phase, the remaining reads were mapped to the transcriptome with Bowtie parameters '-v 2 -a --strata --best --norc -m 200'. Alignments were extended to their maximal length by comparing the polyA adaptor with the aligned transcript until reaching the maximal allowed error (2 mismatches across the read, with 3'-end mismatches avoided). Reads were either longer than 31 nucleotides (nt) or shorter than 21 nt. Unique alignments were first assigned to the ribosome occupancy profiles. For multiple alignments, the best alignments in terms of number of mismatches were kept. Then, multiple aligned reads were distributed between locations according to the distribution of unique ribosomal reads in the respective surrounding regions. To this end, a 100-nt window was used to compute the read count density $RCD_i$ (total read counts in the window divided by length, based on unique reads) in vicinity of the M multiple aligned positions in the transcriptome, and the fraction of a read assigned to each position was $RCD_i/\Sigma_{j=1}^{M} RCD_j$. The location of the A-site was approximated by an 11-nt shift from the 5' end of the aligned read. This shift maximized the correlation between MTDR (described below) and the observed read densities per E. coli gene.

Randomization Models

Two randomization models were considered:
1. To preserve both the amino acids order and content, and the frequencies distribution of 16 possible pairs of adjacent nucleotides (di-nucleotides) a model based on a multivariate Boltzmann sampling scheme was used. This model was initially introduced in the context of enumerative combinatorics and has been used previously for studying other viruses. The original source code was used and can be found at http://csb.cs.mcgill.ca/sparcs.
2. To preserve both the amino acids order and content and the codon usage bias synonymous positions in codon sequences were randomly permuted.

Synonymous Codon Usage Analysis

Synonymous codon composition of a coding sequence was represented by a 61-dimensional vector of relative synonymous codons frequencies (RSCF) of each one of 61 coding codons (stop codons are excluded):

$$RSCF = (RSCF[1], \ldots, RSCF[61])$$

$$RSCF[i] = \frac{q_i}{\sum_{j \in syn[i]} q_j}, \quad \sum_{j \in syn[i]} RSCF[j] = 1$$

where $q_i$ is the number of appearances of codon i in a sequence, syn[i] subset of indexes in RSCF pointing at codons synonymous to codon i.

Clustering analysis was performed on RSCF vectors of each viral coding sequence. In order to exclude biases due to a possible absence of specific amino acids in specific sequences (missing amino acids), the relative synonymous frequency of a codon corresponding to a missing amino acid was set to the average relative synonymous frequency of this codon over all sequences in which at least one such amino acid is present.

Each viral sequence was assigned a group label corresponding to its temporal expression stage (Early/Late) (according to the classification known in the literature). The tendency of sequences to cluster according to the codons usage in two different clusters corresponding to their temporal expression stages (early/late) was measured using the Davies-Bouldin score (DBS). This score is based on a ratio of within-cluster and between-cluster distances and is defined as:

$$DB = \frac{1}{k}\sum_{i=1}^{k} \max_{j \neq i}\{D_{ij}\}, D_{ij} = \frac{\overline{d}_i + \overline{d}_j}{d_{ij}}$$

Where k—is the number of evaluated clusters, $D_{ij}$ is the within-to-between cluster distance ratio for the i-th and j-th clusters; $\overline{d}_i$ is the average Euclidian distance between each point in the i-th cluster and the centroid of the i-th cluster; $\overline{d}_j$ is the average Euclidian distance between each point in the j-th cluster and the centroid of the j-th cluster; $d_{ij}$ is the Euclidean distance between the centroids of the ith and jth clusters. The maximum value of $D_{ij}$ represents the worst-case within-to-between cluster ratio for cluster i. The optimal clustering solution has the smallest Davies-Bouldin score value.

The significance of cluster separation was assessed by comparing the DBS of the wildtype sequences to the randomized scores obtained from 100 permutations of gene group labels (early or late).

In order to visualize the clustering, a principal component analysis (PCA) was applied to project the RSCF vectors to a plane spanned by their first two principal components. In order to visualize the separation between clusters a maximum margin separation line—a line for which the distance between it and the nearest point from either of the groups is maximized, was calculated and plotted.

In the same manner, analysis of clustering between early and late viral groups and a set of top 50 host genes with the highest protein abundance can be performed Codons Composition Analysis.

Codons composition of a coding sequence was represented by codons relative frequency vector. In this 64-dimensional vector each entry i corresponds to one specific codon and contains its relative frequency with respect to codon usage in some reference set of coding sequences (e.g. *E. coli* coding regions, bacteriophage early genes, bacteriophage late genes, etc.):

$$w_i = \frac{f_i}{\max(f_j)}$$

defined as a ratio of the frequency $f_i$ of this codon in the coding sequence, to that of the most abundant synonymous codon for the same amino acidmax ($f_j$) in the reference set (i and j are indexes of synonymous codons for amino acid In this study we used a few references sets: The *E. coli*, bacteriophage lambda genes, bacteriophage early genes, bacteriophage late genes, each coding region separately, etc. (FIG. 2). Note that by computing a geometric average of wi we obtain a Codon Adaptation Index (CAI).

The clustering analysis was performed on the codons relative frequency vectors of each viral coding sequence (with all viral genes as a reference set). A principal component analysis was applied to project the r vectors to a plane spanned by their first two principal components. Two different clusters separating between early and late genes were distinguished (FIG. 2A) using the Davies-Bouldin score. The significance of clusters separation was assessed by comparing this score to the randomized scores obtained from 100 permutations of gene group labels (early or late).

The similarity/distance of codons usage between two coding sequences was calculated using codons usage frequency distance (CUFD) measure. CUFD measures similarity between genes in terms of codon and amino acid usage. Codon usage frequency vectors were computed by counting all appearances ni of a codon i in the ORF, and dividing by the total codon count:

$$c_i = \frac{n_i}{\sum_{j \in AA} n_i}; \sum_{i=1}^{64} c_i = 1$$

The CUFD between genes was computed using the Endres-Schindelin metric for probability distributions. Given the frequency vectors of a pair of genes p and q, the CUF distance/similarity between them is given by:

$$d_{KL}(p, q) = \sum_{i=1}^{64} \log \frac{p_i}{q_i} p_i$$

$$m \equiv \frac{1}{2}(p + q)$$

$$d_{ES} = \sqrt{d_{KL}(p, m) + d_{KL}(q, m)}$$

where dKL is the Kullback-Leibler divergence. Larger values related to less similarity/larger distance.

The tRNA Adaptation Index (tAI)

tAI quantifies the adaptation of a coding region to the tRNA pool. Let tCGNi j be the copy number of the j-th anti-codon that recognizes the i-th codon and let Si j be the selective constraint of the codon-anti-codon coupling efficiency. The S vector [sI:U, sG:C, sU:A, sC:G, sG:U, sI:C, sI:A, sU:G, sL:A] was defined for *E. coli* as [0, 0, 0, 0, 1, 0.25, 0.81, 1, 0.71] according to optimization performed previously (Sabi R, et al., DNA Research, 2014, 21:511-525). Thus, the absolute adaptiveness value of a codon of type i (1≤i≤61; stop codons are excluded) to the tRNA pool is defined by:

$$W_i = \sum_{j=1}^{n_i} (1 - S_{ij}) tCGN_{ij}$$

For each amino acid, the weight of each of its codons, is computed as the ratio between the absolute adaptiveness value of the codon and the maximal absolute adaptiveness value of the synonymous codons for that amino acid:

$$w_i = \frac{W_i}{\max_{j \in syn[i]} W_j}$$

where $W_i$ is the absolute adaptiveness of codon i in a sequence, syn[i] is a subset of indexes in pointing at codons synonymous to codon i. $w_i$ takes values from 0 (not adapted) to 1 (maximally adapted). If the weight value is zero a value of 0.5 is used tAI is the geometric mean of $w_i$ (relative codon-tRNA adaptation) over codons of a coding sequence.

Ribosome Profiling Data Normalization

Ribosome profiles for *E. coli* and Bacteriophage Lambda expressed genes were reconstructed. The ribosome profiling method produces ribosome footprint counts that are proportional to the time spent in decoding each codon of all translated transcripts in a genome, at single nucleotide resolution. To avoid analyzing ribosomal profiles of genes with many missing read counts (RCs) that may result in a non-reliable estimation of the local ribosome density, genes profiles with fewer than 30 percent non-zero read counts were further filtered. The first and last 20 codons were excluded when determining these thresholds or when calculating the average RCs per ORF. To enable comparison and analysis of RCs of codons of the same type originating from different genes, RCs of each codon were normalized by the average RCs of each gene; this normalization controls for possible different mRNA levels and initiation rates of different genes. To prevent biasing the average with codons containing less than one RC, they were excluded from the analysis. Therefore, this normalization enables measuring the relative time a ribosome spends translating each codon in a specific gene relative to other codons in it, while considering the total number of codons in the gene, resulting in its normalized footprint count (NFC):

$$NFC_j = \frac{RC_j}{\frac{1}{J-40}(RC_{21} + RC_{22} + \ldots + RC_{J-20})}$$

$$j = 21 \ldots J - 20$$

Where J is the number of codons in the gene and j is the index of a codon.

At the first step, a histogram of NFC for each codon was generated. Each NFC distribution describes the probability (y-axis) of observing each of the codon's NFC values (x-axis) in the ORFs of the analyzed organism.

Codon Typical Decoding Rate (TDR)

To estimate the typical decoding time of each codon based on NFC distributions, we used a novel statistical model (Dana A et al., Nucleic Acids Res., 2014), which takes into consideration the skewed nature of the NFC distribution. The aim is to describe the NFC histogram of each codon as an output of a random variable which is a sum of two random variables: a normal and an exponential variable. Thus, the distribution of this new random variable includes three parameters, and is called EMG distribution. In this model, the typical codon decoding time was described by the normal distribution with two parameters: mean ($\mu$) and standard deviation ($\sigma$); the $\mu$ parameter represents the location of the mean of the theoretical Gaussian component that should be obtained if there are no phenomena such as pauses/biases/ribosomal traffic jams; $\sigma$ represents the width of the Gaussian component. The exponential distribution has one parameter $\lambda$, which represents the skewness of the NFC distribution due to reasons such as ribosomal jamming caused by codons with different decoding times, extreme pauses, incomplete halting of the ribosomes, biases in the experiment, etc. The EMG is defined as follows:

$$f(x; \mu, \sigma, \lambda) = \frac{\lambda}{2} e^{\frac{\lambda}{2}(2\mu + \lambda\sigma^2 - 2x)} erfc\left(\frac{\mu + \lambda\sigma^2 - x}{\sqrt{2}\sigma}\right),$$

$$erfc(x) = 1 - erf(x) = \int_x^\infty e^{-t^2} dt$$

Maximum likelihood criterion was used to estimate these three parameters for each codon based on *E. coli* ribosome profiling data by fitting the suggested model to the NFC distribution.

$$\frac{1}{\mu}$$

was defined to be the Typical Decoding Rate (TDR) of each codon.

In order to optimize the TDR to *E. coli*'s read counts in every time condition; outliers were removed from the NFC distribution of each codon in the following way: for every codon (in every time condition), and for each NFCi point related to the codon, we calculated the probability (Pi) to see value larger or equal to NFCi based on the pdf fitted to the codon (EMG distribution). Let Ni denote the number of measurements of the codon NFC based on the data; points in which the result of $p_i * N_i$ was lower than 0.001 were removed.

Mean Typical Decoding Rate (MTDR).

A measure which estimates the translation elongation efficiency of the entire gene as a geometric average of typical decoding rates of its codons:

$$MTDR = e^{\frac{1}{L}\sum_{l=1}^{L} \log(TDR_i(l))}$$

where i is an index of a codon and L is the gene length in codon unit.

Relative Translation Elongation Efficiency Coefficient (RTEC).

Quantifies the relative differences in mean MTDR values of early and late gene.

$$RTEC = \frac{(\text{mean } MTDR_E - \text{mean } MTDR_L)}{(\text{mean } MTDR_E + \text{mean } MTDR_L)}$$

where E and L signify early and late genes.

Folding Energy Analysis

Minimum free folding energy (MFE) is a thermodynamic energy involved in maintaining a secondary structure available to perform physical work whilst being released, and thus is characterized by nonpositive values. mRNA secondary structure is believed to be in the most stable conformation when minimum amount of free energy is exerted (the MFE obtains the most negative value). The local WE-profiles were constructed by applying a 39 nt length sliding window to a genomic sequence: in each step the WE of a local subsequence enclosed by the corresponding window was calculated by Vienna (v. 2.1.9) package RNAfold function with default parameters. This function predicts the MFE and the associated secondary structure for the input RNA sequence using a dynamic programming based on the thermodynamic nearest-neighbor approach (the Zucker algorithm).

First, all the genes in the bacteriophage genome were lined up according to their start codon and WE-profiles were calculated for each coding region together with 40-nt up-stream the start codon sequence from the 50 UTR. Then, all the genes in the genome were lined up according to their end codon and MFE profiles were calculated for each coding region together with 40-nt down-stream the end codon from the 30 UTR.

For each gene 100 randomized MFE-profiles variants were computed basing on randomized sequences generated by the dinucleotide preserving and codon preserving randomization models (both preserving also the encoded proteins, see section above). The UTRs were not changed in the randomization as in this study we are interested in the coding regions.

The mean MFE-profile was obtained by averaging the WE-profiles of all genes (in a position wise manner). In a similar manner, 100 randomized mean MFE-profiles were computed by grouping the randomized MFE-profiles of all genes in 100 groups, each group contains a different variant for each gene, and then averaging the profiles in each group in a position-wise manner.

In order to assess the statistical significance of the folding strength at a particular position in a sequence, the mean MFE values at this position was compared with the mean MFE values in the corresponding position in each one of the randomized variants by calculating an empiric P-value—a proportion of the randomized values as extreme as in the wild type. Positions with MFE related P-value<0.05 were defined as selected for strong/weak folding.

In addition, mean MFE values were computed for each gene over all windows (by averaging the values in the corresponding MFE-profiles) and compared to the mean MFE values obtained from the corresponding 100 randomized profiles. For each gene its mean MFE value was calculated and as were an average of 100 mean MFE values from its randomized variants; the distributions of the wild-type and randomized mean MFE values of different genes were compared using Wilcoxon signed-rank test. Early and late genes were analyzed separately.

Average Repetitive Substring (ARS) Index

This measure is based on the assumption that evolution shapes the organismal coding sequences (and other part of the gene) to improve their interaction with the intra-cellular gene expression machinery. Since these interactions are mediated via binding of the gene expression machinery (e.g. translation/transcription factors, RNAP, ribosomes, RNA binding proteins, etc.) to the genetic material (DNA or RNA), the genetic material tend to have optimized binding sites (which are sub-sequences of nucleotides). It was expected that binding sites will appear in many coding regions and that more optimal binding sites will tend to appear more times in the genome. Thus, if longer substrings of a genome tend to appear in a certain organism's coding sequence, it suggests that this coding sequence is more optimized to the intra-cellular gene expression machinery and thus it is probably more highly expressed. Here, the ARS index was computed for each bacteriophage gene in comparison to the host (*E. coli*) and in comparison to the rest of the viral genes.

The algorithm of ARS index is based on the following steps: (i) For each position i in the coding sequence S find the longest substring Sji that starts in that position, and also appears in at least one of the coding sequences of the reference genome (*E. coli*/viral). (ii) Let jSj denote the length of a sequence S; the ARS index of S is the mean length of all the substrings $S_i^j$:

$$ARS \frac{\sum s_i^j}{|s|}.$$

Rare Codons Analysis

Rare codons in a reference set of coding sequences were defined as codons with the relative synonymous fre-quency<0.2. Three reference sets were used: *E. coli* coding sequences, bacteriophage early coding sequences, bacteriophage late coding sequences.

A rare codons score (RCS) for a specific early/late/*E. coli* coding sequence with respect to a reference set of all early/all late/all *E. coli* coding sequences is defined as a percentage of amino acids in that sequence encoded by a rare codon out of all amino acids that are encoded by at least one rare codon in the corresponding reference set (if an AA is not encoded by codons that are rare in the reference set we exclude it from the analysis):

$$RCS = \frac{1}{N}\sum_c I_c, \quad I_c = \begin{cases} 1, & RSCF(c) < 0.2 \\ 0, & \text{otherwise} \end{cases},$$

where the sum is over all codons c that have at least one rare synonymous codon that appears in the reference set and N is the total number of such codons.

Late Genes Sampling

In order to control the influence of the difference of genes length between early and late groups the late genes were sampled so that the average length of both genes groups is the same. The sampling was of random contiguous blocks of codons from the late genes and according to distributions of early genes.

Viruses

Human Viruses analyzed in this study include Herpes viruses, papilloma viruses, Polyomavirus and HIV.

The analyzed bacteriophages include: bacteriophage Lambda, bacteriophage T4, bacteriophage Pak P3, bacteriophage phi29, bacteriophage T7, bacteriophage phiYs40, bacteriophage Fah, bacteriophage xp10, bacteriophage *Streptococcus* DT1, bacteriophage *Streptococcus* 2972, bacteriophage Mu, bacteriophage phiC31, bacteriophage phiEco32, bacteriophage p23-45 and bacteriophage phiR1-37.

These viruses were chosen since they have a known division to early and late genes annotated in the literature.

Additional Genomic Features Analyzed in this Study

Effective number of codons (ENC) is a measure that quantifies how far the synonymous codon usage of a gene departs from what is expected under the assumption of uniformity. ENC is a measure that quantifies how far the codon usage of a gene departs from equal usage of synonymous codons. It can be calculated from codon usage data alone and is independent of gene length and amino acid (AA) composition. ENC can take values from 20, in the case of extreme bias where one codon is exclusively used for each aa, to 61 when the use of alternative synonymous codons is equally likely and is defined by:

$$n = \sum_i^d x_i$$

$$p_i = x_i/n$$

xi is the number of synonymous codons of each type in the sequence, n is the number of times the AA appears in the sequence and p is the frequency (/probability) of each codon. The effective number of codons for the AA is:

$\widehat{N_e} = 1/\hat{F}$ where $\hat{F} = \Sigma_i^d p_i^2$

ENC for the group of AA with degeneracy d:

$$N = 1/\overline{\hat{F_d}} \text{ where } \overline{\hat{F_d}} = \frac{1}{|A_d|}\sum_{i \in A_d} \hat{F}_i$$

When an AA is missing we averaged over the rest.
Finally, ENC for the sequence (e.g., gene):

$$\widehat{N_e} = 2 + \frac{9}{\overline{\hat{F_2}}} + \frac{1}{\overline{\hat{F_3}}} + \frac{5}{\hat{F}_4} + \frac{3}{\overline{\hat{F_6}}}$$

GC-content is the percentage of nitrogenous bases on a DNA or RNA molecule that are either guanine or cytosine. GC-content (or guanine-cytosine content) is the percentage of nitrogenous bases on a DNA or RNA molecule that are either guanine or cytosine (from a possibility of four different nucleotides) and is defined as:

$$\frac{F(G) + F(C)}{F(A) + F(T) + F(G) + F(C)}$$

Where F( ) is a number of occurrences. We calculated the GC content in gene levels for all viruses, or for sets of viral genes.

Codon pair bias (CPB). To quantify the CPB, one follows and defines a codon pair score (CPS) as the log ratio of the observed over the expected number of occurrences of this codon pair in the coding sequence. The CPB of a virus is then defined as an average CPSs over all codon pairs comprising all viral coding sequences. To achieve independence from amino acid and codon bias, the expected frequency is calculated based on the relative proportion of the number of times an amino acid is encoded by a specific codon:

$$CPS = \log\left(\frac{F(AB)}{\frac{F(A) \times F(B)}{F(X) \times F(Y)} \times F(XY)}\right),$$

where the codon pair AB encodes for amino acid pair XY and F denotes the number of occurrences. The codon pair bias (CPB) of a virus, or set of viral genes, is than defined as an avenge of codon pair scores over all codon pairs comprising the viral coding sequences:

$$CPB = \frac{1}{k-1}\sum_{i=1}^{k-1} CPS[i]$$

Dinucleotide bias (DNTB). One defines a dinucleotide score (DNTS) for a pair of nucleotides as an observed over expected ratio of its occurrences in a sequence. The DNTB of a virus is defined as an average of DNTSs over all dinucleotides comprising all viral coding sequences. This can also be calculated for a set of viral genes. One computes a dinucleotide score (DNTS) for a pair of nucleotides XY as an odds ratio:

$$DNTS = \frac{F(XY)}{F(X)F(Y)},$$

where F denotes the frequency of occurrences. The dinucleotide pair bias (DNTB) of a virus is defined as an average of dinucleotide scores over all dinucleotides comprising all viral sequences:

$$DNTB = \frac{1}{k-1}\sum_{i=1}^{k-1} DNTS[i]$$

Nucleotide (NTB) and amino acid (AAB) biases are defined as a normalized Shannon entropy over the frequencies of the nucleotides/AA in a genomic sequence and is defined as:

$$E = -\frac{\sum_i F * \log_2(F)}{|\text{unique symbols}|}$$

Where E is entropy, F is the frequency of nucleotides or amino acids and the number of unique symbols equals to 4 in the case of nucleotides or 20 in the case of amino acids. This measure takes values between 0 and 1, and describes how dispersed the distribution of the alphabet elements is: higher values correspond to more uniform nucleotide usage; lower values correspond to more biased nucleotide, indicating that some nucleotides/amino acids are preferred (positions are conserved)

Phylogenetic Reconstruction

Let A and B be two proteomes of two different viruses consisting of n and m proteins correspondingly. The total length of each proteomes is: $|A| = \Sigma_{i=1}^n |a_i|$ and $|B| = \Sigma_{i=1}^m |b_i|$ (|x| is the length of protein x). We define an ARS score of a protein $a_i \in A$ with respect to the proteome B as:

$$L(a_i, B) = \frac{1}{a_i}\sum_{j=1}^{|a_i|} l_i(j)$$

Where $l_i(j)$ is the length of the longest substring $[a_i(j)a_i(j+1) \ldots a_i(j+l(j)-1)]$, starting at position j in $a_i$ that exactly matches a substring $[b_\gamma(k)b_\gamma(k+1) \ldots b_\gamma(k+l(j)-1)]$ starting at some position k in one of the proteins $b_\gamma \in B$.

The ARS score of the entire proteome A with respect to the proteome B is defined as:

$$L(A, B) = \frac{1}{|A|}\sum_{i=1}^n [|a_i|L(a_i, B)] = \frac{1}{|A|}\sum_{i=1}^n \sum_{j=1}^{|a_i|} l_i(j)$$

The first equality is a weighted average of ARS scores $L(a_i,B)$ over all proteins in A; for each protein, $a_i \in A$ its weight is defined as its relative lengths $$\frac{|a_i|}{|A|}.$$

. The second equality means that the weighted average described above is just equal to the total sum of the longest common substrings $l_i(j)$ over all positions j in all proteins $a_i$, divided by the total length of the proteome A (this equivalence immediately follows from the definition of $L(a_i,B)$). Intuitively, the larger this $L(A,B)$ is, the more similar the two proteomes are.

For a given A, to account for B's length (longer B will tend to have larger $L(A,B)$ we normalize by $\log(|B|)$: $L(A,B)/\log(|B|)$.

Moreover, $L(A,B)$ is a similarity measure, while we are after distance d. Therefore, we take the inverse and then subtract a "correction term" that guarantees $d(A,A)$ will always be zero, yielding:

$$d(A, B) = \frac{\log(|B|)}{L(A, B)} - \frac{\log(|A|)}{L(A, A)}$$

Note that if A is a single protein, then by the definition of ARS and a formula for the sum of geometric progression:

$$L(A, A) = \frac{1}{n}\sum_{j=1}^{n} l(i) = \frac{1}{n}\sum_{j=1}^{n}(n - i + 1) = \frac{1}{2n} * n(n+1) = \frac{n+1}{2}$$

However, if A is a proteome that contains several proteins than this formula is no more applicable; in this case $L(A,A)$ should be computed by the formula of $L(A,B)$.
Finally, to ensure symmetricity we define:

$$d_s = \frac{d(A, B) + d(B, A)}{2}$$

$d_s$ is the ARS induced distance for tree building.
The tree was built using neighbor joining algorithm.

Example 1

Design of Codon Bias Analysis

Bacteriophage lambda is a well-known and studied member of the Siphoviridae family of double-stranded DNA viruses in the Caudovirales order (also known as "tailed bacteriophages" due to their characteristic form). During its lifecycle, this phage either stably resides within the genome of its E. coli host through lysogeny, or enters into a lytic phase (which lasts about 25 minutes) during which it produces progeny viral particles, and lyses and kills the host cell. The genome size of bacteriophage lambda is about 50 kilobases (kb) and includes 66 known genes that were analyzed in this study. These genes were divided into two groups, "early" and "late" according to the stages in the lytic phase when their expression is dominant.

In order to explore the way in which translation efficiency related information is encoded on a synonymous level in the coding regions of genes, specifically genes that are expressed during different bacteriophage lambda development stages, large scale analysis of different types of genomic synonymous information related to regulation of translation efficiency was carried out.

The research outline of the study is described in FIG. 1A. The analysis was based on the genome (mainly the coding sequences) of the E. coli host (A.), the genome of bacteriophage lambda (B.) and the ribo-seq measurements of these two (C.). To assess the statistical significance of the signals found in the analyzed viral genes and to exclude the possibility that these signals are un-direct consequences of other genomic properties, they were compared to signals expected by chance in the corresponding randomized variants (D.); two different randomization models were employed: one that maintains the encoded proteins and the frequencies of pairs of adjacent nucleotides (dinucleotides), and the other that maintains the encoded proteins and the frequencies of synonymous codons (codon usage bias). Basing on the ribo-seq data, the expression levels of each gene at each time point (E.), the relative decoding rate of each codon (F.), and the classification of the bacteriophage genes to early and late (with respect to the beginning of the lytic phase) (G.) were derived. Based on A., B., D., G., synonymous codons usage analysis of coding regions in viral and E. coli genes (H.) using the relative synonymous codons frequencies (RSCF) (I.) and tRNA adaptation indexes (tAI)(J.) was performed. Based on E., F., G. codons decoding rates for early/late genes at different stages of the viral development (L.) on per-codon (M) and gene/genomic levels (N.) was analyzed. In addition, based on A., B., D., G., the local and global signals of evolutionary selection for strong/weak mRNA folding (K.) and for higher order synonymous information encoded in repetitive sequence motifs that are longer/more complex than single codons in the coding regions of the bacteriophage genes (O.) was studied.

Example 2

Early and Late Genes Have Different Codon Compositions

Figure 1B:
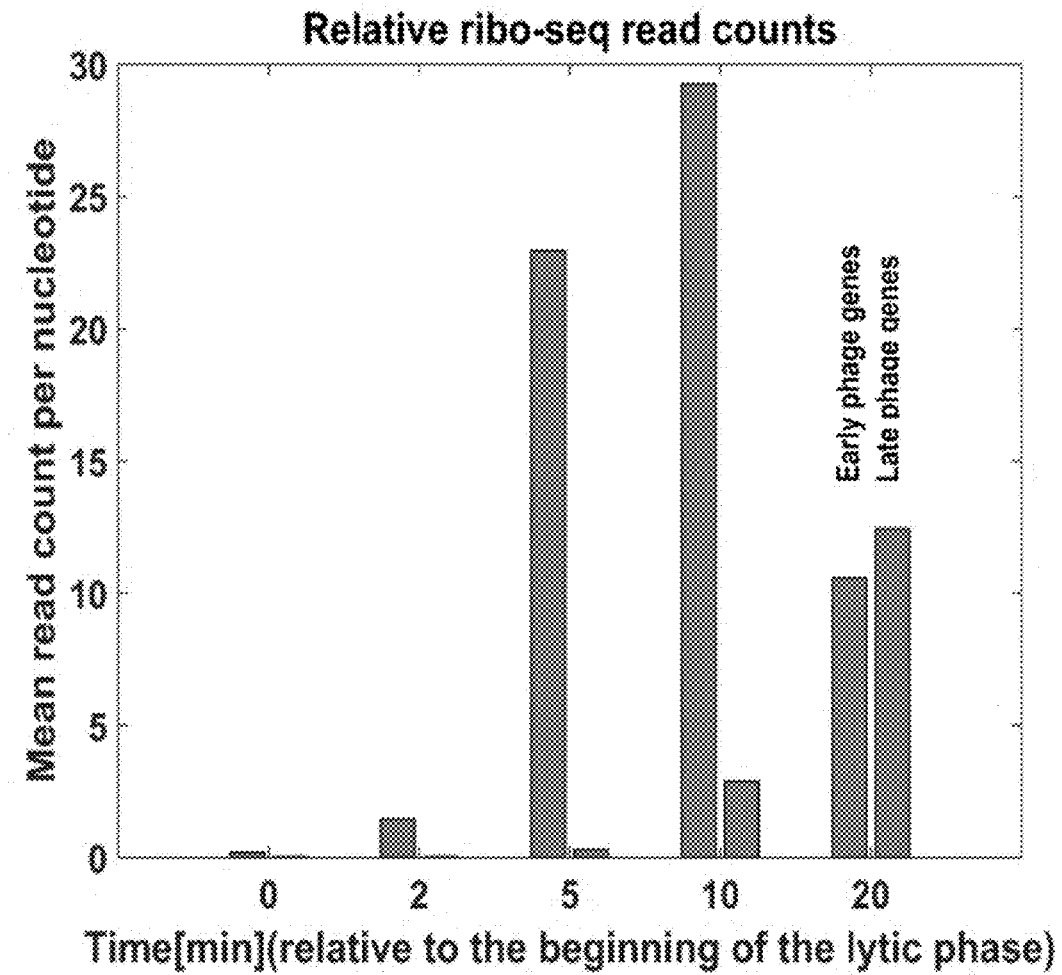

In order to compare the properties of coding regions of bacteriophage early and late genes the two groups of genes must be defined. The analysis of ribo-seq read count per nucleotide for early and late groups of bacteriophage genes appear in FIG. 1B. As can be seen, at the first time point the read count of both groups is very low. Afterwards the expression levels of both gene groups increase; whereas the expression of the early gene group is dominant during minutes 1-10, the expression levels of late group genes becomes dominant towards the 20th minute. Specifically, 32 of the bacteriophage genes are defined as early genes: their expression levels increase from minute 5 to 10, and then decrease by minute 20 (relative to the beginning of the lytic process). The remaining 34 genes are defined as late genes: their expression levels become significant only at minute 10 from the beginning of the lytic process, and increase considerably by minute 20 (FIG. 1B).

Figure 2A:
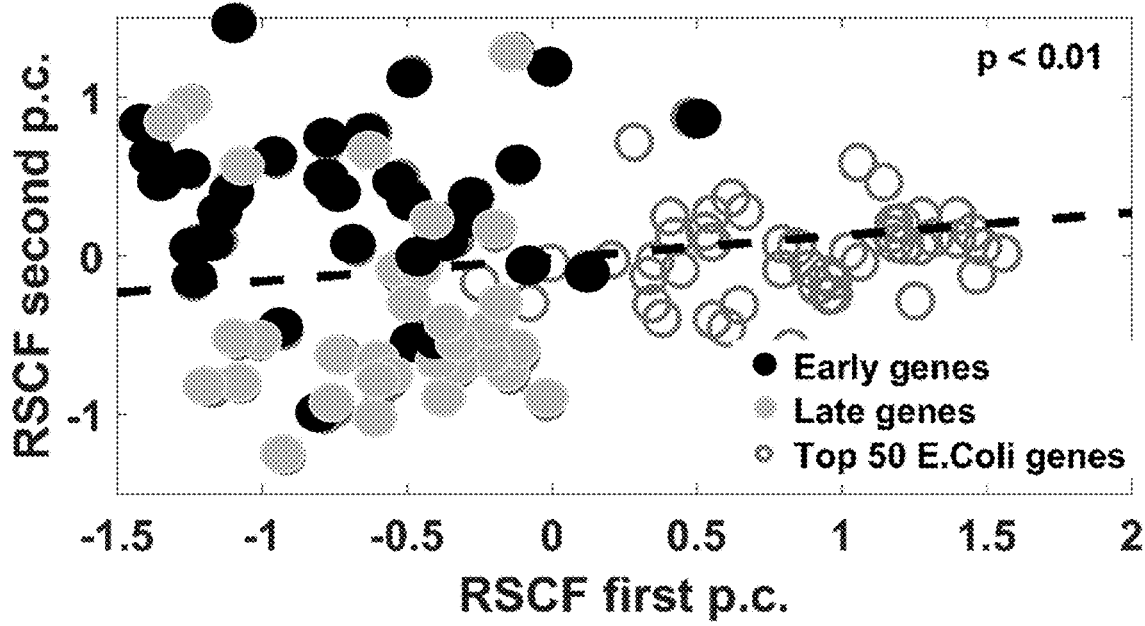
FIGS. 2A-F. (2A) A plot of two principal components of codon relative frequency vectors for all bacteriophage genes and the top 50 *E. coli* genes, indicating that early and late genes tend to be clustered into two distinct groups. (2B). Histograms of 500 random average MTDR values of early and late viral genes at different time points; the wild type average MTDR appears as a line. (2C). A bar chart depicting relative translation elongation efficiency u coefficient, RTEC=(mean MTDR$_E$–mean MTDR$_L$)/(mean MTDR$_E$+ mean MTDR$_L$) as a function of time from the beginning of the lytic stage (0-20 minutes), where MTDR$_E$ and MTDR$_L$ signify the MTDR of early and late genes respectively. (2D) A line graph showing correlation between codon typical decoding rates (TDRs) and codon frequencies at different time points for *E. coli* genes, just early viral genes, just late viral genes and all viral genes. Time points with significant correlations (Spearman p-values lower than 0.05) are marked by asterisk. (2E) The wild type mean tRNA adaptation index (tAI) (line) vs. the distribution of mean tAI values of early and late genes corresponding to 500 randomized variants of each gene. The wild-type mean tAI is significantly higher than expected in random only for early genes. (2F) A line graph showing the correlation between the TDR and the tAI of different codons over time during the lytic phase of the virus's life cycle.

At the first step (FIG. 2A), the synonymous codons usage in E. coli and bacteriophage early and late coding sequences was compared. To this end, for each coding sequence, there was computed a relative synonymous codon frequency (RSCF)—a 61-dimensional vector representing each codon (except the stop codons) by its frequency in that sequence normalized relative to the frequencies of other synonymous codons coding for the same amino acid (See Materials and Methods). The analysis demonstrated that the early and late genes tend to be clustered into two significantly separated (p-value<0.01) clusters according to their synonymous codons usage. In addition, synonymous codon usage in both groups of viral genes was found to be significantly different (p-value<0.01) from that of *E. coli* (FIG. 2A). These results provide evidence that different sets of synonymous codons for early vs. late genes are selected in the course of viral evolution and may be related to the optimization of the viral fitness.

Example 3

Differential Codon Usage in Early and Late Genes can be Partially Explained by Adaptation of Translation Elongation Efficiency to Different Bacteriophage Developmental Stages It having shown that early and late viral genes have a significantly different composition of synonymous codons which may be associated with various features of their expression, one such feature was focused upon. Specifically, the translation elongation efficiency of bacteriophage coding regions and how that efficiency behaves in different stages of the viral lytic cycle. To this aim a condition specific measure of translation elongation was employed to study the elongation speed of viral codons/genes during the different steps of phage development. This measure, called Mean Typical Decoding Rate (MTDR), is based on the estimation of a typical codon decoding rate (TDR) for each codon at each time point based on the ribosome profiling data and enables ranking codons and coding regions according to their elongation rate while controlling for other factors, such as initiation rates and mRNA levels (see Materials and Methods).

Figure 2B:
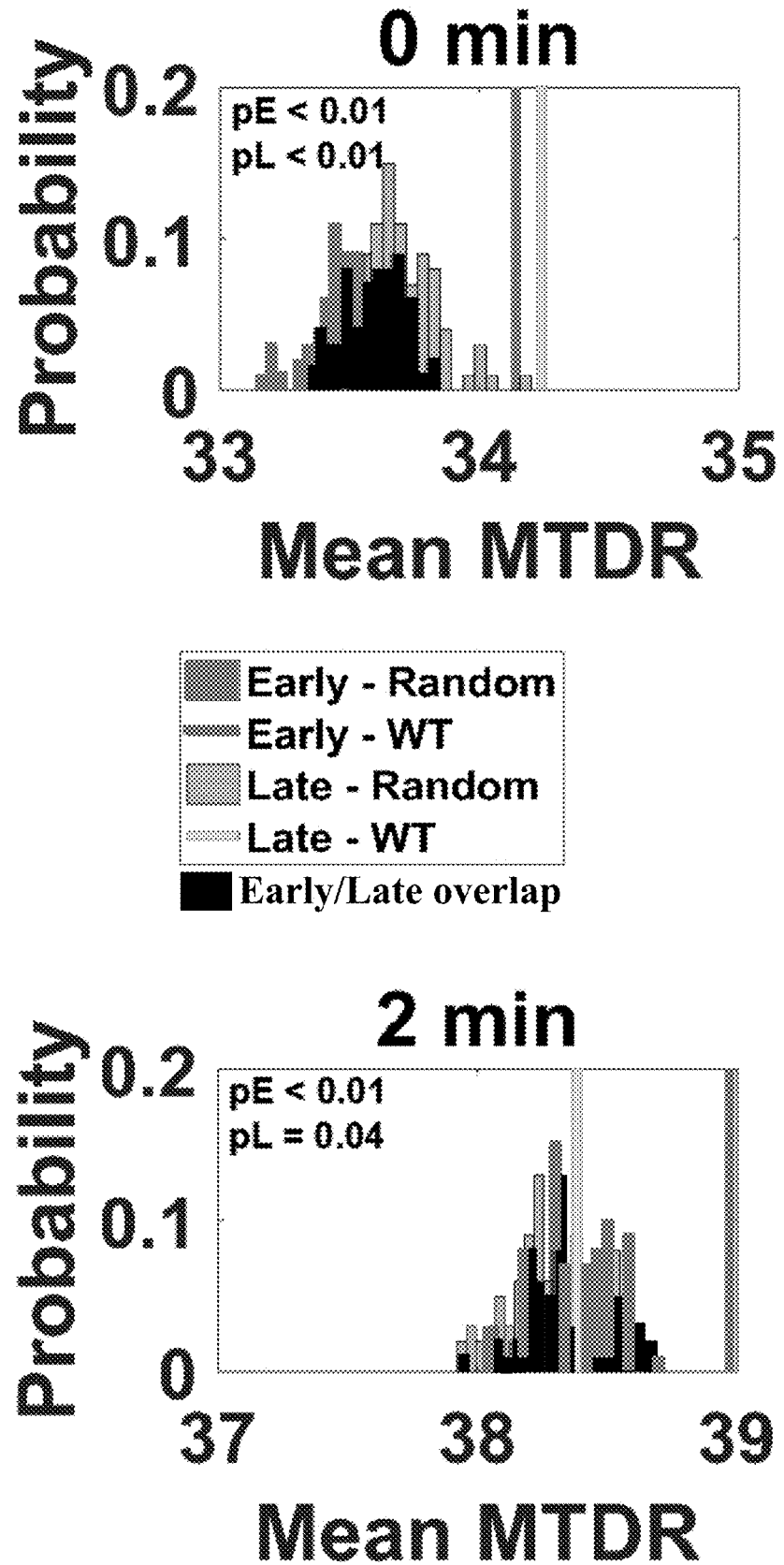
Figure 2B:
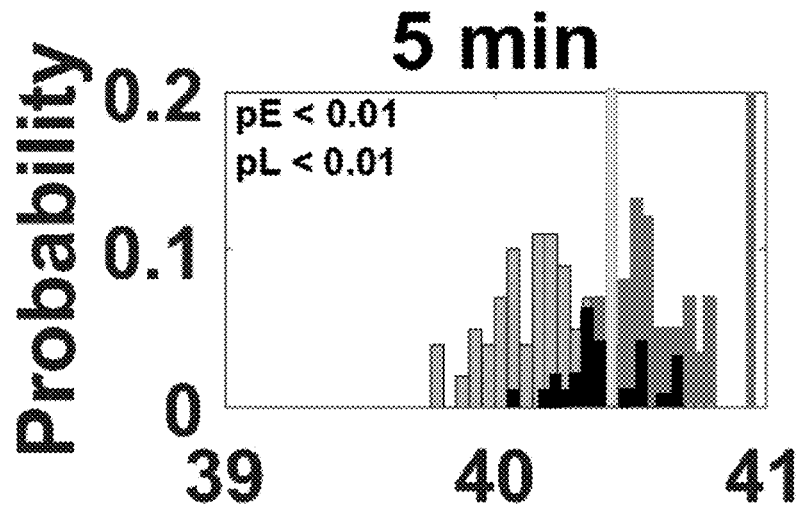
Figure 2B:
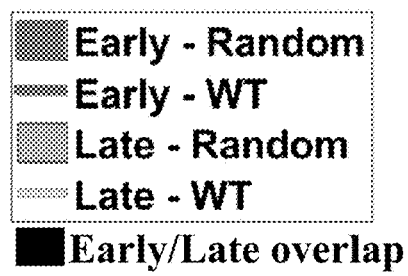
Figure 2B:
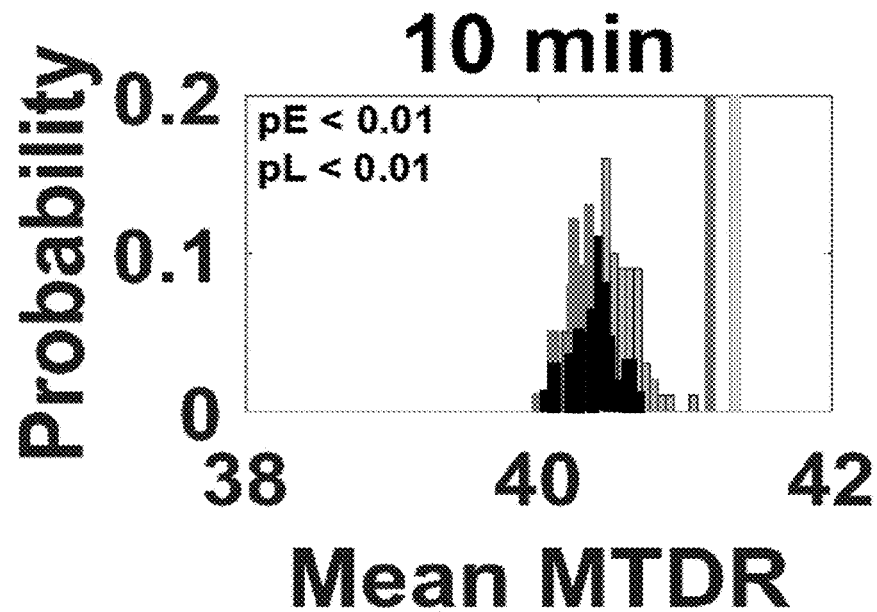
Figure 2B:
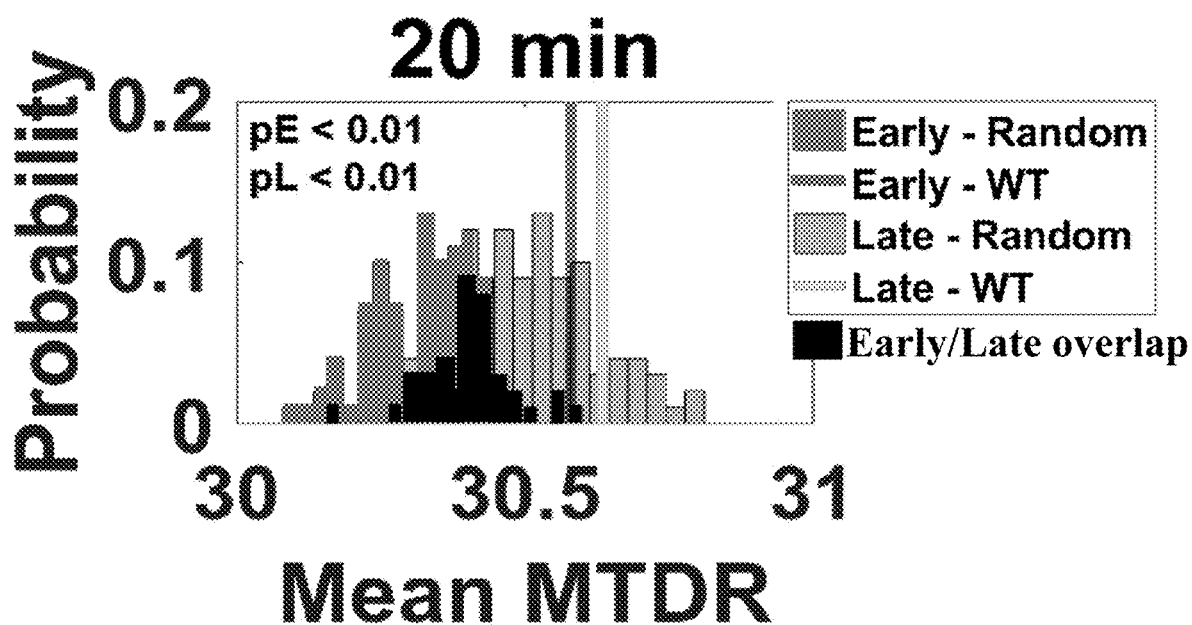
Figure 3A:
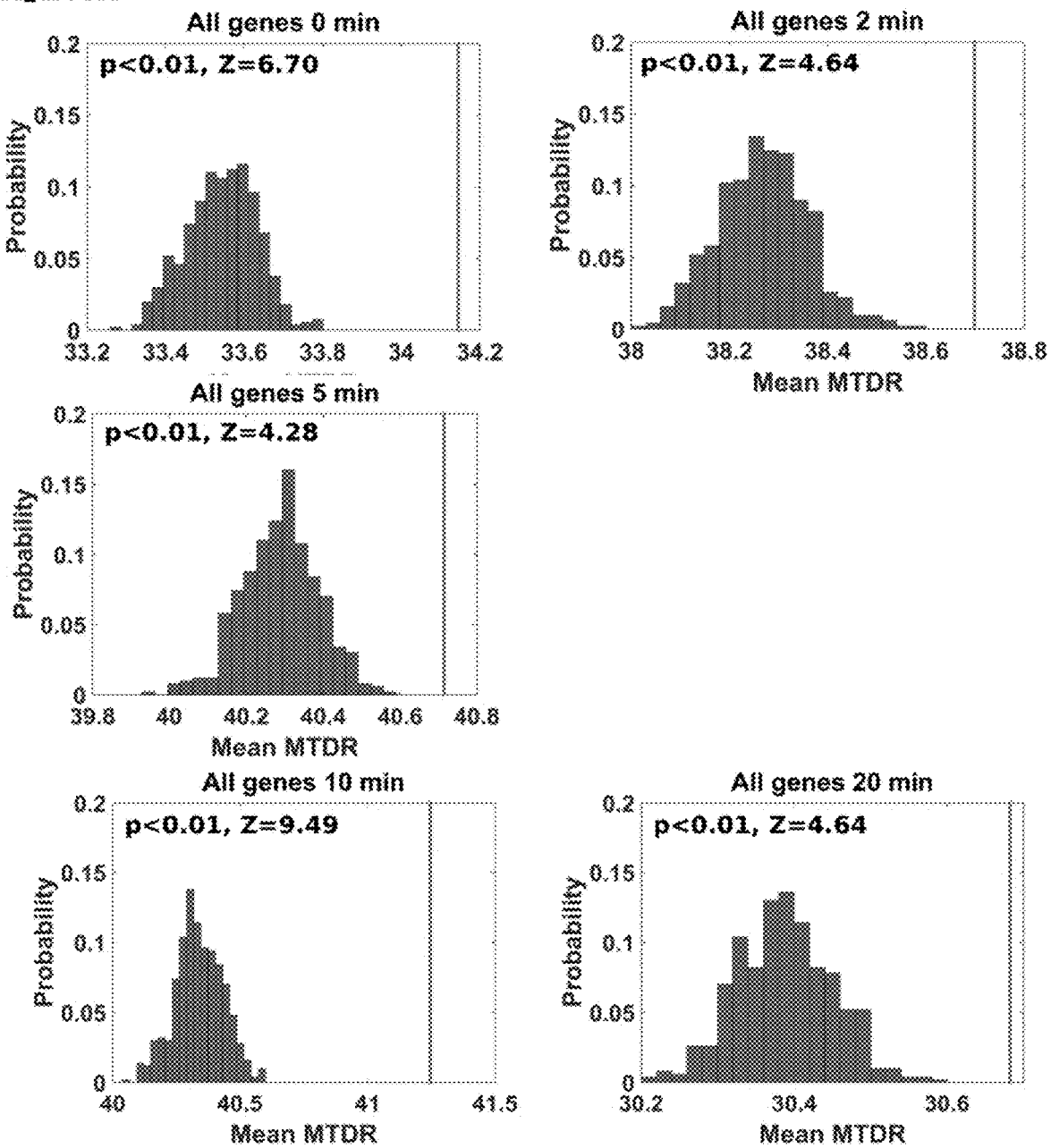
FIGS. 3A-B. (3A) Histograms of 500 random average MTDR values of all viral genes in the grey; the wild type average MTDR appears as a line. (3B) A line graph, showing per condition Partial correlation (controlling for gene length) between rare codons score and mean read counts for the two Lambda gene groups (early and late) and the *E. coli* genes. Time points with significant correlations (Spearman p-values lower than 0.05) are marked by asterisk. For *E. coli*, the correlations are significant at all time points (p-value<0.05). For late genes, the correlation is significant only for the late time points. No significant correlation can be seen for early genes. The correlation between the Spearman correlation (y-axis) and the time condition (x-axis) are 0.9 for early genes (p=0.083), −1 for late genes (p=0.017 and 1 for *E. coli* genes (p=0.017).

At the first step, it was necessary to check whether the bacteriophage coding regions undergo any selection for optimizing translation elongation. To this end, at every time condition two average MTDR values were computed, for early and late genes separately, and they were compared to the average MTDR values obtained for corresponding randomized variants that maintain the wild type amino acid content and the dinucleotide distribution (See Materials and Methods). As can be seen in FIG. 2B and FIG. 3A, the average MTDR of both groups is significantly higher than expected from the random model at all time points (early: p-value<0.02, z-score>2.2; late: p-value<0.0006, z-score>2.4). These results suggest that, indeed, translation elongation efficiency is maintained throughout the lytic cycle of infection and may be a factor that drives codon evolution in both early and late bacteriophage genes.

Figure 2C:
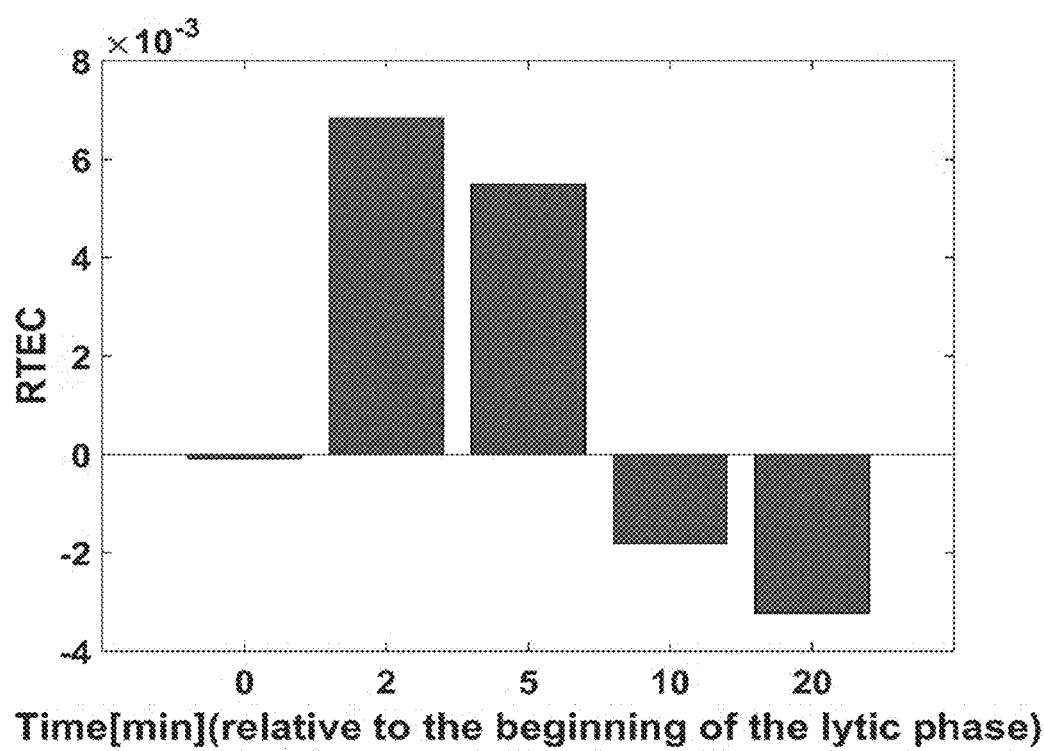

At the next step, to compare the translation elongation efficiency between early and late genes, the relative translation elongation efficiency coefficient (RTEC) was examined. The RTEC quantifies the relative differences in average MTDR values of two gene groups: more positive RTEC values mean that early genes are more efficient than the late genes, and vice versa, more negative RTEC values mean that late genes are more efficient than the early ones; RTEC values close to zero mean that the two groups of genes have a similar translational efficiency. FIG. 2C describes the RTEC as a function of time (0-20 minutes). As can be seen, the relative efficiency of elongation of early genes (in comparison to the late genes) is high at the beginning and becomes lower with time (p-value=0.04; based on spearman correlation). These results demonstrate that translation elongation efficiency of the early genes is relatively higher at the early stages of the bacteriophage development (when they are expressed) and the translation elongation efficiency of the late genes is relatively higher at the late stages of the bacteriophage development (when they are expressed).

Figure 2D:
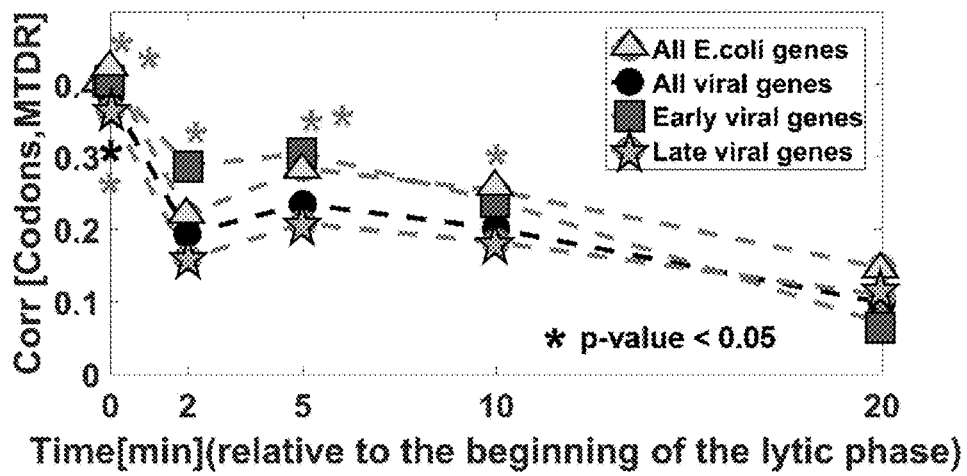

FIG. 2D describes the per codon correlation between the TDR and relative synonymous codon frequencies (RSCF) for the two bacteriophage gene groups (early and late) and the *E. coli* genes at different time points. As can be seen, the correlation is higher and significant for the early points in the case of the *E. coli* and early bacteriophage genes. For the late genes, the correlation is significant only at the initial point. The fact that the correlation between RSCF and TDR in the case of the early viral genes is significant at the first three points supports the conjecture that the relative codon decoding times change during the viral development; this is probably related, among others, to the fact that the bacteriophage affects extensively the gene expression in the cell.

The lower correlations at time 2 minutes does not seems to be related to trivial biases/problems with the experiment as the number of reads in the *E. coli* (used for inferring the MTDR) is similar to the number of read at different time points; in addition, the number of reads mapped to the viral genes is higher than in time 0. Thus, it is possible that the lower correlation is related to a biological phenomenon: e.g. it is possible that in this time point there is (strong) deviation (which is possibly temporary) of the concentration levels of the translation factors in the cell related to the other points; while the codon distributions were shaped to fit the other (longer) periods of the bacteriophage development.

Example 4

Figure 2E:
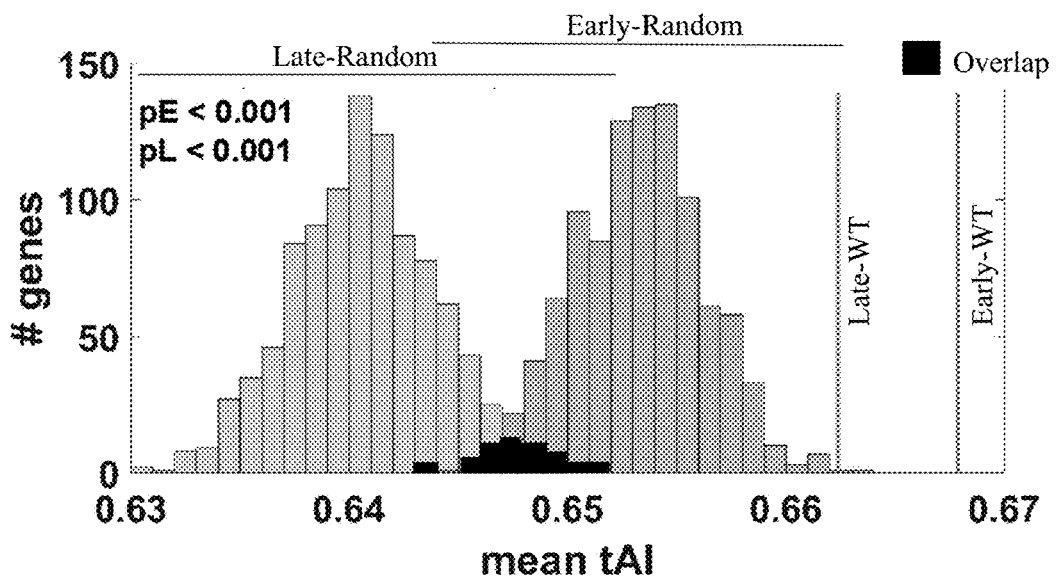
Figure 2F:
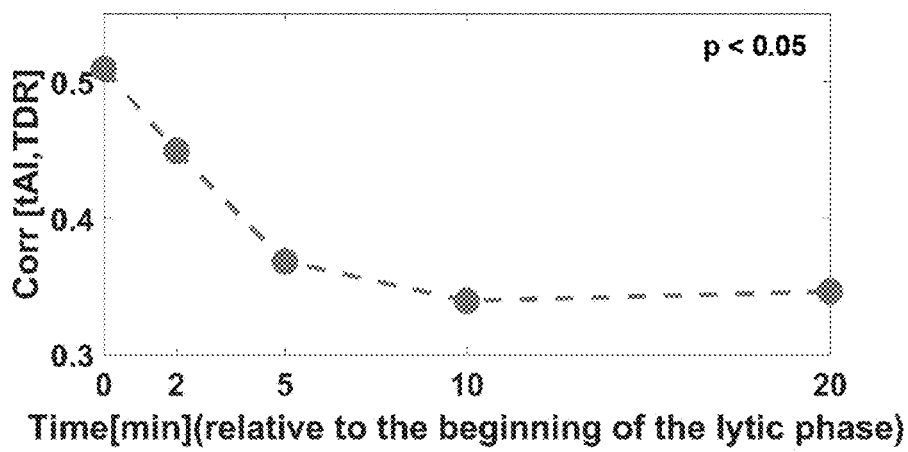

Selection for Translation Efficiency in Bacteriophage Genes may be Partially Explained by Adaptation to *E. coli* tRNA Pool and the Fact that it Changes During Bacteriophage Development Previous studies demonstrated that the codon decoding times may be directly influenced by the tRNA levels in the cell. In FIG. 2E the adaptation of the viral codons to the genomic tRNA copy number in the host at natural conditions was analyzed (see Materials and Methods) and it was found to be significant in comparison to the randomized variants that maintain the di-nucleotides distribution for both early and late gene groups. However, as can be seen in FIG. 2F the correlation between the TDR and the tAI of different codons is significant but decreases during the viral development stages. These results may suggest that, among others, the tRNA levels change during the viral development stages, affecting the codon decoding times.

Figure 3B:
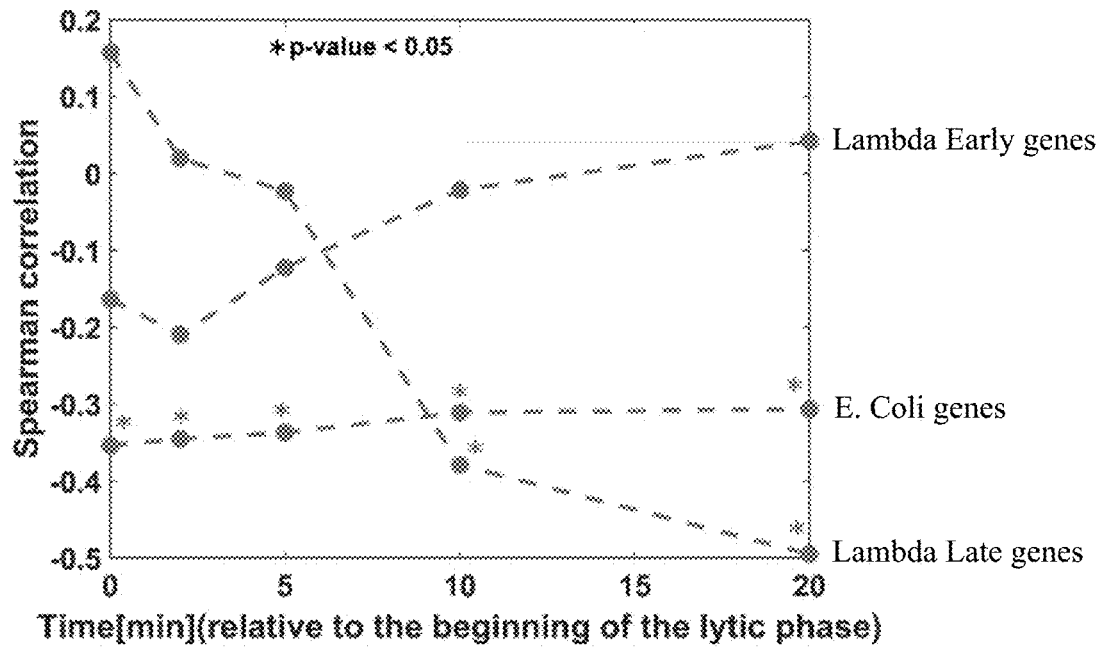
Figure 4A:
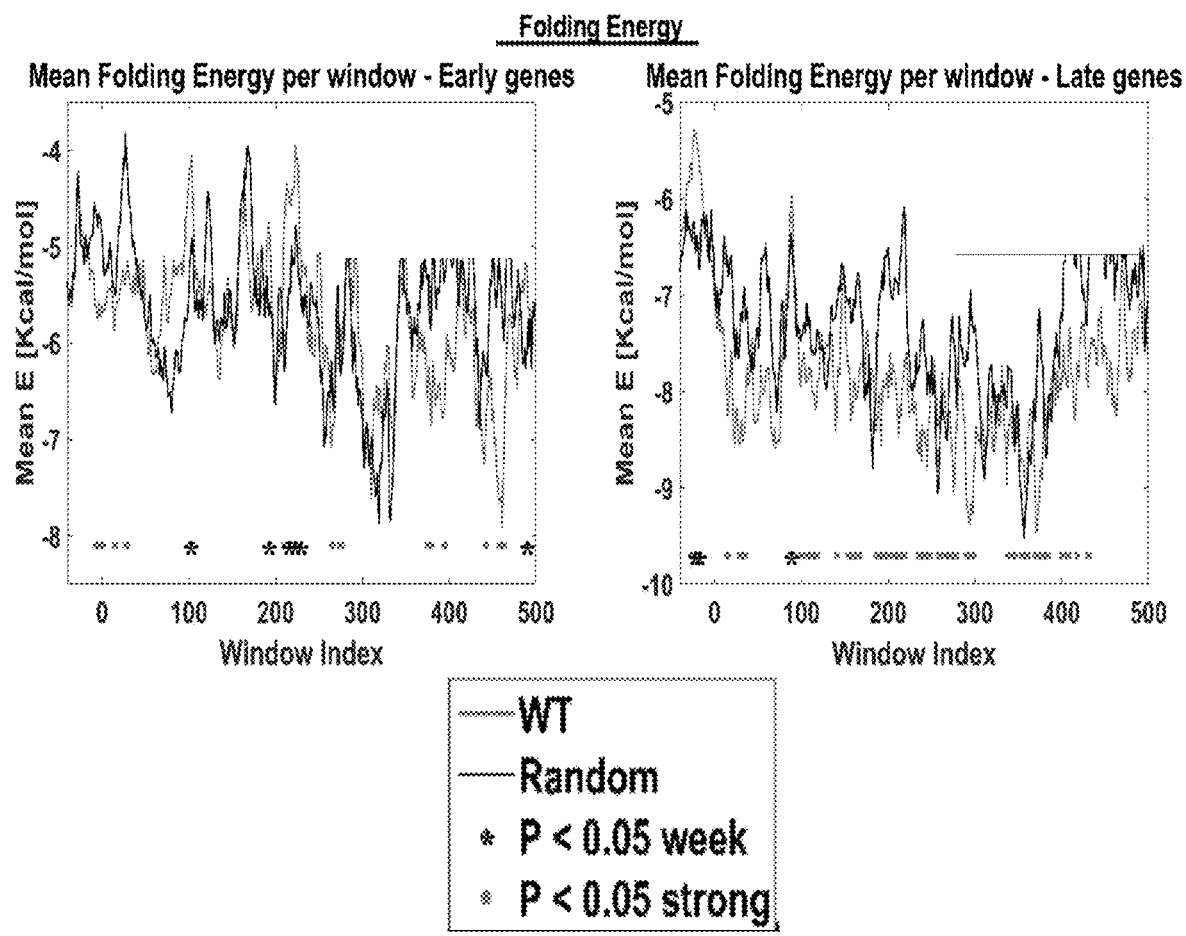
FIGS. 4A-D. (A-B) Line graph profiles of folding energy (average MFE in all windows of 39-nt length) across the bacteriophage genome (gray) vs. an averaged profile corresponding to 100 randomized variants (black) based on dinucleotide preserving randomization; the window index denotes the distance (in nucleotides) from the beginning of the ORF to the beginning of the window. Regions where the folding energy of the wild type genome is significantly higher (star) or lower (dot) than in randomized variants are marked at the bottom of the figure. (A) The profiles include the 50-UTR near the beginning of the ORF (negative window indexes). (B) The profiles include the 30-UTR near the ending of the ORF (positive window indexes). (C) Histograms of mean local folding energies (folding energies averaged over all the windows of each gene) compared with randomized mean local folding energies obtained from two models: (i) proteindinucleotides preserving and (ii) protein-codon usage bias preserving. (D) Histograms of log[ARS index]. Eight analyses were performed: two types of reference genomes; bacterial and viral, two type of randomizations; dinucleotide and codons, two groups of genes; early and late. In each histogram, the wild type distribution is compared with the mean random distribution (1,000 random genomes). The P-values were calculated according to Wilcoxon signed-rank test.
Figure 4B:
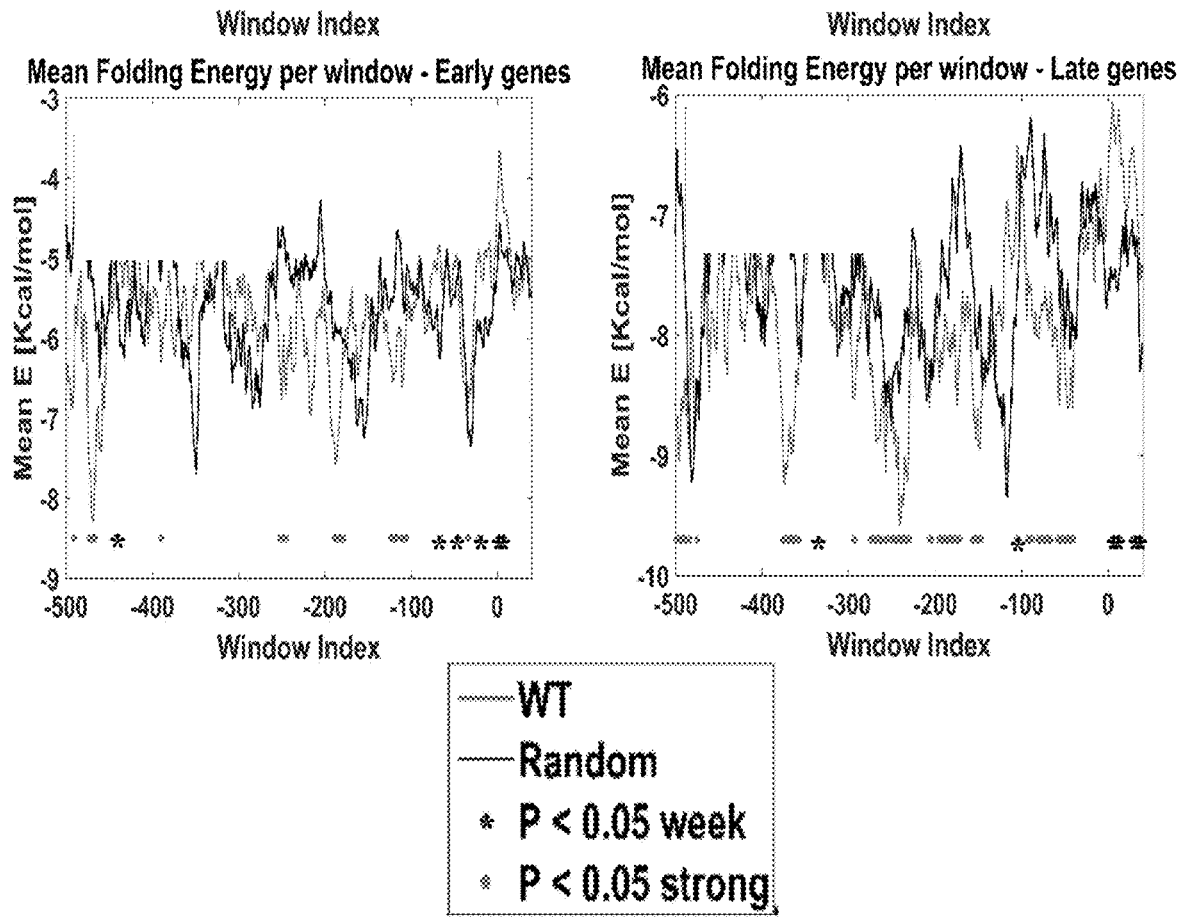
Figure 4C:
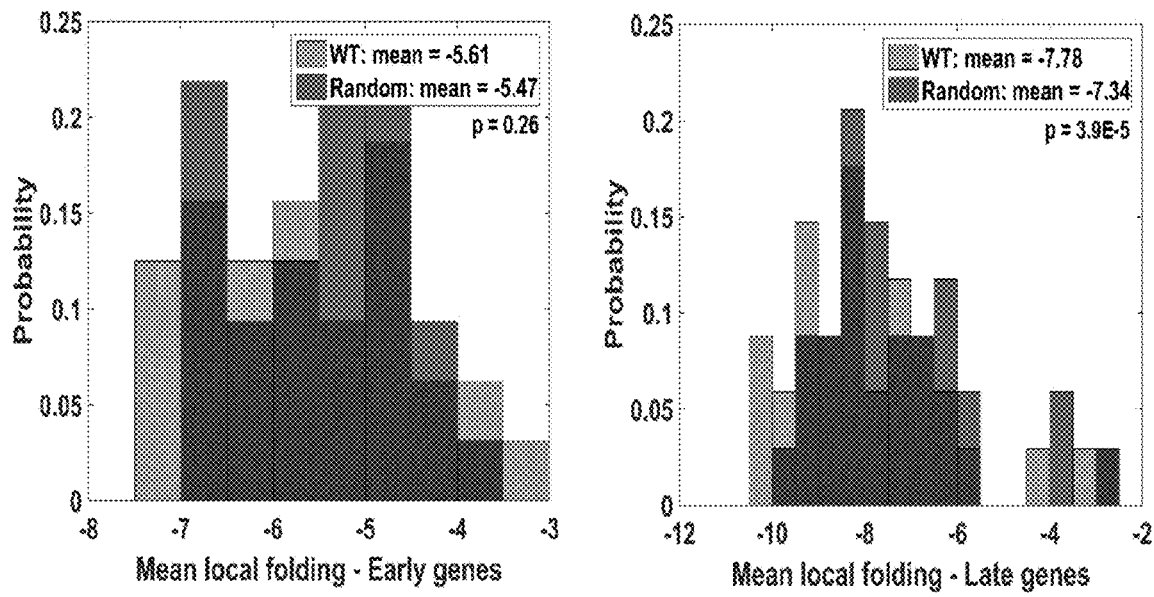
Figure 4D:
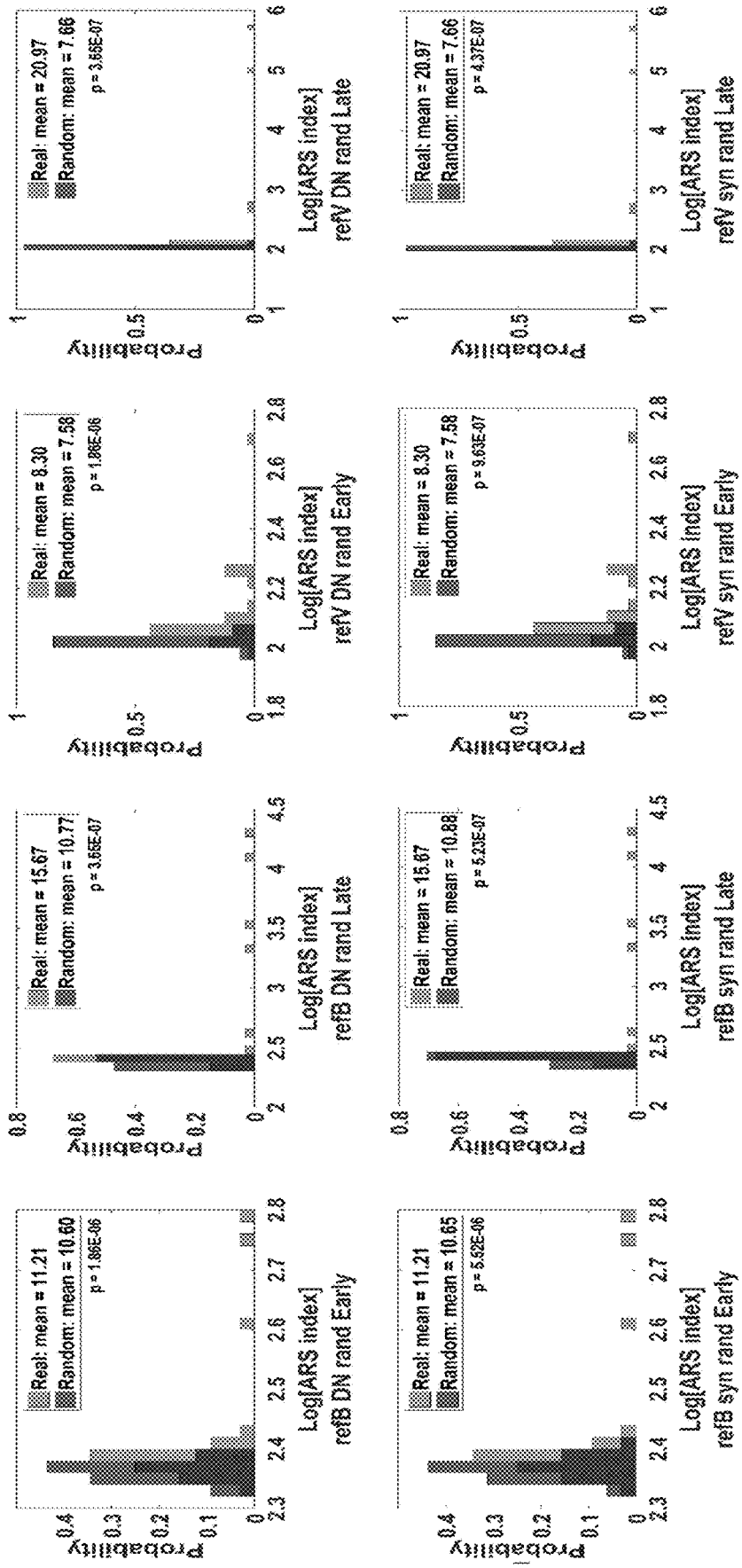

In addition, the tendency of early/late bacterial coding sequences to use rare synonymous codons with respect to early/late/bacterial gene groups respectively (rare codons score) was calculated. FIG. 3B describes the per condition partial correlation (controlling for gene length) between rare codons score and mean read counts for the two viral gene groups (early and late) and the *E. coli* genes. As can be seen, the correlation decreases in the case of the early genes and *E. coli* genes and increases for late genes Our analysis demonstrates that early/late genes with rare early/late genes codons tend to be lowly expressed at the early/late stages respectively.

The results reported in this section support the conjecture that some of the differences between the early and the late genes are related to the adaptation of viral codons to the intracellular environments in different stages of the phage development. Specifically, such adaptation may be the result of the fact that the typical decoding times (possibly due to changes in tRNA levels) change during the bacteriophage development.

Example 5

Codon Bias in Other Bacteriophages and Human Viruses

As demonstrated above, viruses undergo an extensive evolutionary selection for adaptation to their host environment, and thus it can be assumed that their codon composition reflects an efficient adaptation of the viral machinery at specific replication stages and therefore may be used as a reference set for codons substitution. To further broaden the known viruses for which this is true, 14 additional phages with known temporal gene classification were analyzed.

In order to compare the synonymous codons usage in early and late genes, each coding sequence was represented by its relative synonymous codons frequencies (RSCF)—a 61 dimensional vector expressing each sense codon by its frequency in that sequence normalized relative to the frequencies of other synonymous codons coding for the same AA. A clustering analysis was then performed, assuming that RSCF vectors that are closer with respect to Euclidian metric correspond to genes with a more similar content of synonymous codons (see Materials and Methods).

Figures 5A, 5B:
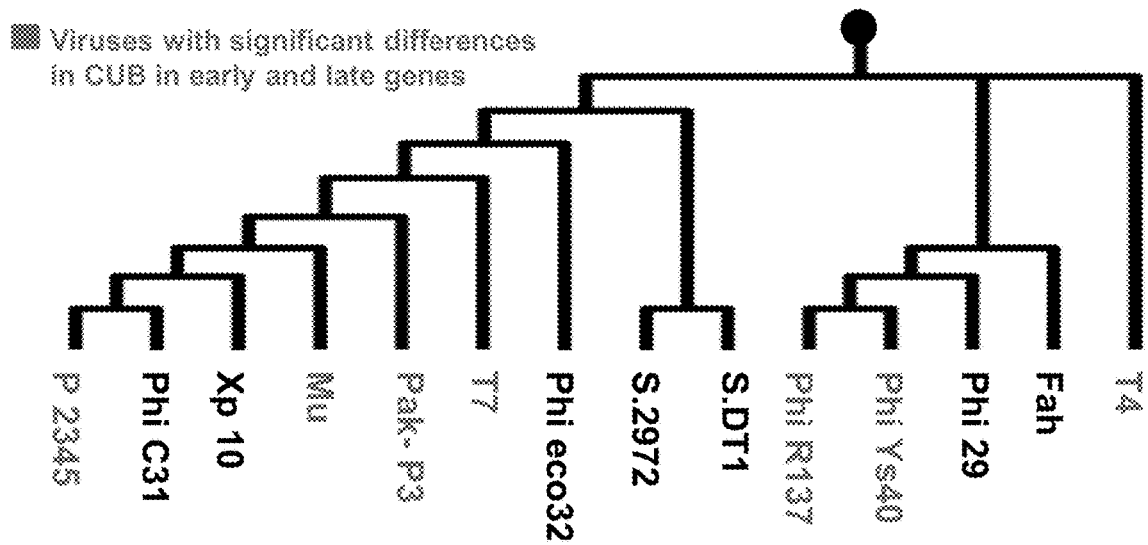
FIG. 5A-H. (A) A phylogenetic tree built from complete phage proteomes using ARS distance (see Materials and Methods). Phages with significant differences in temporary codon usage are marked by blue. (B) Table of viruses with significant (p-value<0.05) separation between early and late genes with respect to synonymous codons or AA are marked by stars. (C-D) Scatter plots of the CUB principal component analysis (PCA) for (C) significantly separated bacteriophages and (D) not significantly separated bacteriophages. (E) Bar charts of PCA of codon usage variances distribution for all 14 bacteriophages. (F-G) Scatter plots of the amino acid usage PCA for (F) significantly separated bacteriophages and (G) not significantly separated bacteriophages. (H) Bar charts of PCA of amino acid usage variances distribution for all 14 bacteriophages.
Figure 5C:
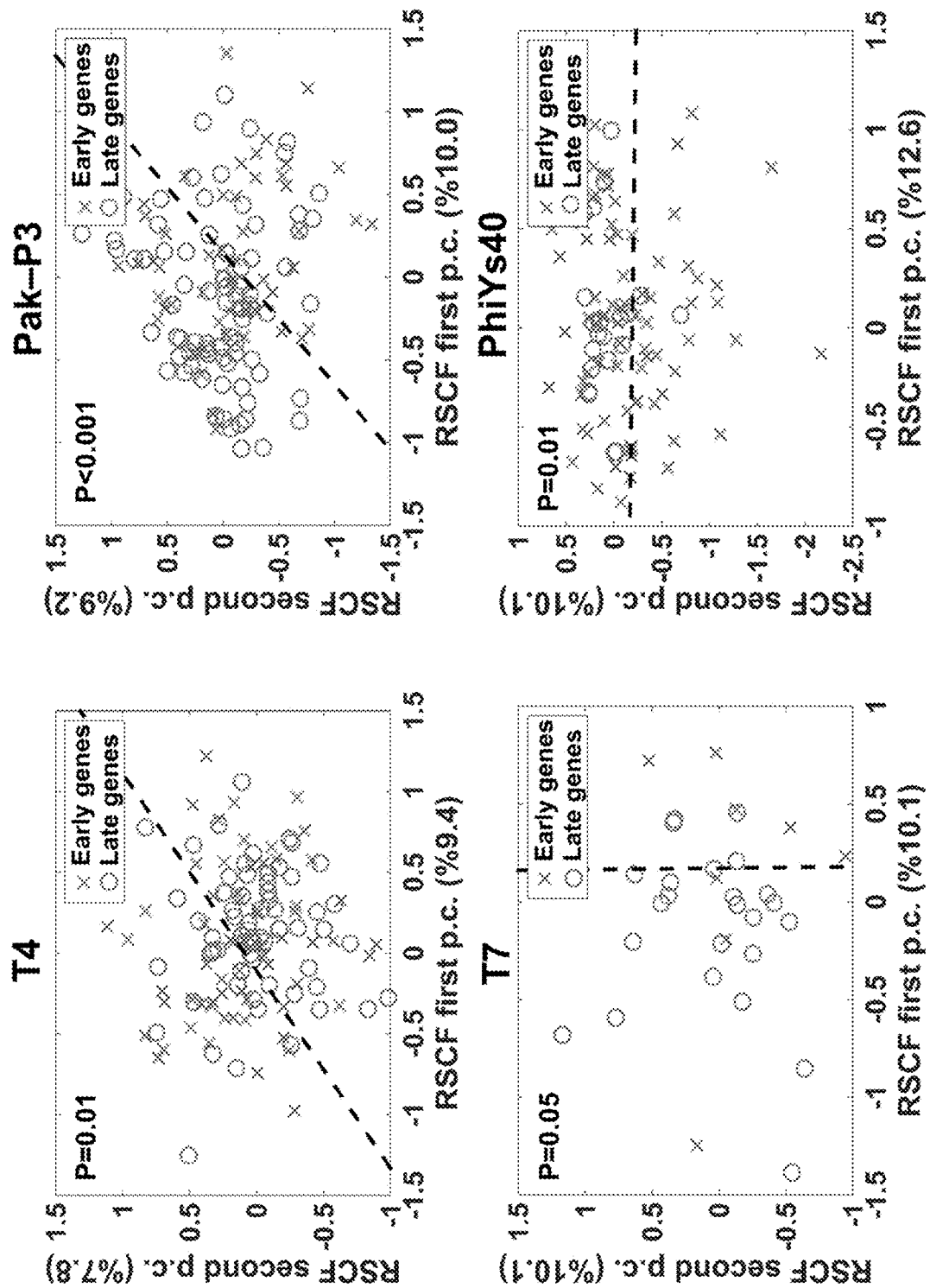
Figure 5C:
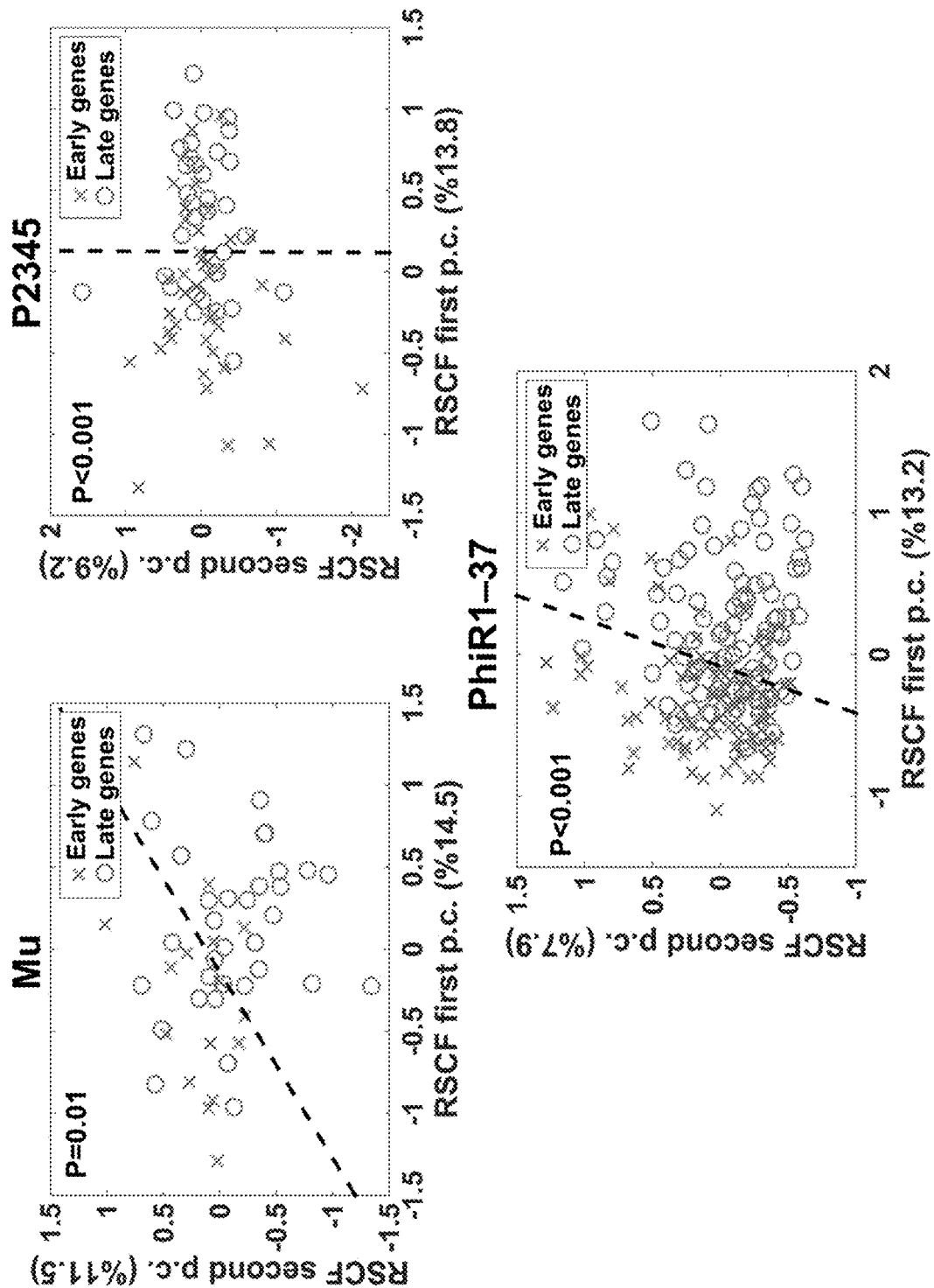
Figure 5D:
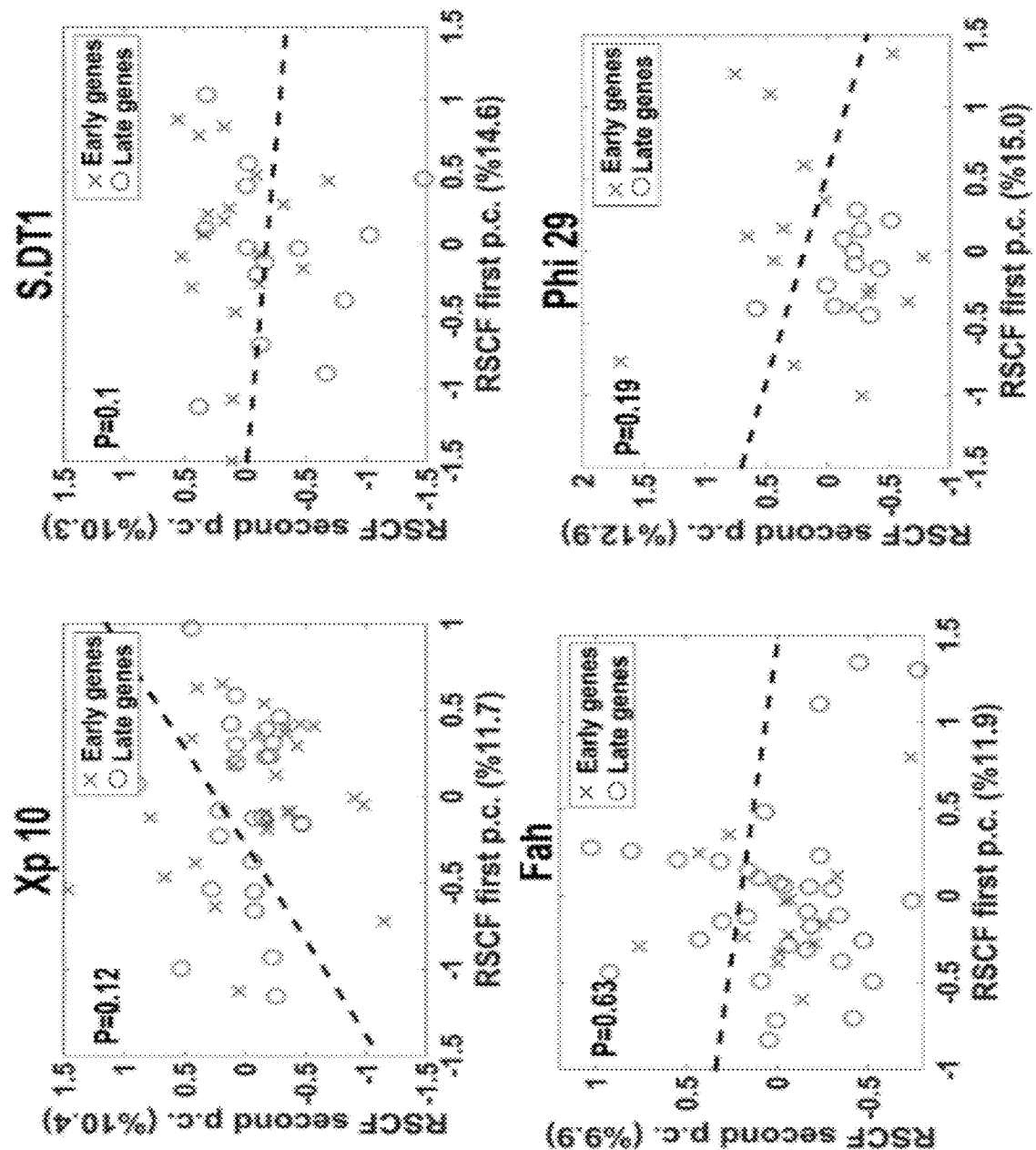
Figure 5D:
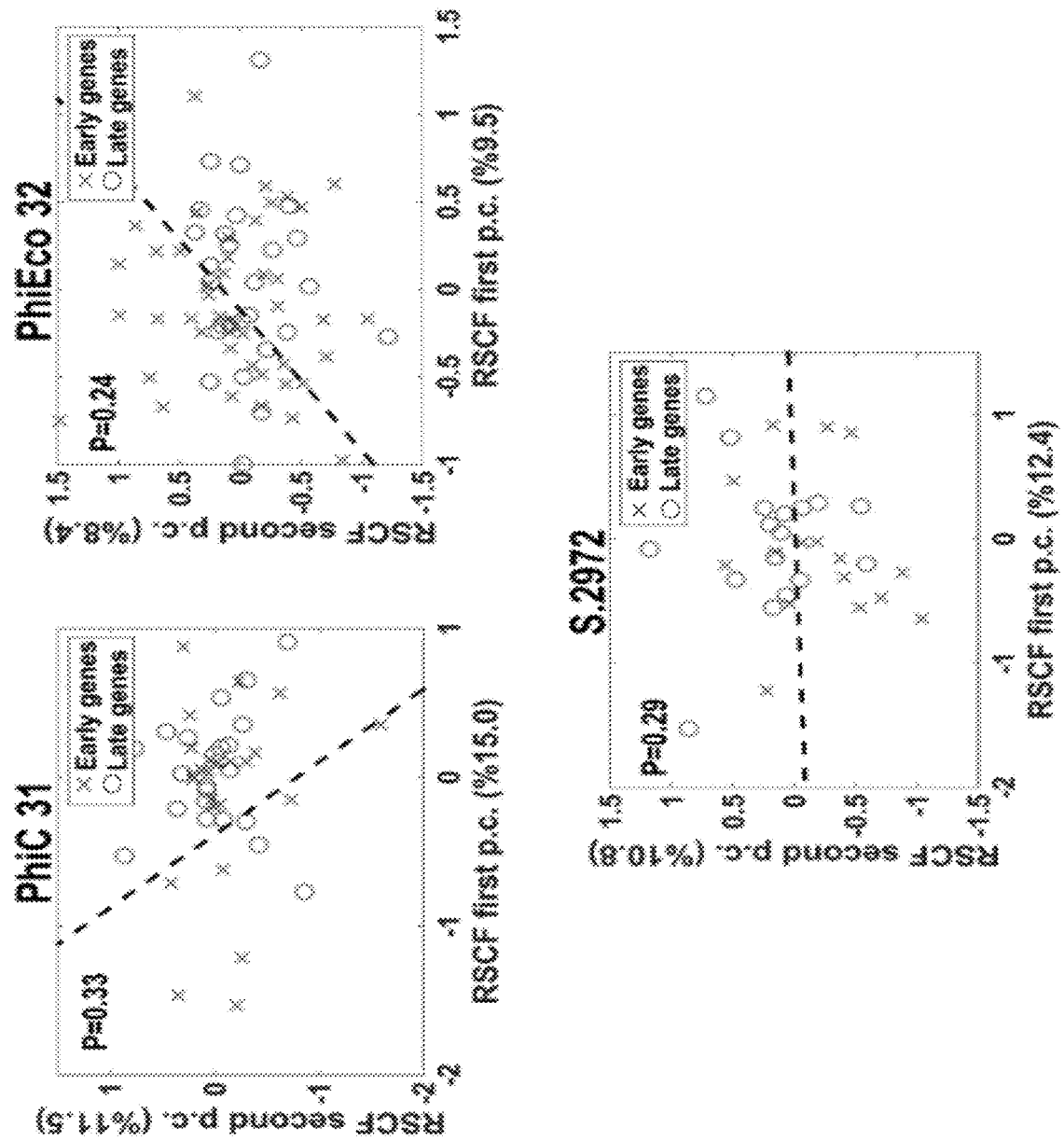
Figure 5E:
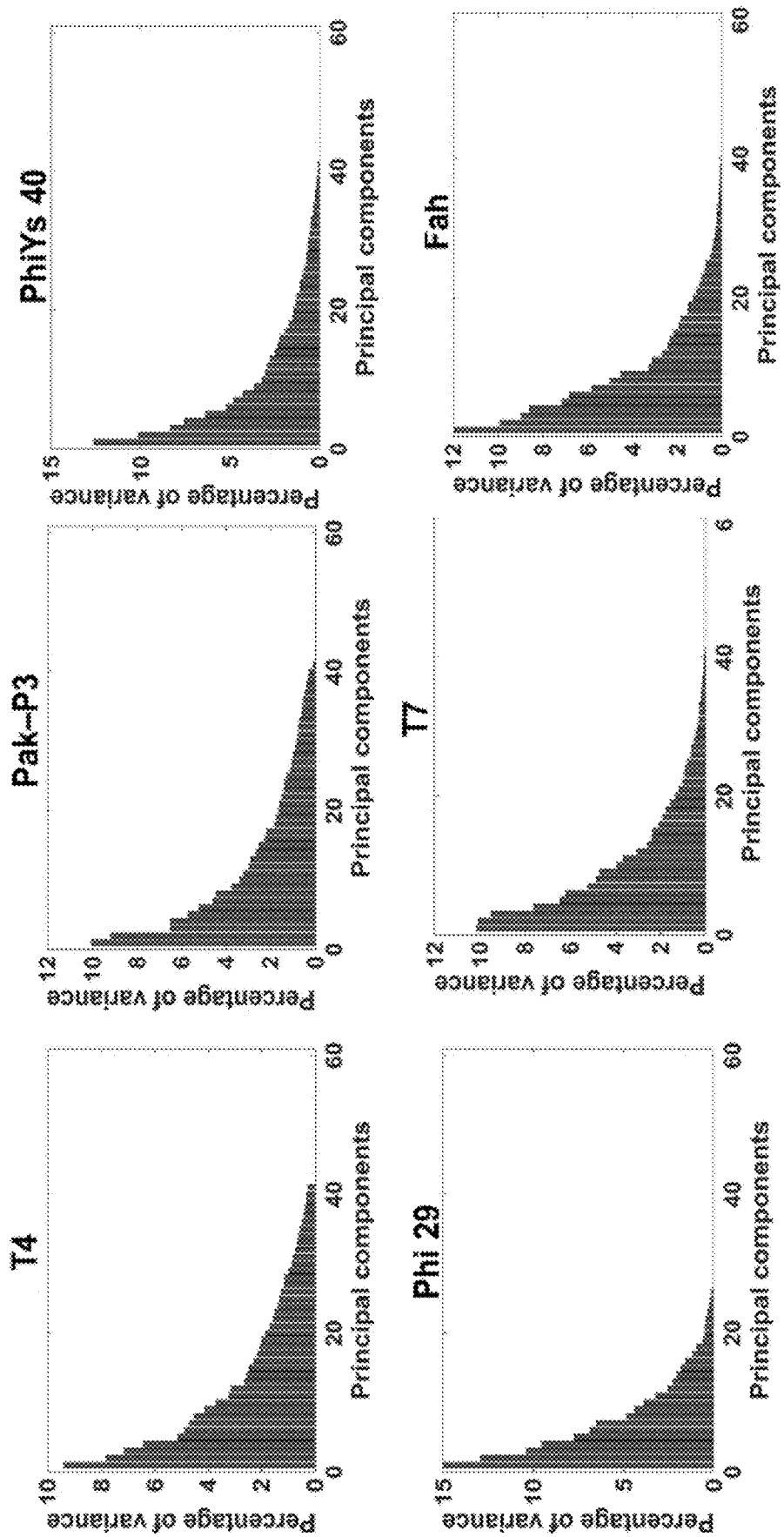
Figure 5E:
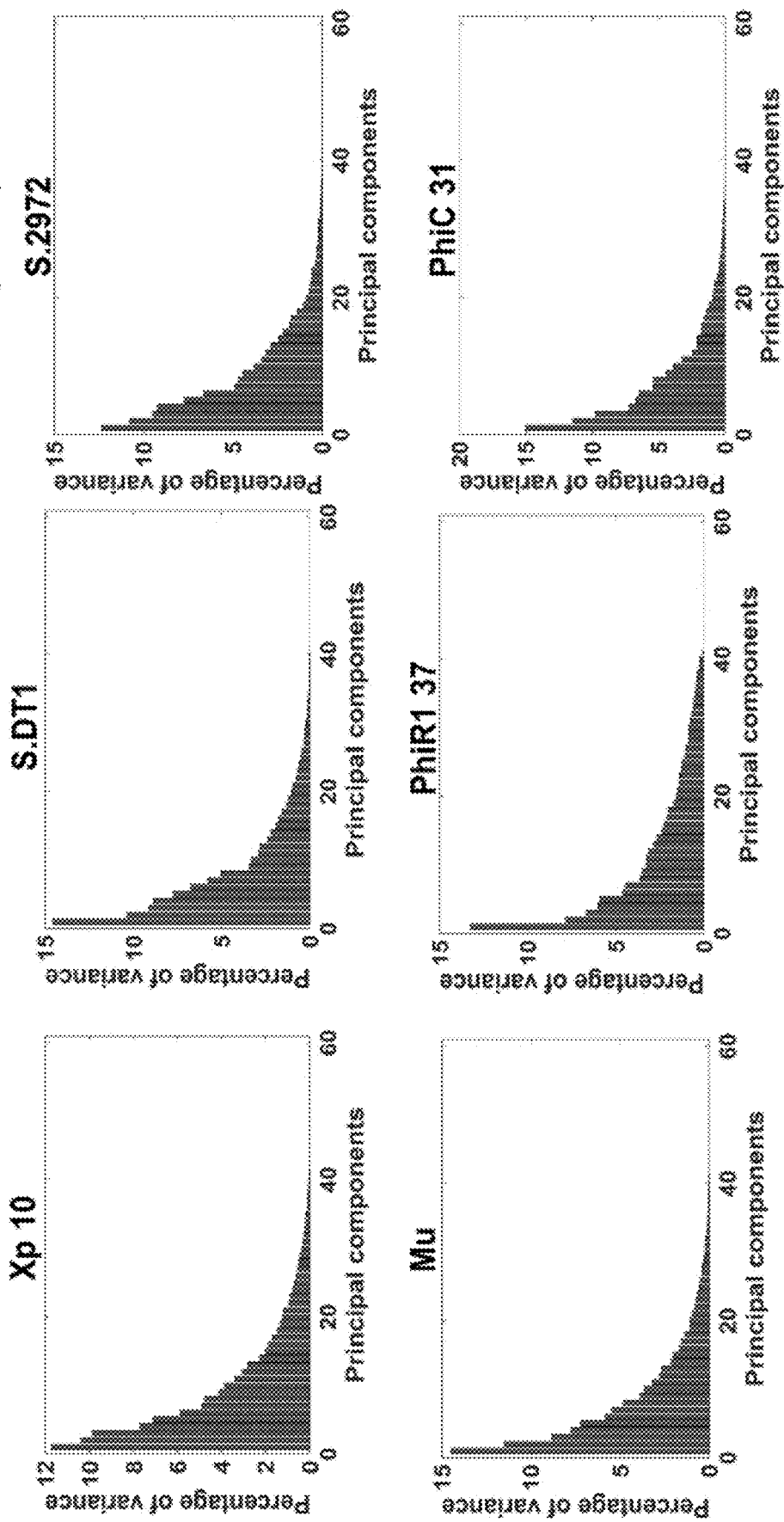
Figure 5E:
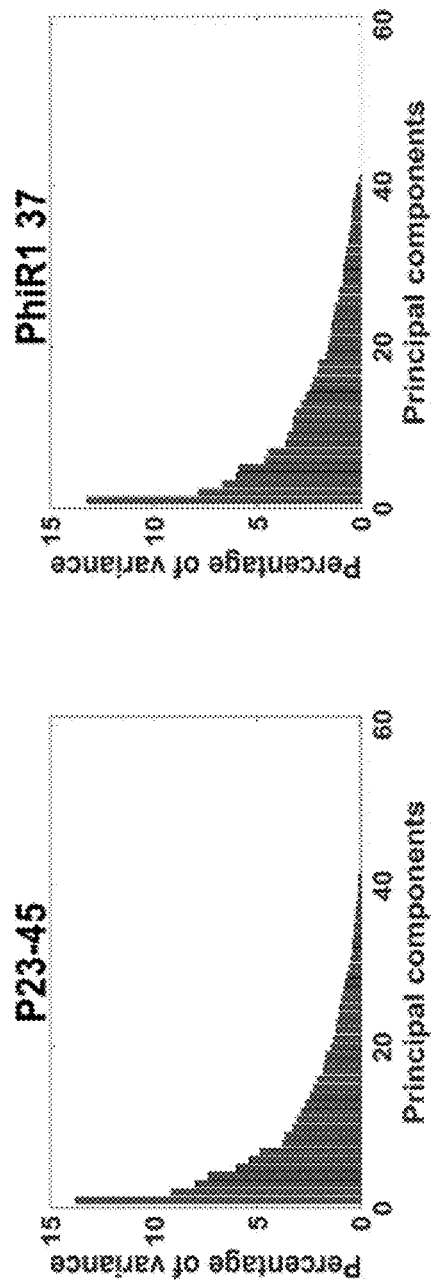

Results suggest that early and late genes in 50% of the analyzed bacteriophages tend to exploit different synonymous codons (Table 2). Specifically, in 7 of the 14 analyzed bacteriophages (FIG. 5A), early and late genes were found to be significantly (p-value≤0.05) separated according to the frequencies of their synonymous codons (FIG. 5B, top row). FIGS. 5C and 5D respectively show the principal component analysis (PCA) for the seven significantly separated phages and the seven that were not significantly separated. The PCS data for all 14 phages is also summarized in FIG. 5E. The analysis provides evidence that different sets of synonymous codons in early vs. late genes are selected for in the course of viral evolution; these differences may be related to the optimization of bacteriophage fitness in different phases of the viral lifecycles.

TABLE 2

Differential CUB of early and late genes in bacteriophages.

| Bacteriophage | Early-late clustering according to CUB | P-value |
| --- | --- | --- |
| T4 | Yes | 0.01 |
| Pak_P3 | Yes | <0.001 |
| phi29 | No | 0.19 |
| T7 | Yes | 0.05 |
| phiYs40 | Yes | 0.01 |
| Fah | No | 0.63 |
| xp10 | No | 0.12 |
| Streptococcus DT1 | No | 0.1 |
| Streptococcus 2972 | No | 0.29 |
| Mu | Yes | 0.01 |
| phiC31 | No | 0.33 |
| phiEco32 | No | 0.24 |
| p23-45 | Yes | <0.001 |
| phiR1-37 | Yes | <0.001 |

Figure 5F:
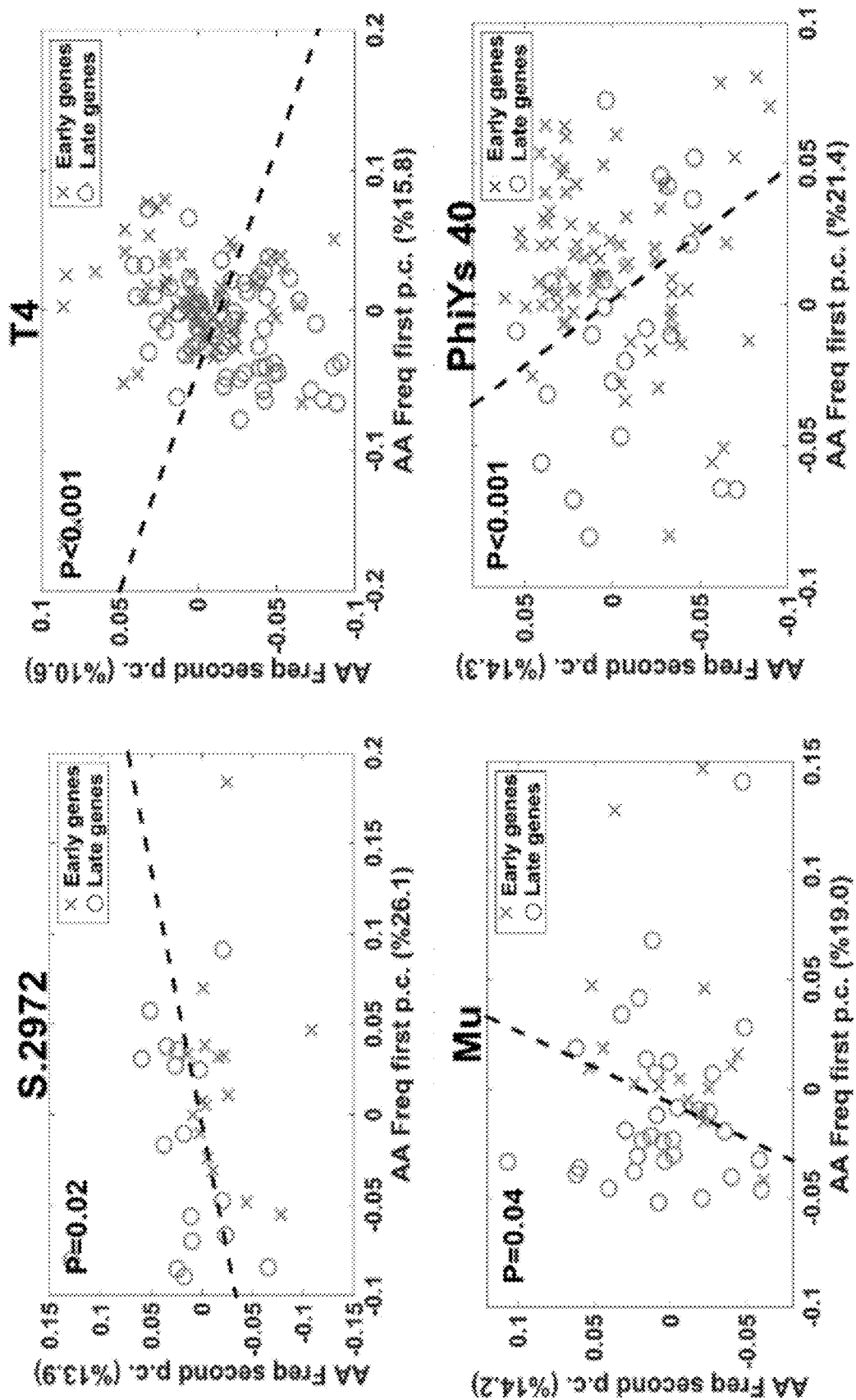
Figure 5F:
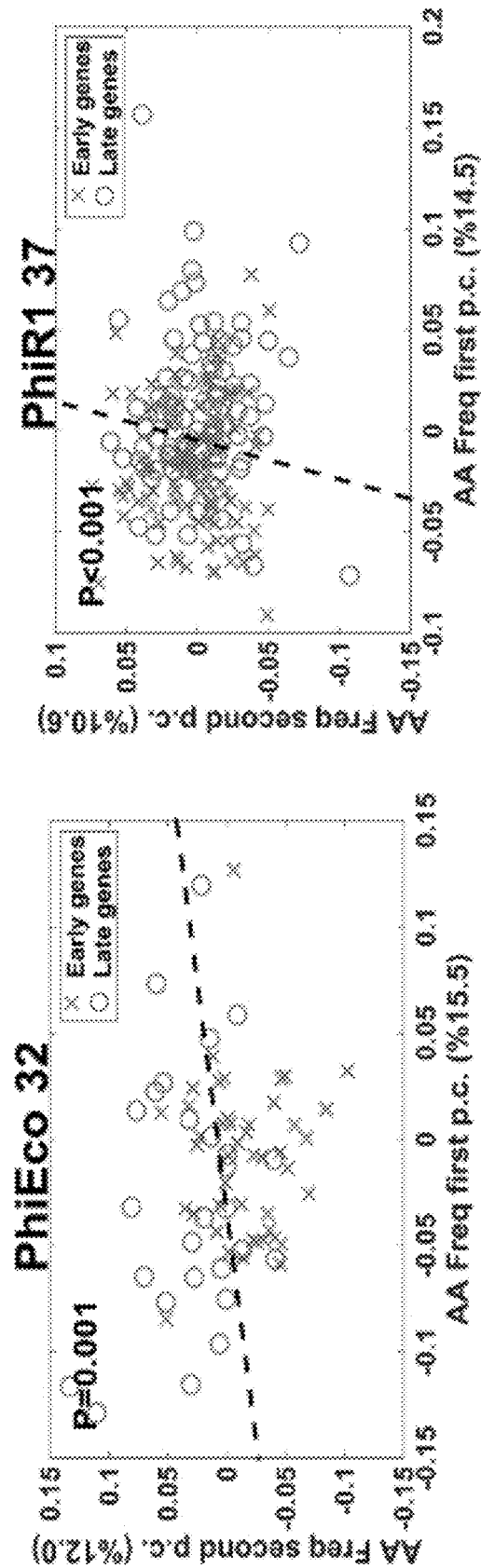
Figure 5G:
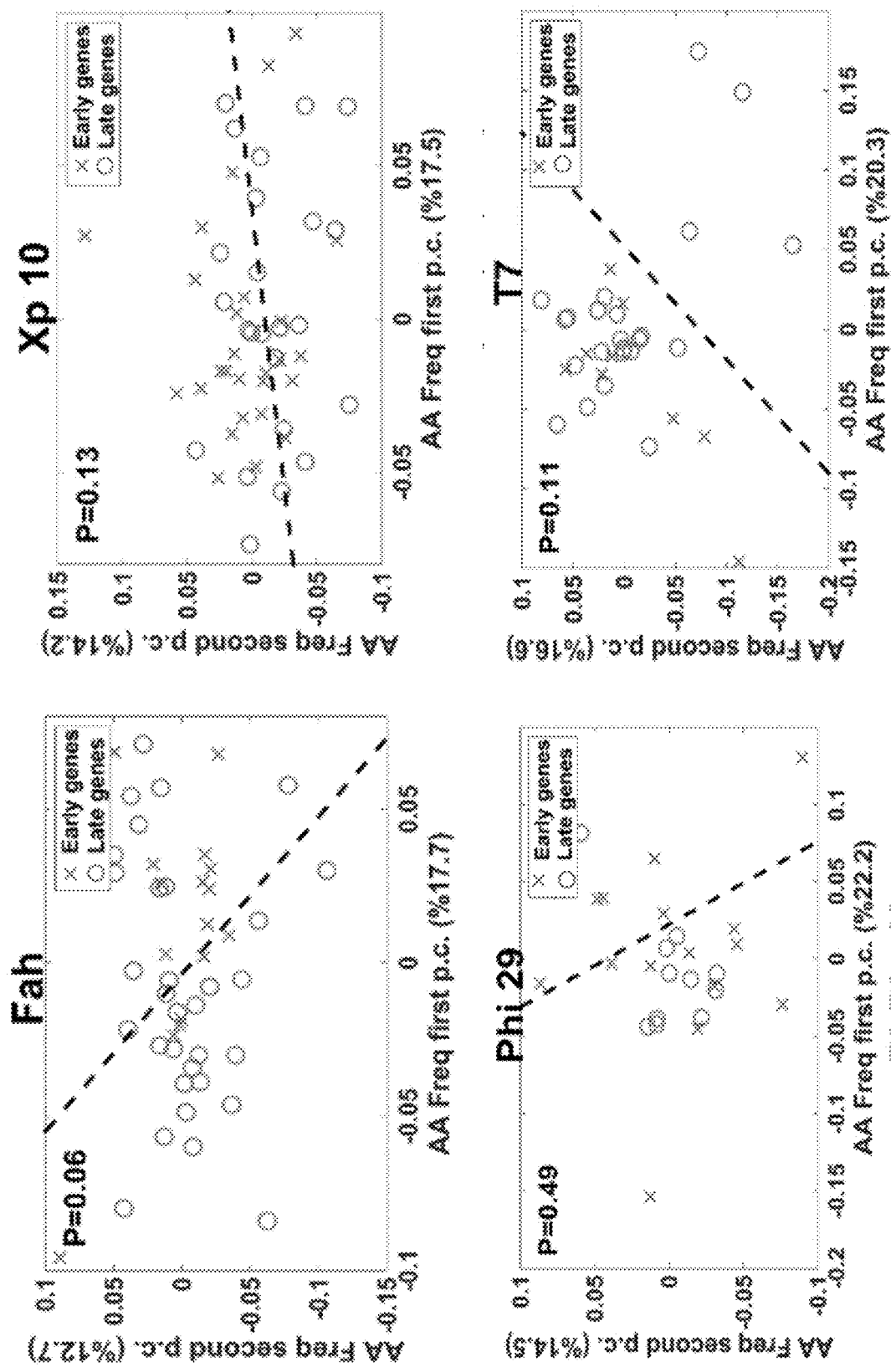
Figure 5G:
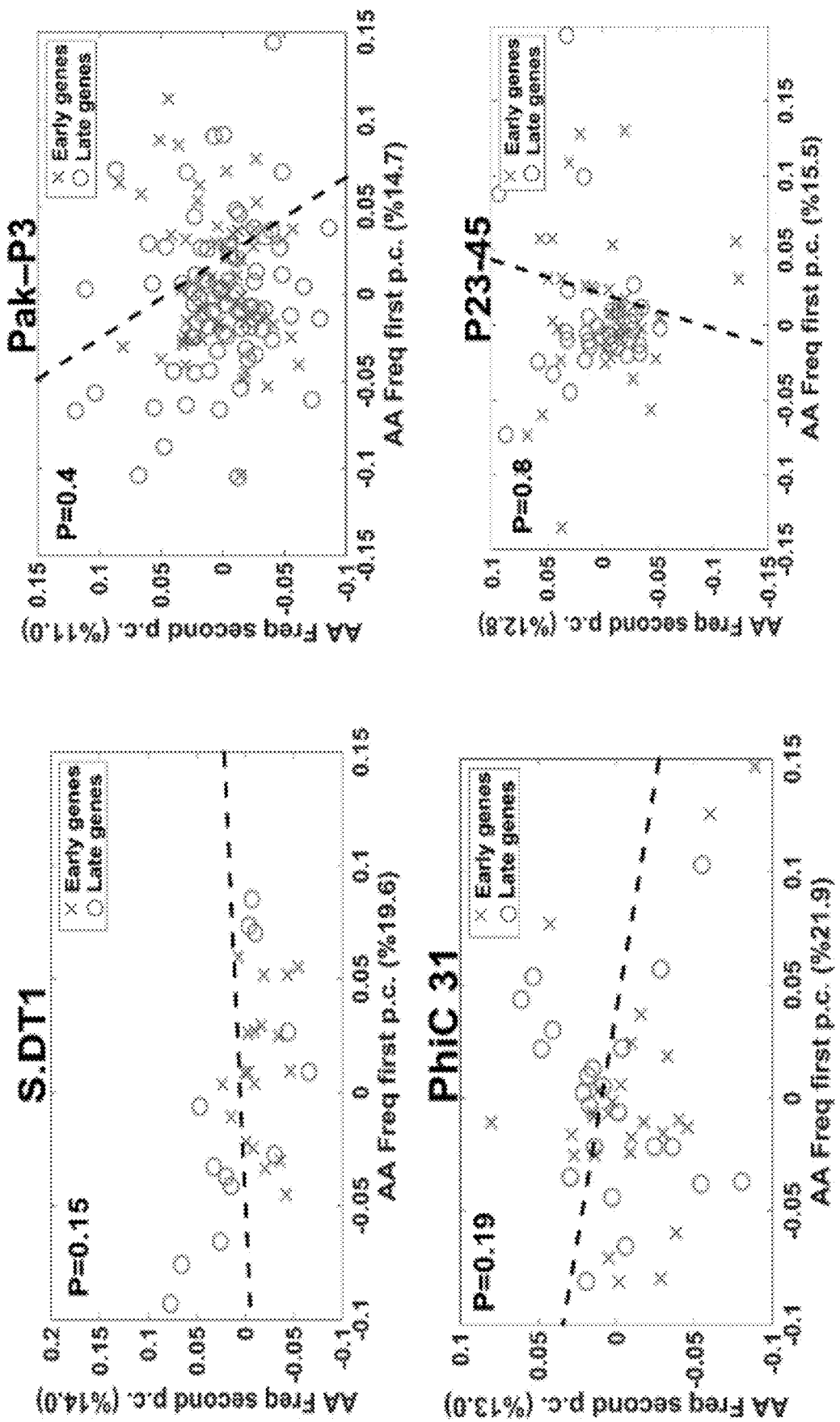
Figure 5H:
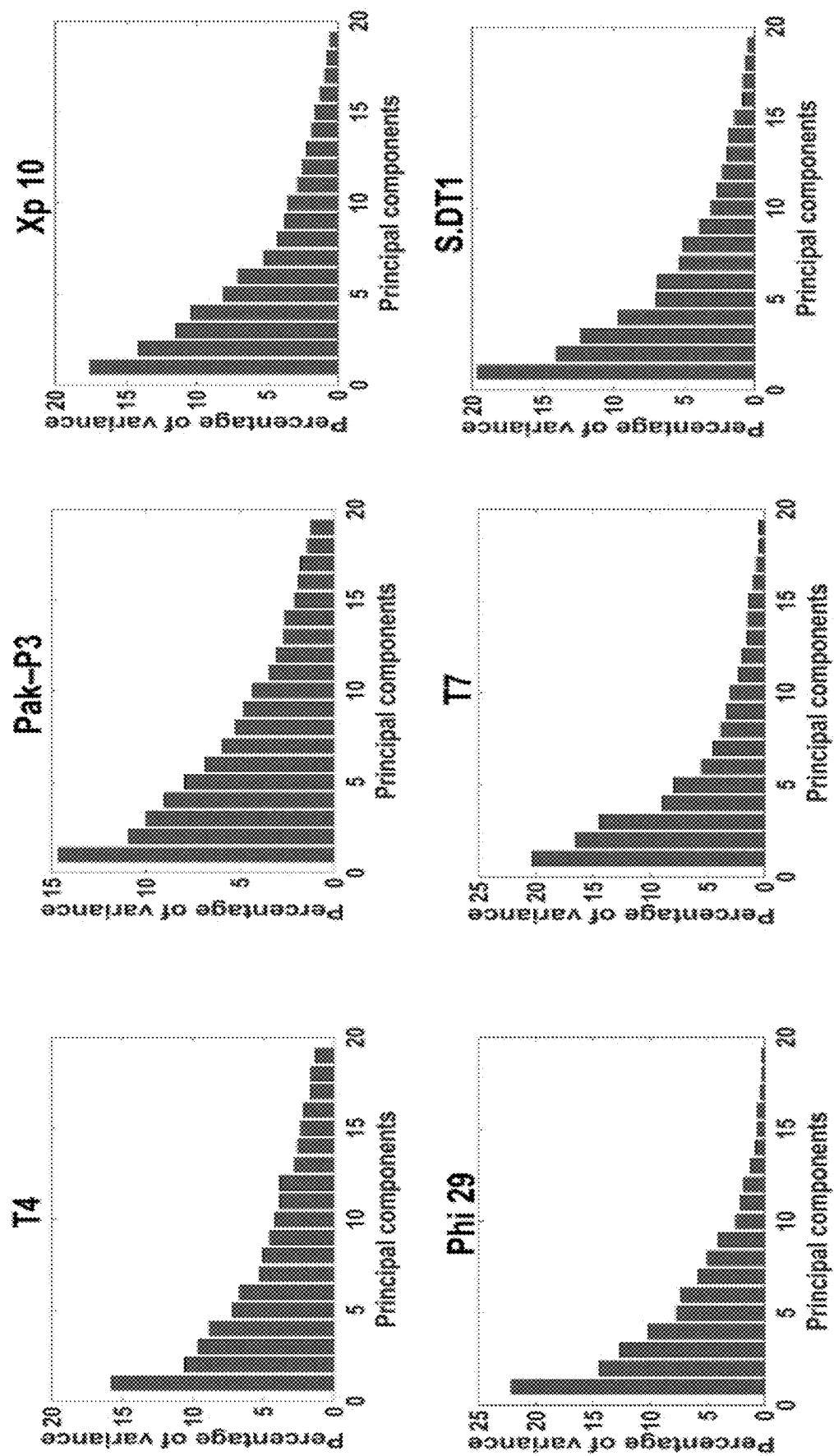
Figure 5H:
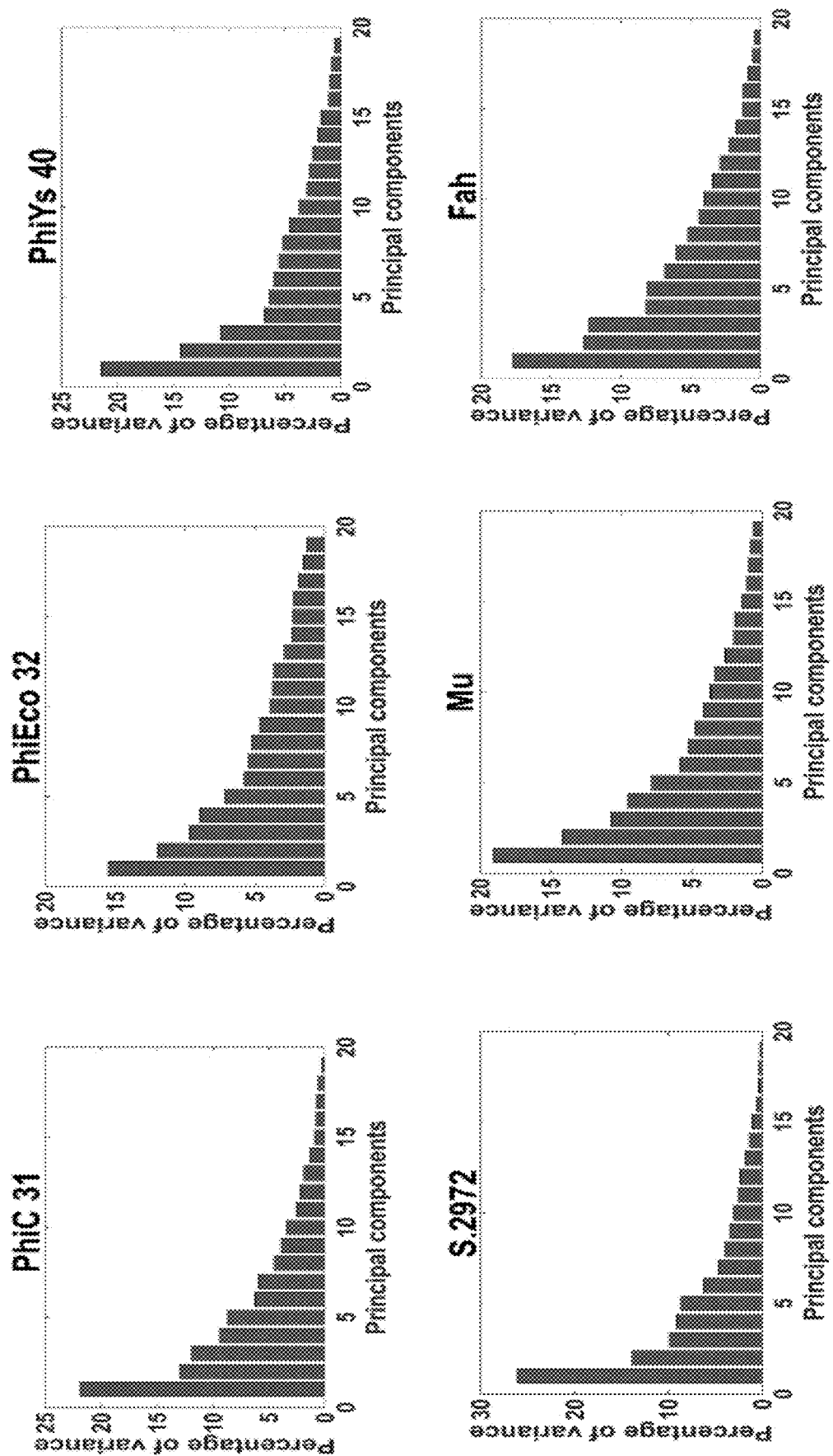
Figure 5H:
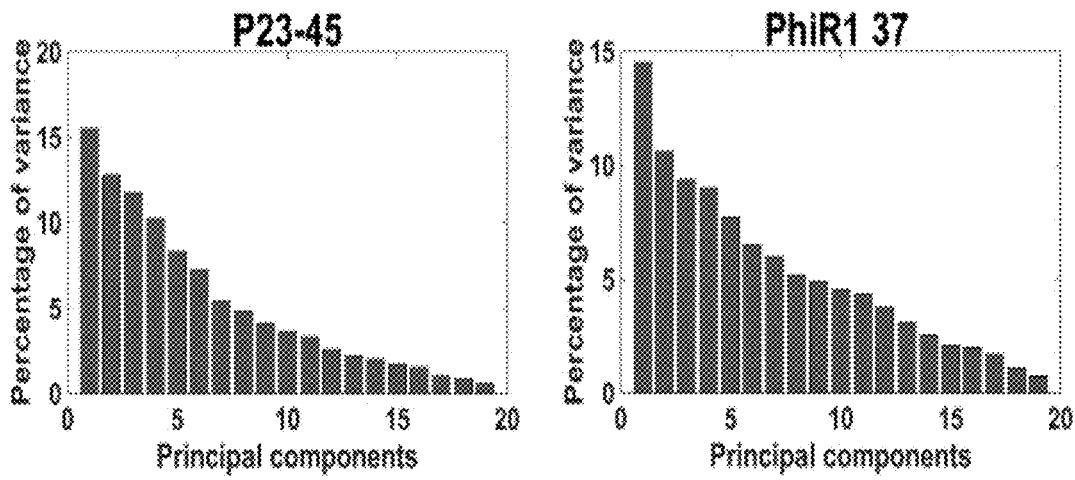

In addition, 6 out of 14 bacteriophages were also found to be significantly (p-value<0.05) separated according to the AA composition of their early and late genes (FIG. 5B, bottom row). FIGS. 5F and 5G respectively show the principal component analysis (PCA) for the six significantly separated phages and the eight that were not significantly separated. The PCS data for all 14 phages is also summarized in FIG. 5H. 4 viruses were characterized both by a differential synonymous codon usage and by a differential AA usage in their early and late genes. These findings suggest that among others, the different codon distribution in early and late genes may be partially related to the functionality of the encoded proteins via their AA content and possibly protein folding.

To check if bacteriophages with significant differences in synonymous codons usage in temporal genes tend to have more similar genomic sequences (usually related to smaller evolutionary distances), a phylogenetic tree was constructed of the bacteriophage proteomes based on Average Repetitive Subsequences (ARS) distance matrix and neighbor joining method as described in Materials and Methods section and in references therein (FIG. 5A). A statistical analysis was then performed in order to investigate the relation between the differences in temporal regulation of synonymous codons in different viruses and their evolutionary distances. In order to compare the distances between phages with the signal of temporary differential codon usage to the rest of the phages, the mean distance between all pairs of phages was compared with the signal to the distribution of mean pairwise distances in 100 randomly sampled groups of 7 viruses (the number of viruses in each sample is equal to the number of viruses in the test group). No significant differences in the test group as compared to the randomly sampled groups with respect to genomic similarity was found (empiric p-value=0.55).

Figure 6A:
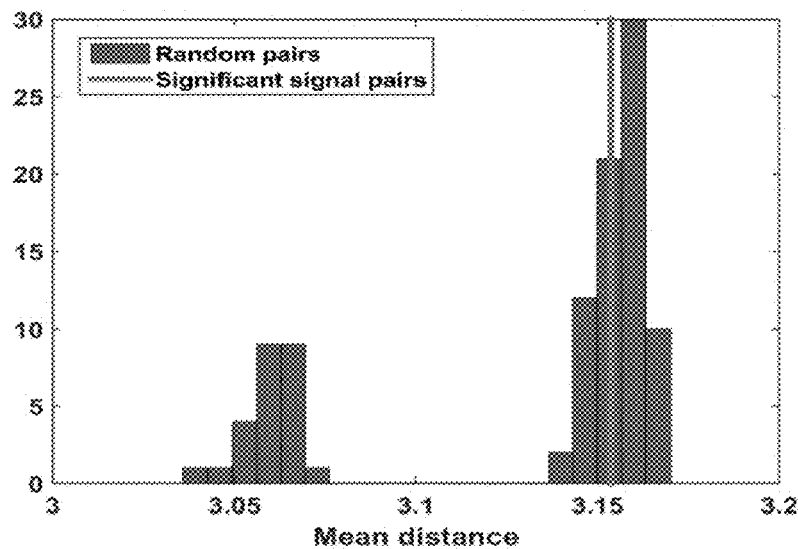
FIGS. 6A-B. Bar chart comparisons of a mean pairwise distance between the group of phages with a differential codon usage in temporal genes (light gray line) to 100 groups of randomly sampled phages of the same size (dark grey) for (A) all 14 phages and (B) all phages excluding one streptococcus.
Figure 6B:
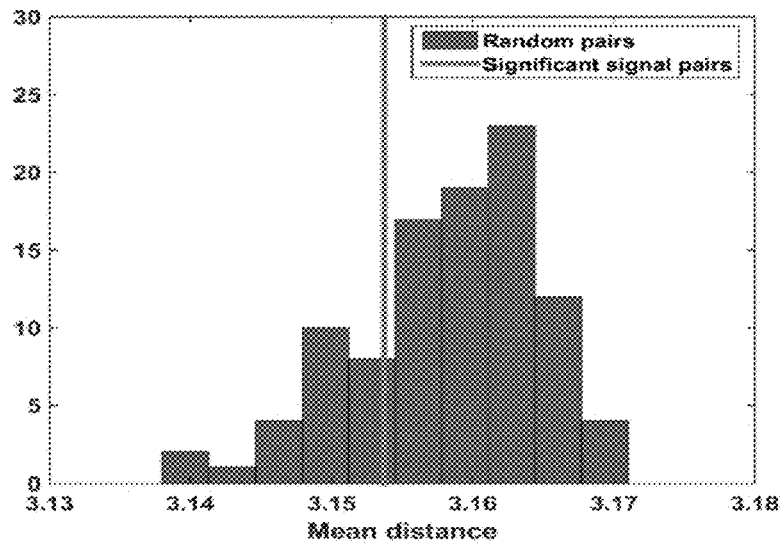

Due to the relatively high similarity between two types of streptococcus (DT1 and 2972), the distribution of mean pairwise distance in the randomly sampled groups was found to be bi-modal (FIG. 6A). Repeating a similar analysis after excluding one of the streptococcus, there was obtained a uni-modal distribution of random mean pair-distances; again, no significant differences in the test group as compared to the randomly sampled groups with respect to genomic similarity was found (empiric p-value=0.22, FIG. 6B). That no relationship was found suggests that the differential codon usage in early and late genes is a complex trait related to alternative determinants such as the bacterial niche, the specific phage proteins and their function/structure, etc.

Viruses undergo an extensive evolutionary selection for adaptation to their host's cell environment, and thus it can be assumed that their codon composition reflects an efficient adaptation of the viral genes to specific intracellular conditions (e.g. in terms of gene expression factors such as tRNA molecules, AA concentration, etc) that are prevalent in different gene expression stages, in accordance with the reported results.

Example 6

Figure 7:
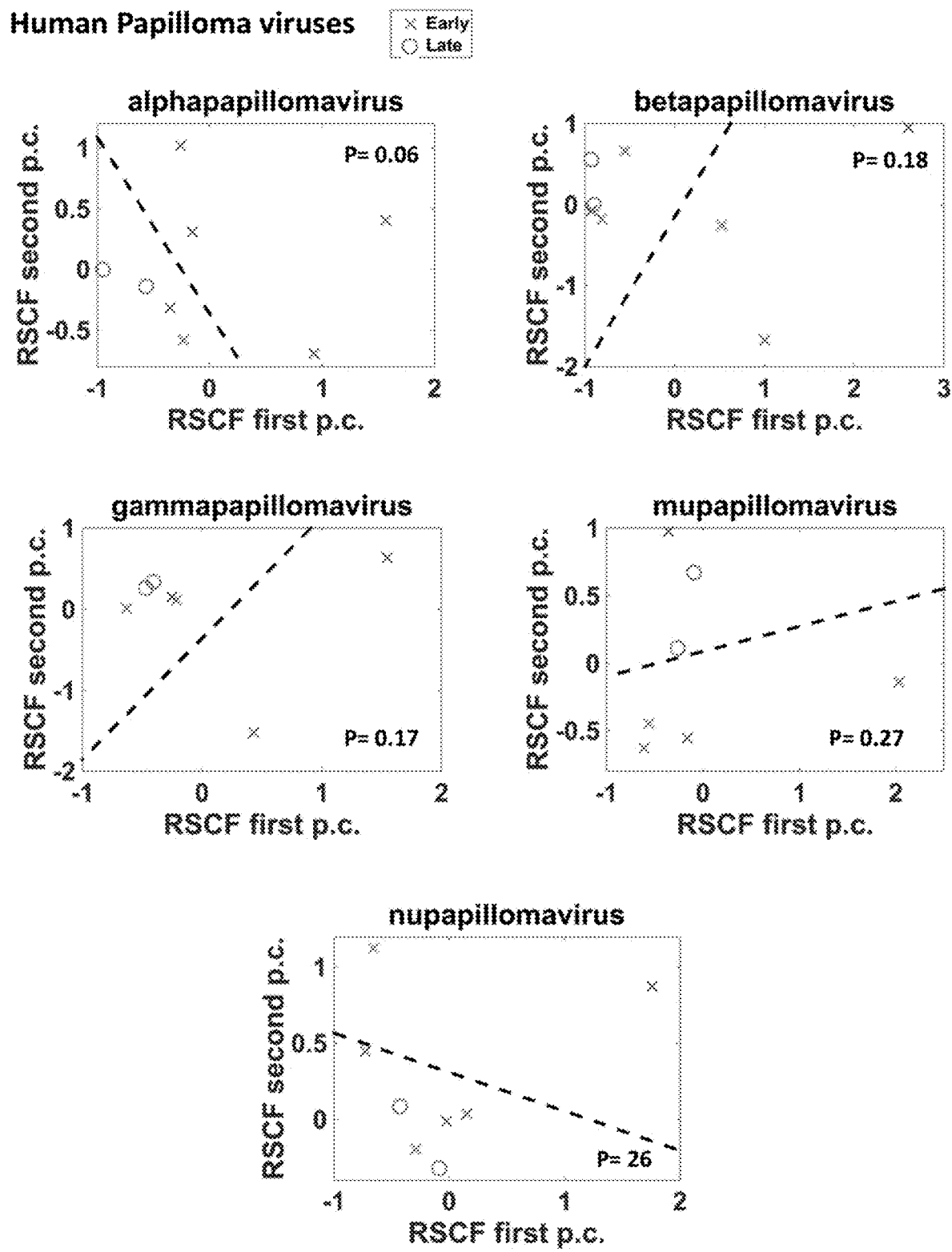
FIG. 7. Scatter plots of the CUB principal component analysis (PCA) for human viruses.
Figure 7:
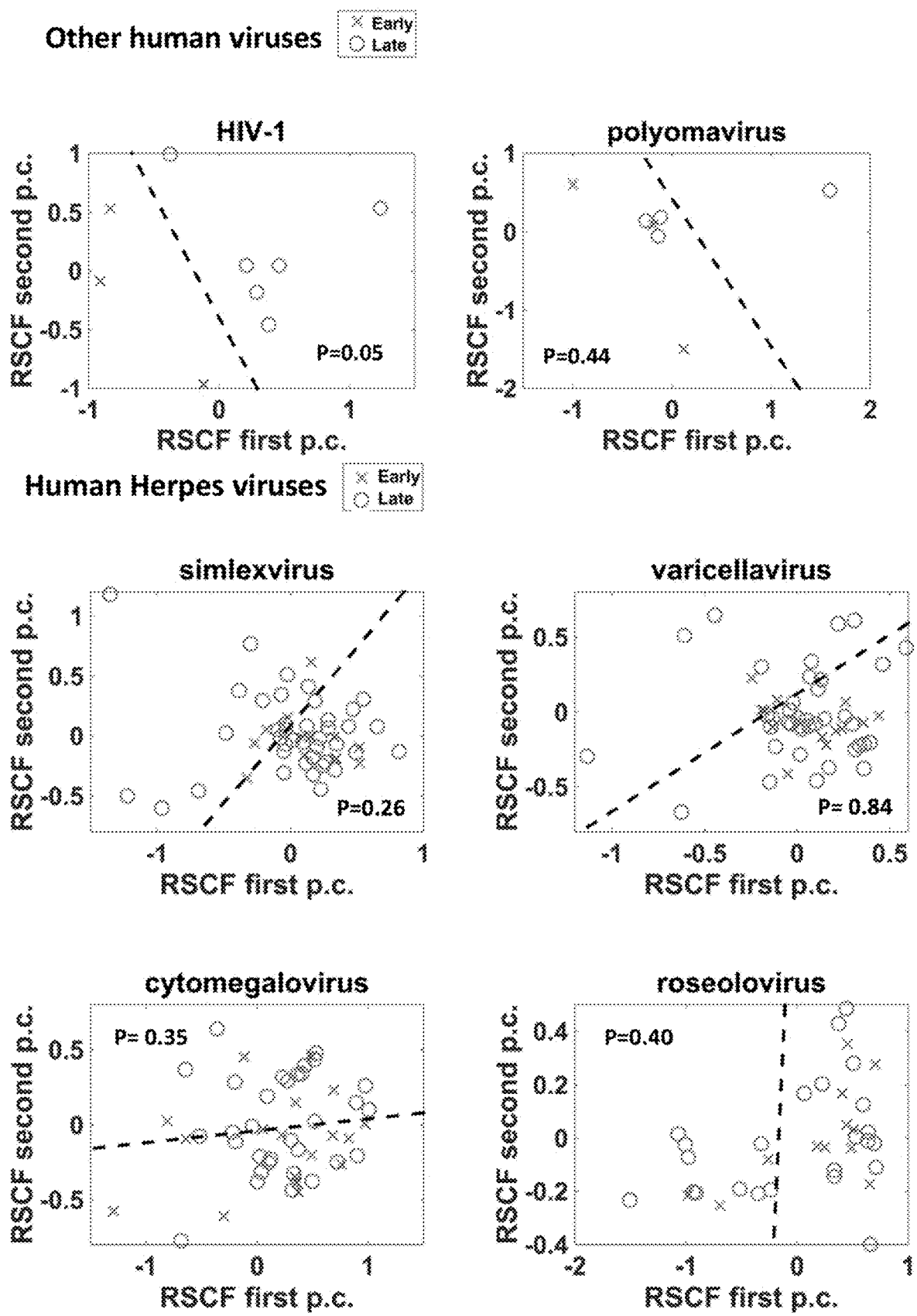

Weaker Separation Between Synonymous Codon Usage in Early and Late Genes in Human Viruses The results in the previous section suggest that bacteriophages undergo an extensive evolutionary selection on a synonymous level for temporal regulation of gene expression. The extent to which this also occurs in viruses of humans and other eukaryotic hosts was harder to ascertain. Human Immunodeficiency Virus 1 (HIV-1) was found to have a significant separation (p-value≤0.05) of codon composition between early and late genes, while such separation was not statistically significant in the rest of the analyzed viruses (Table 3). FIG. 7 shows the principal component analysis (PCA) for the 11 human viruses.

TABLE 3

Weak evidence of differential synonymous codon usage bias in early and late genes in human viruses.

| Virus | Early-late separation according to CUB | p-value | Early-late separation according to AAB | p-value |
|---|---|---|---|---|
| Simplex virus | No | 0.25 | No | 0.19 |
| Varicello virus | No | 0.85 | Yes | 0.02 |
| Cytomegalo virus | No | 0.35 | Yes | 0.03 |
| Roseolo virus | No | 0.37 | No | 0.68 |
| Alphapapilloma virus | No | 0.08 | No | 0.17 |
| Betapapilloma virus | No | 0.18 | No | 0.9 |
| Gammapapilloma virus | No | 0.14 | No | 0.09 |
| Mupapilloma virus | No | 0.29 | No | 0.29 |
| Nupapilloma virus | No | 0.29 | No | 0.5 |
| Polyoma virus | No | 0.45 | No | 0.7 |
| HIV-1 | Yes | 0.04 | No | 0.21 |

As evidenced in Table 4, human viruses tend to have fewer genes than bacteriophages. Therefore, it was checked whether this fact can explain the weaker signal for temporal separation in CUB, and if, in practice, human viruses may also behave as bacteriophages with respect to the differential usage of synonymous codons in their early and late genes. To this end the 7 bacteriophages with temporary differential codon usage were analyzed by sampling in each one of them the number of early and late genes that is typical to human viruses (average of 8 early genes and 14 late genes). It was found that the temporal differences in codon usage remained significant even after randomly reducing the number of genes, indicating, among others, that these differences cannot be directly explained only by the genome size

TABLE 4

Genomic properties of different viruses

| Virus | Host | Number of genes Early | Number of genes Late | Average genes length Early | Average genes length Late | Average ENC Early | Average ENC Late |
|---|---|---|---|---|---|---|---|
| Phages | | | | | | | |
| T4 | E. coli | 64 | 64 | 589.4 | 1009.0 | 34.37 | 37.36 |
| Pak_P3 | Pseudomonas aeruginosa | 51 | 83 | 311.8 | 641.6 | 35.25 | 38.20 |
| phi29 | Bacillus subtilis | 16 | 11 | 396.4 | 1084.6 | 35.92 | 44.16 |
| T7 | E. coli | 10 | 24 | 635.1 | 905.6 | 35.74 | 39.84 |
| phiYs40 | Thermus thermophilus | 79 | 22 | 602.8 | 1623.3 | 35.92 | 37.21 |
| Fah | Bacillus cereus | 16 | 32 | 679.1 | 707.5 | 36.36 | 35.38 |
| xp10 | Xanthomonas oryzae | 27 | 24 | 605.7 | 880.0 | 40.61 | 42.01 |
| Streptococcus DT1 | Streptococcus thermophilus | 19 | 14 | 519.6 | 1038.2 | 37.90 | 37.15 |
| Streptococcus 2972 | Streptococcus thermophilus | 16 | 17 | 528.8 | 1009.8 | 37.28 | 38.05 |
| Mu | E. coli | 16 | 34 | 492.6 | 767.6 | 38.05 | 39.50 |
| phiC31 | Streptomyces coelicolor | 27 | 22 | 552.1 | 820.0 | 33.03 | 36.08 |
| phiEco32 | E. coli | 45 | 27 | 363.9 | 1108.4 | 34.85 | 38.81 |
| p23-45 | Thermus thermophilus | 40 | 33 | 464.6 | 1196.6 | 35.76 | 37.61 |
| phiR1-37 | Yersinia enterocolitica | 92 | 97 | 284.3 | 825.3 | 31.38 | 34.80 |
| Human viruses | | | | | | | |
| Simplex virus | Human | 13 | 40 | 2143.2 | 1641.5 | 39.00 | 38.23 |
| Varicello virus | | 13 | 39 | 1989.5 | 1632.3 | 51.04 | 49.25 |
| Cytomegalo virus | | 18 | 32 | 1735.8 | 1657.7 | 41.00 | 41.96 |
| Roseolo virus | | 12 | 24 | 1914.0 | 1599.4 | 49.79 | 47.60 |
| Alphapapilloma virus | | 6 | 2 | 673.0 | 1470.0 | 37.04 | 40.62 |
| Betapapilloma virus | | 6 | 2 | 899.5 | 1554.0 | 39.26 | 44.44 |
| Gammapapilloma virus | | 5 | 2 | 856.2 | 1558.5 | 39.63 | 42.64 |
| Mupapilloma virus | | 5 | 2 | 779.4 | 1525.5 | 39.08 | 45.21 |

TABLE 4-continued

Genomic properties of different viruses

| Virus | Host | Number of genes | | Average genes length | | Average ENC | |
|---|---|---|---|---|---|---|---|
| | | Early | Late | Early | Late | Early | Late |
| Nupapilloma virus | | 6 | 2 | 728.0 | 1708.5 | 42.93 | 49.96 |
| Polyoma virus | | 3 | 4 | 908.0 | 762.0 | 35.68 | 38.52 |
| HIV-1 | | 3 | 6 | 411.0 | 1583.5 | 40.06 | 38.76 |

Example 7

Comparison of Early and Late Genes with Respect to Additional Features of Their Coding Regions The signal of selection for temporarily regulated composition of synonymous codons in bacteriophages demonstrated in the previous subsection led to the analysis of additional genomic features, such as: codon mean typical decoding rate (MTDR), tRNA adaptation index (tAI), codon pairs bias (CPB), dinucleotide bias (DNTB), nucleotide bias (NTB), GC content and amino acids bias (AAB). Various studies have related these features to different genomic mechanisms and biological processes involved in viral replication cycles and viral fitness.

For example, it has been suggested that gene translation efficiency can be affected not only by single codons, but also by distribution of codon pairs. It has been argued that pairs of adjacent nucleotides may be an important genomic characteristic being under a significant evolutionary pressure in viruses and their hosts; specifically, it was suggested that CpG pairs are under-represented in many Ribonucleic Acid (RNA) and in most small human DNA viruses, in correspondence to dinucleotide frequencies of their hosts. This phenomenon can be related, for example, to the contribution of the CpG stacking basepairs to RNA folding and/or to the enhanced innate immune responses to viruses with elevated CpG. The stability of the RNA secondary structures can also be affected by the genomic composition of nucleotides and in particular by GC content. In addition, nucleotide compositions and AA usage bias may affect, among others, the synthesis of viral molecules, and the function and structure of the encoded proteins.

Figure 8A:
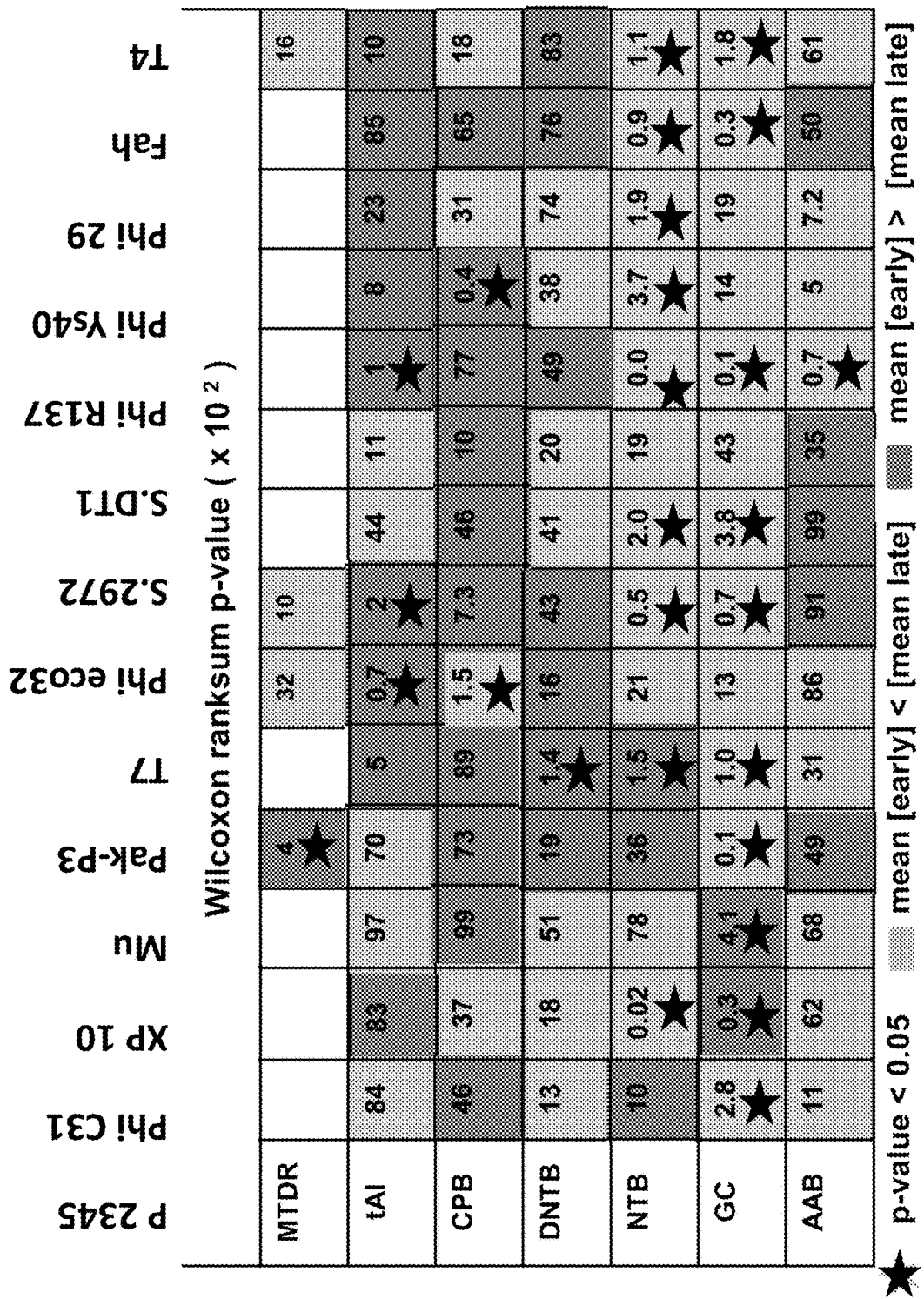
FIGS. 8A-H. (A) Table showing significance of separation between early and late genes with respect to additional genomic features estimated by Wilcoxon ranksum p-value. Features/viruses with significant (p-value<0.05) separation between the two temporal groups are marked by yellow stars; green is related to higher mean in the case of the early genes and red is related to higher mean in the case of the late genes. (B-H) Bar chart comparisons of (B) genome length, (C) ENC, (D) CPB, (E) DNTB, (F) NTB, (G) GC content and (H) AAB in viruses with significant temporal separation in codon usage bias (blue) vs. viruses with no such separation (grey). Y axis—probability; X—genomic mean feature values (each virus is represented by an average of feature values over all its genes). Wilcoxon ranksum p-values are specified.

Consequently, the above listed features were estimated for all genes in all viruses, and the separation between early and late genes with respect to each one of them was evaluated (see Materials and Methods). The results shown in FIG. 8A suggest that the differential usage of synonymous codons in early and late genes can be partially related to temporal differences in various characteristics of genomic sequences. Specifically, the features with the strongest temporal differences are the NTB and GC content which are significant (p-value<0.05) in most of the phages.

Figure 8B:
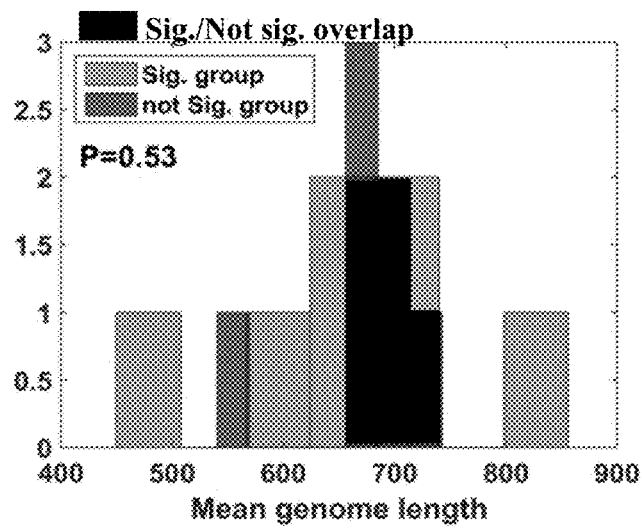
Figure 8C:
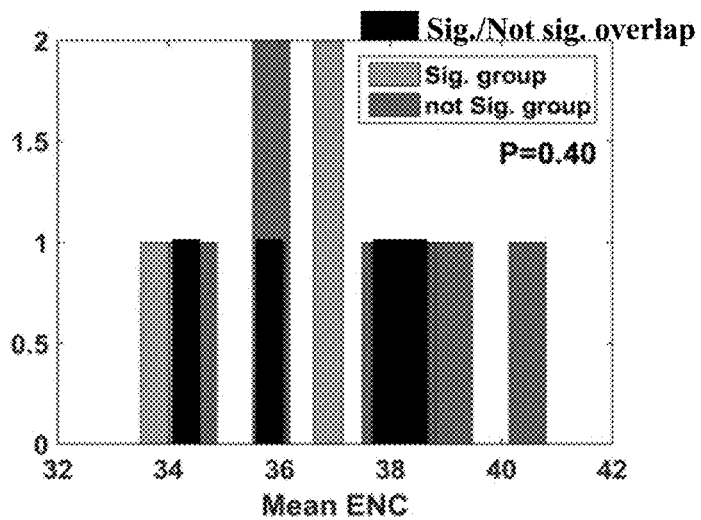
Figure 8D:
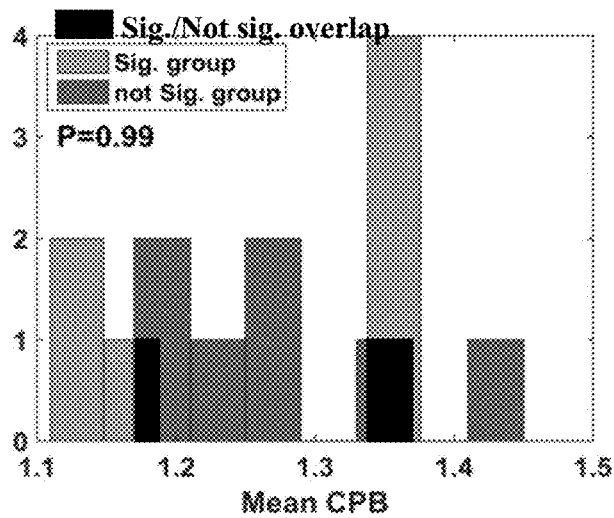
Figure 8E:
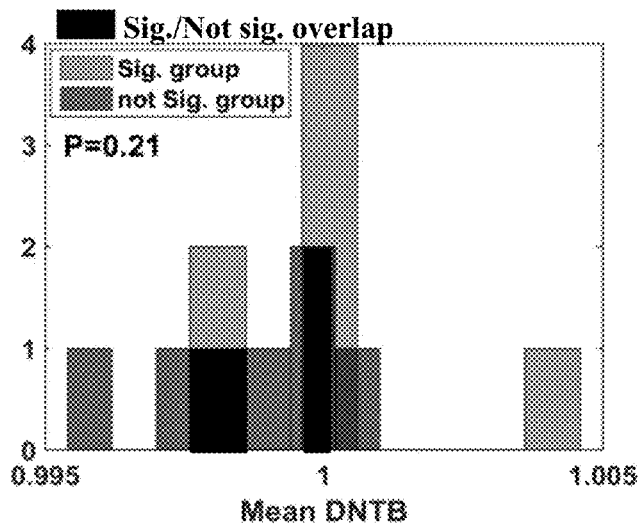
Figure 8F:
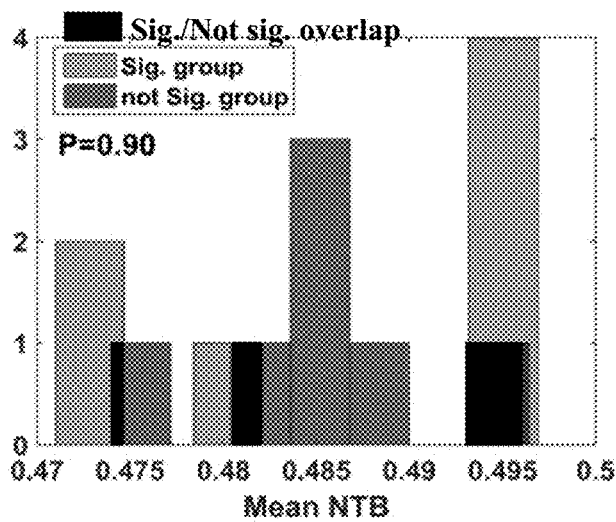
Figure 8G:
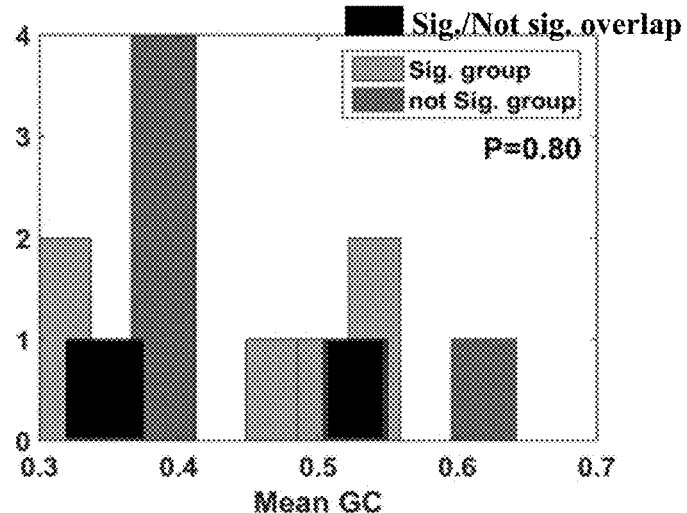
Figure 8H:
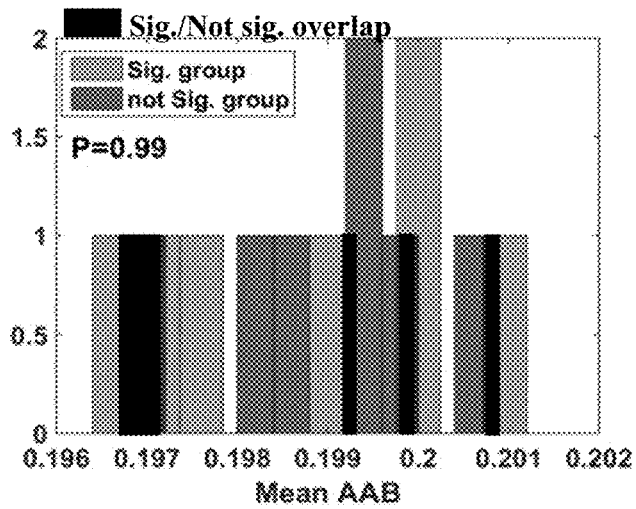
Figure 9:
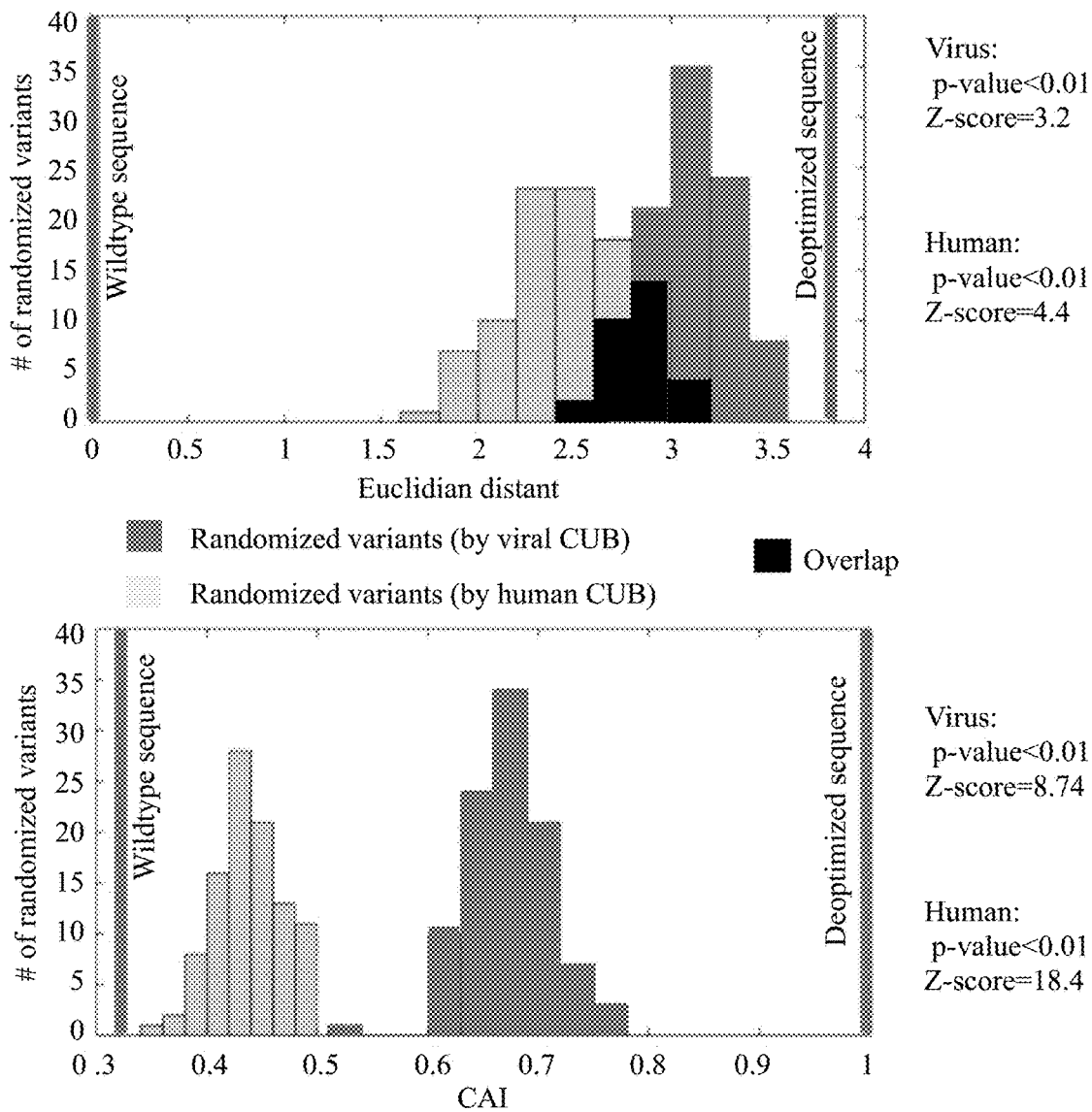
FIG. 9. Evaluation of human IL2 gene optimization using Eucledian distance D and CAI. Bar charts depicting IL2 gene optimization. Optimized evaluation values D(s,t)=3.84, CAI(t,R)=1 are given by "optimized variant" bars. Wild type evaluation values D(s,s)=0, CAI(s,R)=0.32 are given by "Wild type sequence" bars. D(x,y)—Euclidian distance between synonymous codons relative frequency vectors of sequences x and y; CAI(x,R)/RCDI(x,R)—CAI/RCDI of sequence x with respect to the reference set R; s/t—wild-type/optimized IL2 coding sequences. The distribution of D/CAI/RCDI values are given for variants randomized with respect to the average viral CUB and to the average human CUB. P-value and Z-score estimations with respect to each random model is specified.

In addition, if the bacteriophages with a significant temporal separation with respect to synonymous codons tend also to be enriched with specific genomic features in comparison to the group of bacteriophages with non-significant temporal differences in synonymous codons was checked. To this end, the distribution of various genomic features in the two groups was compared. Based on Wilcoxon ranksum test no significant differences were found between the two groups of bacteriophages in terms of: genome length (p-value=0.53, FIG. 8B), ENC (p-value=0.4, FIG. 8C), CPB (p-value=0.99, FIG. 8D), DNTB (p-value=0.21, FIG. 8E), NTB (p-value=0.9, FIG. 8F), GC content (p-value=0.8, FIG. 8G) and AAB (p-value=0.99, FIG. 8H).

Taken together these results demonstrate that viruses undergo an extensive evolutionary selection on a synonymous level for temporal regulation of gene expression.

Example 8

Rational Design of Optimized Genes Based on Expression Period

Based on the above findings, that codon bias at defined periods of a virus's life cycle could enhance translational elongation and thus expression, it was hypothesized that genes (viral genes, human genes, heterologous transgenes) could be designed that would have optimized codons and that would result in maximal protein expression during a defined time period. To achieve this, codons would be selected with frequencies more similar to the set of early or late genes than a random set of genes. This similarity could be based on any metric of codon bias e.g. KL distance, Euclidean distance, L1, etc. or on any codon bias indexes (e.g. CAI).

To achieve this, the following mathematical algorithm was employed:

Input:

Target sequence t: a wild-type endogenous viral coding sequences or a coding sequence originating in some heterologous transgene.

A set of reference sequences R: viral coding sequences grouped by expression period (early/late/intermediate)

Output:

A reengineered variant s of the target sequence t such that s and t code for the same protein and the codons fit to one of the stages: early/late/intermediate.

1. For each sequence k in the reference set R:

1.1 For each amino acid A:

compute the relative frequencies of synonymous codons:

$$F^k(C_{A,j}) = \frac{q_{A,j}}{\sum_{j=1}^{m} q_{A,j}}, \sum_{j=1}^{m} F(C_{A,j}) = 1$$

(where $\{C_{A,j}\}_{j=1}^{m}$ are m synonymous codons of said amino acid A; $q_{A,j}$ is the number of appearances of codon $C_{A,j}$ in the processed sequence; the superscript k stands for "the k-th reference sequence)

1.2. For each amino acid, A, compute the average relative frequencies of its synonymous codons over all sequences in R:

$$F(C_{A,j}) = \frac{1}{|R|}\sum_{k=1}^{|R|} F^k(C_{A,j})$$

2. Initialize the re-engineered sequence s into the wild-type sequence t:

$$s \leftarrow t$$

3. For each codon $C_{A,i}$ in s:
Replace $C_{A,i}$ with a synonymous codon $C_{A,j}$ according to the synonymous rule $$C_{A,j} = \arg\max_{C_{A,k}} F_A(C_{A,k}).$$

4. Estimate the optimization level L(s) using one of the following:
Euclidian distance between two vectors representing relative synonymous codons frequencies of $s_1$ and $s_2$ (RSCF vectors); or
Codon Adaptation Index with respect to R (Sharp P M et al., Nucleic Acids Research, 1987 15, 1281-95).

Data on the average early/late relative codon frequencies of several bacteriophages and viruses appear in Appendix 1.

This codon optimization was performed on the human interleukin 2 gene with respect to the set of Simplex virus early genes. That is, human IL2 was recoded using the most frequent synonymous codons found in the Simplex virus early genes. This will maximize expression of IL2 protein during the early period of the Simplex virus life cycle.

The viral genome was downloaded from www.ncbi.nlm-.nih.gov/nuccore/NC_001806.2, using the GenBank accession number NC_001806.2.

The coding sequence of human gene IL2 was downloaded from https://www.ncbi.nlm.nih.gov/nuccore/NM_000586, using GenBank accession number NM_000586.

The optimized variant was engineered using the above algorithm with the following inputs/definitions:

S=wild-type coding sequence of human gene IL2

R={UL2, UL5, UL8, UL12, UL23, UL29, UL30, UL39, UL40, UL42, UL50, UL52, US3}—a reference set of Simplex virus early genes.

The synonymous rule is defined as: substitute each wild type codon with the most frequent codon in R. Codons frequencies are given in Appendix 1.

The optimization evaluation function L was defined as: (1) Euclidean distance; (2) Codon Adaptation Index (CAI)

The following optimized sequence was produced:

```
t =
                                          (SEQ ID NO: 1)
ATGTACCGCATGCAGCTGCTGAGCTGCATCGCCCTGAGCCTGGCCCTGGT

GACCAACAGCGCCCCCACCAGCAGCAGCACCAAGAAGACCCAGGTGCAGC

TGGAGCACCTGCTGCTGGACCTGCAGATGATCCTGAACGGGATCAACAAC

TACAAGAACCCCAAGCTGACCCGCATGCTGACCTTTAAGTTTTACATGCC
```

-continued

```
CAAGAAGGCCACCGAGCTGAAGCACCTGCAGTGCCTGGAGGAGGAGCTGA

AGCCCCTGGAGGAGGTGCTGAACCTGGCCCAGAGCAAGAACTTTCACCTG

CGCCCCCGCGACCTGATCAGCAACATCAACGTGATCGTGCTGGAGCTGAA

GGGGAGCGAGACCACCTTTATGTGCGAGTACGCCGACGAGACCGCCACCA

TCGTGGAGTTTCTGAACCGCTGGATCACCTTTTGCCAGAGCATCATCAGC

ACCCTGACCTGA
```

The percentage of altered nucleotides in t with respect to s is 25%.

To properly evaluate optimization levels, random variants of the sequence were produced using the following algorithm:

Input:—a wild type sequence s
a reference set R

Output:—a randomized sequence r

1. For each amino acid A, compute its average synonymous codons density function F over all sequence in R:

$$F(C_{A,j}) = \frac{1}{|R|}\sum_{k=1}^{|R|} F^k(C_{A,j})$$

$$F^k(C_{A,j}) = \frac{q_{A,j}}{\sum_{j=1}^{m} q_{A,j}},\ \sum_{j=1}^{m} F(C_{A,j}) = 1$$

(where $\{C_{A,j}\}_{j=1}^{m}$ are m synonymous codons of said amino acid A; $q_{A,j}$ is the number of appearances of codon $C_{A,j}$ in the processed sequence; the superscript k stands for "the k-th reference sequence)

2. For each i-th codon in s (coding amino acid $A_i$):

2.1. x~U(0,1)

2.2. If x<F($C_{Ai,1}$) return Ci=$C_{Ai,1}$ else if x<F($C_{Ai,1}$)+F($C_{Ai,2}$) return Ci=$C_{Ai,2}$ else if x<F($C_{Ai,1}$)+ . . . +F($C_{Ai,m-1}$) return Ci=$C_{Ai,m-1}$ else return Ci=$C_{Ai,m}$ 2.3. r←r+Ci 3. return r=[C1, . . . , Ci, . . . ,Ck]

100 randomized variants were generated using the above algorithm according to the average CUB of: (1) all viral genes; (2) human genes (http://www.kazusa.or.jp/codon/cgi-bin/showcodon.cgi?species=9606). The evaluation of the optimization levels in comparison to these randomized variants is given in FIG. 9.

Example 9

Rational Design of Deoptimized Genes Based on Expression Period

Gene can also be designed that have deoptimized codons with respect to viral genes expressed during a defined period and this would result in minimal protein expression during a defined time period. To achieve this, codons would be selected with frequencies maximally dissimilar to the set of early or late genes than a random set of genes. This dissimilarity could be based on any metric of codon bias e.g. KL distance, Euclidean distance, L1, etc. or on any codon bias indexes (e.g. CAI).

To achieve this, the above mathematical algorithm was employed, but with the following replacement for steps 3 and 4:

3. For each codon $C_{A,i}$ in s:
Replace $C_{A,i}$ with a synonymous codon $C_{A,j}$ according to the synonymous rule $$C_{A,j} = \arg\max_{C_{A,k}} F_A(C_{A,k}).$$

4. Estimate the optimization level L(s) using one of the following:
Euclidian distance between two 1×64 vectors representing relative synonymous codons frequencies of $s_1$ and $s_2$; or
Codon Adaptation Index with respect to R (Sharp P M et al., Nucleic Acids Research, 1987, 15, 1281-95).
Relative Codon Deoptimization index (RCDI) with respect to R:

$$RCDI = \frac{1}{N}\sum_i \frac{F_s(C_i)}{F_R(Ci)} \times NC_i$$

$F_s(C_i)$ is the observed relative frequency in the tested sequence of each codon i out of all synonymous codons for the same amino acid (0 to 1), $F_R(C_i)$ is the relative frequency observed in the Reference set of each codon i out of all synonymous codons for that amino acid (0 to 1), $NC_i$ is the number of occurrences of that codon i in the sequence, and N is the total number of codons (amino acids) in the sequence. The higher the index, the more extensive deoptimization is.

This codon deoptimization was performed on the human Simplex virus (HHV-1) UL2 gene with respect to the set of Simplex virus early genes. That is, HHV-1 UL2 was recoded using the least frequent synonymous codons found in the Simplex virus early genes. This will minimize expression of UL2 protein during the early period of the Simplex virus life cycle.

The viral genome was downloaded from www.ncbi.nlm.nih.gov/nuccore/NC_001806.2, using the GenBank accession number NC_001806.2.

The deoptimized variant was engineered using the following inputs/definitions:
S=wild-type coding sequence of UL2 gene
R={UL2, UL5, UL8, UL12, UL23, UL29, UL30, UL39, UL40, UL42, UL50, UL52, US3}—a reference set of Simplex virus early genes (Roizman, 1996)
The synonymous rule is defined as: substitute each wild type codon with the least frequent codon in R. Codons frequencies are given in Appendix 1.
100 randomized variants were generated using the above algorithm according to the average CUB of: (1) all viral genes; (2) human genes (http://www.kazusa.or.jp/codon/cgi-bin/showcodon.cgi?species=9606).
The deoptimization evaluation function L was defined as: (1) Euclidean distance; (2) Codon Adaptation Index (CAI); (3) Relative Codon Deoptimization Index (RCDI)
The following deoptimized sequence was produced:

t =
(SEQ ID NO: 2)
ATGAAAAGAGCATGTAGTAGAAGTCCTAGTCCTAGAAGAAGACCTAGTAG

TCCTAGAAGAACTCCTCCTAGAGATGGTACTCCTCCTCAAAAAGCAGATG

-continued

CAGATGATCCTACTCCTGGTGCAAGTAATGATGCAAGTACTGAAACTAGA

CCTGGTAGTGGTGGTGAACCTGCAGCATGTAGAAGTAGTGGTCCTGCAGG

TGCACCTAGAAGACCTAGAGGTTGTCCTGCAGGTGTAACTTTCAGTAGTA

GTGCACCTCCTGATCCTCCTATGGATTTAACTAATGGTGGTGTAAGTCCT

GCAGCAACTAGTGCACCTTTAGATTGGACTACTTTCAGAAGAGTATTCTT

AATAGATGATGCATGGAGACCTTTAATGGAACCTGAATTAGCAAATCCTT

TAACTGCACATTTATTAGCAGAATATAATAGAAGATGTCAAACTGAAGAA

GTATTACCTCCTAGAGAAGATGTATTCAGTTGGACTAGATATTGTACTCC

TGATGAAGTAAGAGTAGTAATAATAGGTCAAGATCCTTATCATCATCCTG

GTCAAGCACATGGTTTAGCATTCAGTGTAAGAGCAAATGTACCTCCTCCT

CCTAGTTTAAGAAATGTATTAGCAGCAGTAAAAAATTGTTATCCTGAAGC

AAGAATGAGTGGTCATGGTTGTTTAGAAAAATGGGCAAGAGATGGTGTAT

TATTATTAAATACTACTTTAACTGTAAAAAGAGGTGCAGCAGCAAGTCAT

AGTAGAATAGGTTGGGATAGATTCGTAGGTGGTGTAATAAGAAGATTAGC

AGCAAGAAGACCTGGTTTAGTATTCATGTTATGGGGTACTCATGCACAAA

ATGCAATAAGACCTGATCCTAGAGTACATTGTGTATTAAAATTCAGTCAT

CCTAGTCCTTTAAGTAAAGTACCTTTCGGTACTTGTCAACATTTCTTAGT

AGCAAATAGATATTTAGAAACTAGAAGTATAAGTCCTATAGATTGGAGTG

TATAG

Figure 10:
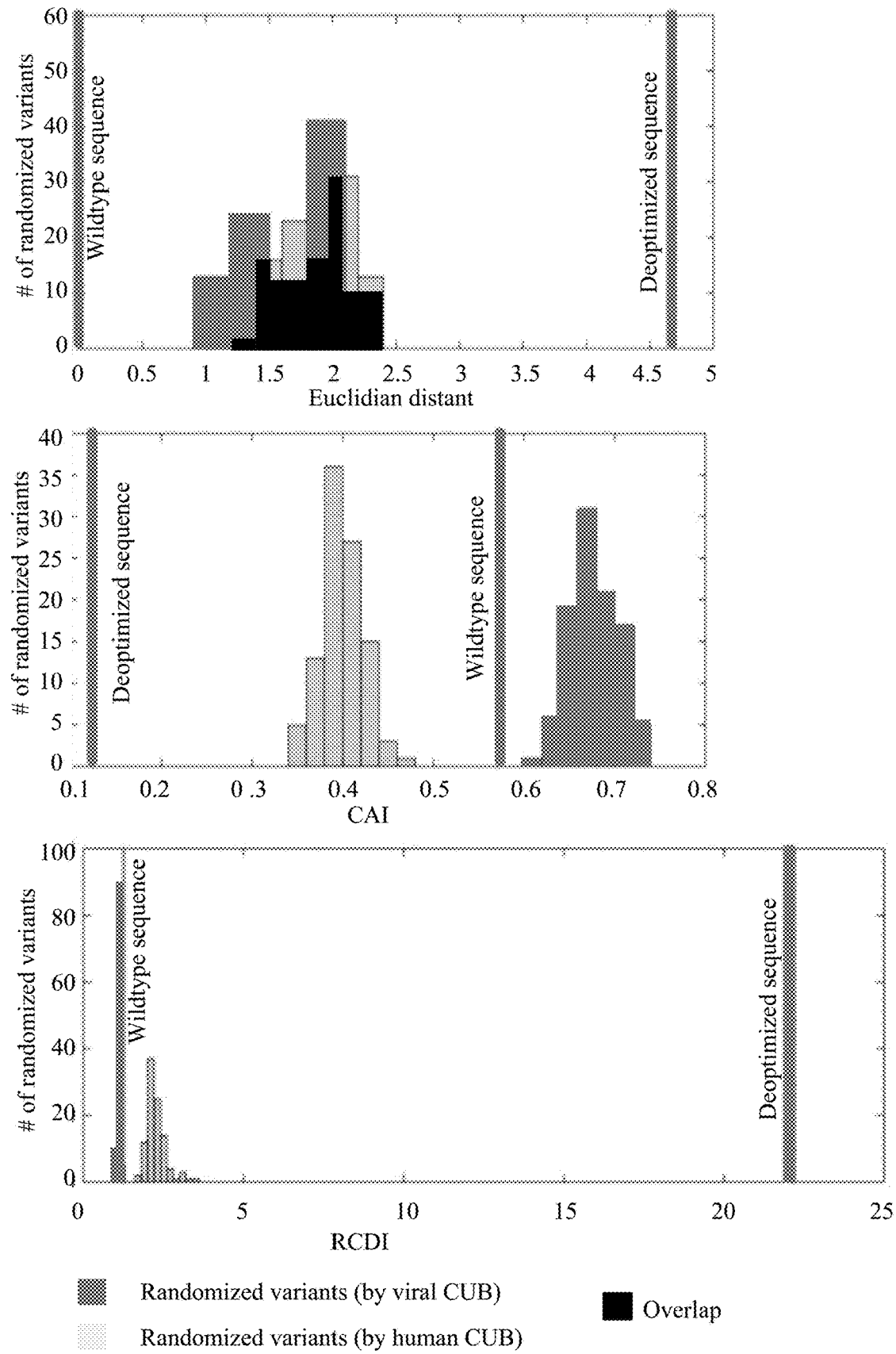
FIG. 10. Evaluation of Simplex virus UL2 gene deoptimization using Eucledian distance D, CAI and RCDI. Bar charts depicting UL2 gene deoptimization. Deoptimized evaluation values D(s,t)=4.69, CAI(t,R)=0.12, RCDI(t,R)=22.16 are given by "deoptimized variant" bars. Wild type evaluation values D(s,s)=0, CAI(s,R)=0.57, RCDI(s,R)=1.24 are given by "wild type sequence" bars. D(x, y)—Euclidian distance between synonymous codons relative frequency vectors of sequences x and y; CAI(x,R)/RCDI(x,R)—CAI/RCDI of sequence x with respect to the reference set R; s/t—wild-type/deoptimized UL2 coding sequences. The distribution of D/CAI/RCDI values for are given for variants randomized with respect to the average viral CUB and the average human CUB. P-value and Z-score estimations with respect to each random model is specified.

The percentage of altered nucleotides in t with respect to s is 37%. To properly evaluate optimization levels, random variants of the sequence were produced as described above. The evaluation of the optimization levels in comparison to these randomized variants is given in FIG. 10.

Example 9

Alteration of the Zika Virus by Exchange of Synonymous Codons

Figure 11A:
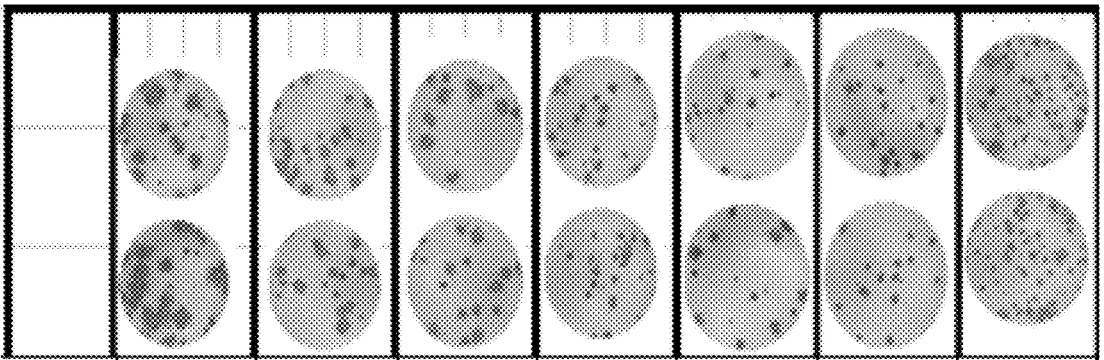
FIGS. 11A-B. Zika virus modification. (A) A table summarizing the 6 Zika variants, including the algorithm used for codon substitution, the number of codons changed, the predicted virulence, the foci relative size and representative micrographs of the virally-infected foci. (B) A bar chart showing viral titers at various time points after infection.
Figure 11B:
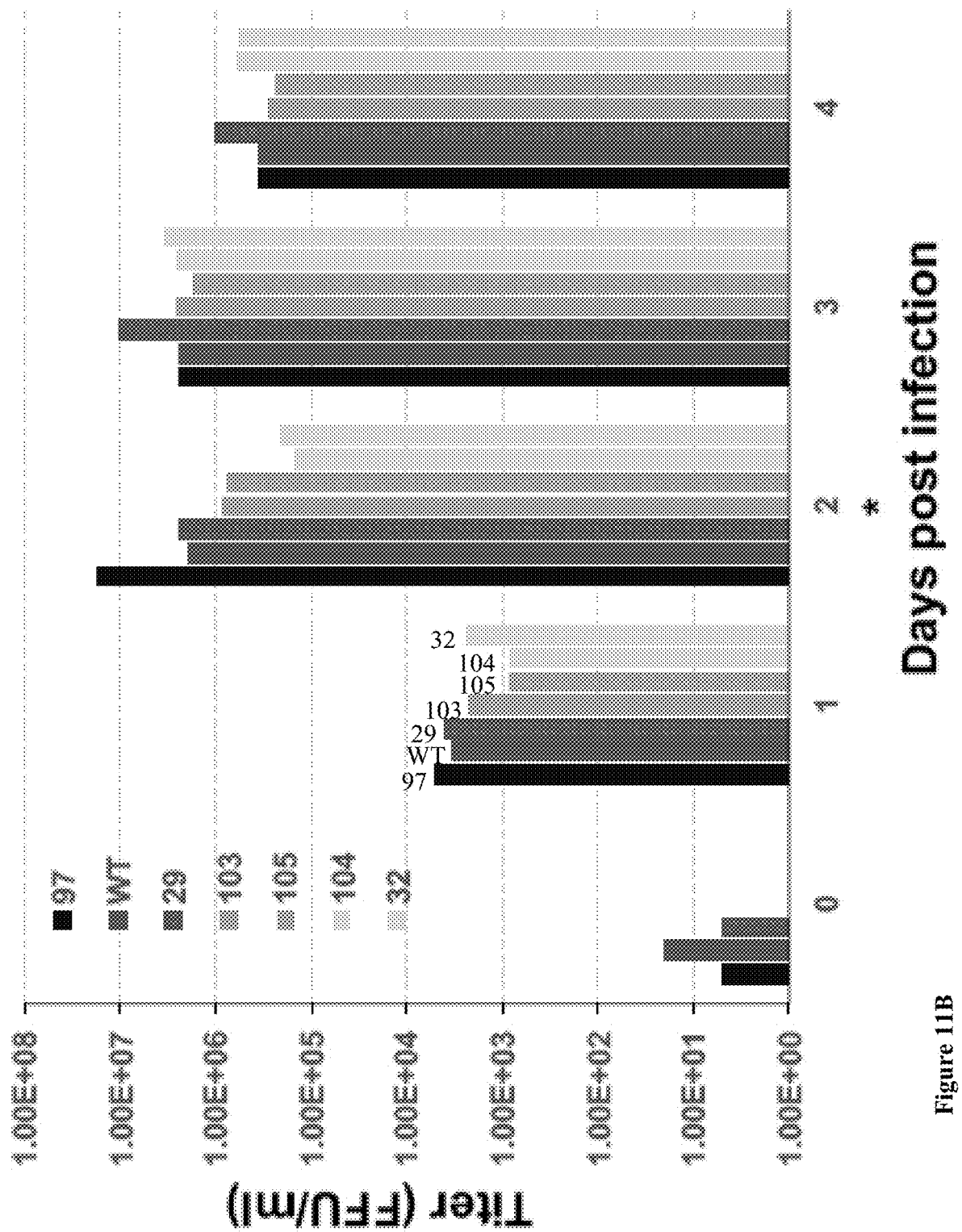

Codon alteration was now applied to the Zika virus. 6 modified variants of the virus Zika were designed; 4 variants comprised codon alterations that changed the folding energy of the Zika mRNA and 2 variants comprised codons altered to synonymous codons with a different relative frequency. As all Zika proteins are translated together, the codon substitutions were made based on a comparison to the entire Zika genome of various Zika strains. To test virus virulence a Focus Forming Assay (FFA) was performed. The monkey Vero cell line, which is infectible by Zika, was grown in a monolayer and then infected with the modified virus as well as wild-type virus. After 3 days, infected cells were visualized by immunostaining for the virus (FIG. 11A). Variants 32 (RSCF) and 104, 103 and 105 (folding) were all predicted to have reduced virulence and indeed all showed reduced size of virally infected foci. By contrast variant 29 (folding) resulted in only a negligible increase in virally infected foci, while variant 97 which was predicted to have increase virulence did indeed show larger viral foci. Viral titers from the infected cells were quantified and the 4 attenuated variants did indeed have reduced viral titers (FIG. 11B). Variant 29 showed a very slight increase in viral titers, and variant 97 showed a marked increase at early time points that appeared similar to the wild-type by day 3 (FIG. 11B) These results demonstrate that switching of codons to synonymous codons with different translation rates/efficiencies for a given set of viral genes can be an effect method for attenuating and enhancing a given virus.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A method for producing a nucleic acid molecule optimized or deoptimized for expression in a particular cellular context within a cell, the method comprising:
   a. selecting a coding sequence,
   b. selecting a reference set of genes expressed in a particular cellular context within a cell wherein said reference set is a subset of said cell's total genome or is a set of viral genes coordinately expressed in said cellular context and which are a subset of a virus's genome,
   c. for each codon of said coding sequence, computing a parameter that effects translation rate for said codon and its synonymous codons over all sequences in the reference set, and
   d. substituting at least one codon of said coding sequence with a synonymous codon with a faster rate of translation in said particular cellular context, in order to optimize said coding sequence or substituting at least one codon of said coding sequence with a synonymous codon with a slower rate of translation in said particular cellular context, in order to deoptimize said coding sequence,
thereby producing a nucleic acid molecule optimized or deoptimized for expression in a particular cellular context.

2. The method of claim 1, wherein said parameter that effects translation is selected from the group consisting of: relative synonymous codons frequencies (RSCF), and relative codon-tRNA adaptation and codon typical decoding rate (TDR).

3. The method of claim 1, wherein the particular cellular context is selected from the group consisting of: a specific period of a cell's life cycle, during cellular division, during cellular stress, during apoptosis, during viral infection, or during viral lysogeny of the cell.

4. A method for producing a modified virus, the method comprising:
   a. selecting an endogenous viral sequence,
   b. performing steps b-d of the method of claim 1 to optimize or deoptimize said endogenous viral sequence, thereby producing a reengineered viral sequence, wherein said selected coding sequence of steps b-d of the method of claim 1 is the selected endogenous viral sequence of step a, and
   c. replacing the endogenous viral sequence with the reengineered viral sequence, thereby producing a modified virus.

5. A method for producing an attenuated virus, the method comprising the method of claim 4 wherein,
   a. said viral sequence is an essential viral sequence, and
   b. said synonymous codon with a different translation rate has a slower translation rate, thereby producing an attenuated virus.

6. The method of claim 1, wherein said reference set of genes are genes whose mRNA is translated in said particular cellular context within a cell.

7. The method of claim 1, wherein said reference set of genes is a set of viral genes coordinately expressed in a particular cellular context within a cell wherein said reference set is a subset of said virus's total genome.

8. The method of claim 7, wherein said set of coordinately expressed viral genes is selected from the group consisting of: genes with a common structure, genes with common temporal expression during a virus's life cycle, genes encoding for proteins having common function, genes translated at a common cellular location and genes encoding for proteins having common cellular localization.

9. The method of claim 8, wherein said temporal expression during a virus's life cycle is selected from the group consisting of: early expression in the virus life cycle, intermediate expressing in the virus life cycle, and late expression in the virus life cycle.

10. The method of claim 8, wherein said parameter that effects translation rate is selected from the group consisting of: relative synonymous codons frequencies (RSCF), relative codon-tRNA adaptation, codon typical decoding rate (TDR), GC content, average repetitive substring index, codon pair bias, dinucleotide bias, nucleotide bias and amino acid bias.

11. A method for producing a nucleic acid molecule optimized or deoptimized for expression in a specific period of a cell's life cycle, the method comprising:
   a. selecting a coding sequence,
   b. selecting a reference set of genes expressed in specific period of a cell's life cycle wherein said reference set is a subset of said cell's total genome or is a set of viral genes coordinately expressed in said specific period of a cell's life cycle and which are a subset of a virus's genome, wherein said set of genes have a common temporal expression during a virus's life cycle,
   c. for each codon of said coding sequence, computing a parameter that effects translation rate for said codon and its synonymous codons over all sequences in the reference set, wherein said parameter is relative synonymous codons frequencies (RSCF), and
   d. substituting at least one codon of said coding sequence with a synonymous codon with a faster rate of translation in said specific period of a cell's life cycle, in order to optimize said coding sequence or substituting at least one codon of said coding sequence with a synonymous codon with a slower rate of translation in said specific period of a cell's life cycle, in order to deoptimize said coding sequence,
thereby producing a nucleic acid molecule optimized or deoptimized for expression in a specific period of a cell's life cycle.

12. A method for producing a modified virus, the method comprising:
   a. selecting an endogenous viral sequence,
   b. performing steps b-d of the method of claim 11 to optimize said endogenous viral sequence, thereby producing a reengineered viral sequence, wherein said selected coding sequence of steps b-d of the method of claim 11 is the selected endogenous viral sequence of step a, and
   c. replacing the endogenous viral sequence with the reengineered viral sequence, thereby producing a modified virus.

13. A method for producing an attenuated virus, the method comprising the method of claim 12 wherein,
   a. said viral sequence is an essential viral sequence, and
   b. said synonymous codon with a different translation rate has a slower translation rate, thereby producing an attenuated virus.

14. The method of claim 11, wherein said temporal expression during a virus's life cycle is selected from the group consisting of: early expression in the virus life cycle, intermediate expression in the virus life cycle, and late expression in the virus life cycle.

15. The method of claim 11, wherein said common temporal expression during a virus's life cycle of said set of genes is mRNA from said genes being translated at a common time in said virus's life cycle.

16. A method for producing a nucleic acid molecule optimized for expression in a specific period of a cell's life cycle, the method comprising:
- a. selecting a coding sequence,
- b. selecting a reference set of genes expressed in a specific period of a cell's life cycle wherein said reference set is a subset of said cell's total genome or is a set of viral genes coordinately expressed in said cellular context and which are a subset of a virus's genome, wherein said set of genes have a common temporal expression during a virus's life cycle,
- c. for each codon of said coding sequence, computing a parameter that effects translation rate for said codon and its synonymous codons over all sequences in the reference set, wherein said parameter is relative synonymous codons frequencies (RSCF), and
- d. substituting at least one codon of said coding sequence with a synonymous codon with a faster rate of translation in said specific period of a cell's life cycle, in order to optimize said coding sequence, thereby producing a nucleic acid molecule optimized for expression in specific period of a cell's life cycle.

17. The method of claim 16, wherein said temporal expression during a virus's life cycle is selected from the group consisting of: early expression in the virus life cycle, intermediate expression in the virus life cycle, and late expression in the virus life cycle.

18. The method of claim 16, wherein said common temporal expression during a virus's life cycle of said set of genes is mRNA from said genes being translated at a common time in said virus's life cycle.

* * * * *

SEQUENCE LISTING

<160> NUMBER OF SEQ ID NOS: 2

<210> SEQ ID NO 1
<211> LENGTH: 462
<212> TYPE: DNA
<213> ORGANISM: Human

<400> SEQUENCE: 1
atgtaccgca tgcagctgct gagctgcatc gccctgagcc tggccctggt gaccaacagc 60
gcccccacca gcagcagcac caagaagacc cagctgcagc tggagcacct gctgctggac 120
ctgcagatga tcctgaacgg gatcaacaac tacaagaacc ccaagctgac ccgcatgctg 180
acctttaagt tttacatgcc caagaaggcc accgagctga agcacctgca gtgcctggag 240
gaggagctga agcccctgga ggaggtgctg aacctggccc agagcaagaa ctttcacctg 300
cgcccccgcg acctgatcag caacatcaac gtgatcgtgc tggagctgaa ggggagcgag 360
accaccttta tgtgcgagta cgccgacgag accgccacca tcgtggagtt tctgaaccgc 420
tggatcacct tttgccagag catcatcagc accctgacct ga 462

<210> SEQ ID NO 2
<211> LENGTH: 1005
<212> TYPE: DNA
<213> ORGANISM: Human symplex virus

<400> SEQUENCE: 2
atgaaaagag catgtagtag aagtcctagt cctagaagaa gacctagtag tcctagaaga 60
actcctccta gagatggtac tcctcctcaa aaagcagatg cagatgatcc tactcctggt 120
gcaagtaatg atgcaagtac tgaaactaga cctggtagtg gtggtgaacc tgcagcatgt 180
agaagtagtg gtcctgcagg tgcacctaga agacctagag gttgtcctgc aggtgtaact 240
ttcagtagta gtgcacctcc tgatcctcct atggatttaa ctaatggtgg tgtaagtcct 300
gcagcaacta gtgcaccttt agattggact actttcagaa gagtattctt aatagatgat 360
gcatggagac ctttaatgga acctgaatta gcaaatcctt taactgcaca tttattagca 420
gaatataata gaagatgtca aactgaagaa gtattacctc ctagagaaga tgtattcagt 480
tggactagat attgtactcc tgatgaagta agagtagtaa taataggtca agatccttat 540
catcatcctg gtcaagcaca tggtttagca ttcagtgtaa gagcaaatgt acctcctcct 600
cctagtttaa gaaatgtatt agcagcagta aaaaattgtt atcctgaagc aagaatgagt 660
ggtcatggtt gtttagaaaa atgggcaaga gatggtgtat tattattaaa tactacttta 720
actgtaaaaa gaggtgcagc agcaagtcat agtagaatag gttgggatag attcgtaggt 780
ggtgtaataa gaagattagc agcaagaaga cctggtttag tattcatgtt atggggtact 840
catgcacaaa atgcaataag acctgatcct agagtacatt gtgtattaaa attcagtcat 900
cctagtcctt taagtaaagt acctttcggt acttgtcaac atttcttagt agcaaataga 960
tatttagaaa ctagaagtat aagtcctata gattggagtg tatag 1005